US008608801B2

(12) United States Patent
Hung et al.

(10) Patent No.: US 8,608,801 B2
(45) Date of Patent: Dec. 17, 2013

(54) OSTEOCHONDRAL IMPLANTS, ARTHROPLASTY METHODS, DEVICES, AND SYSTEMS

(75) Inventors: Clark T. Hung, Ardsley, NY (US); Gerard A. Ateshian, New York, NY (US); Eric G. Lima, Patterson, NY (US); James L. Cook, Columbia, MO (US); Li Ming Bian, New York, NY (US)

(73) Assignees: The Trustees of Columbia University in the City of New York, New York, NY (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 12/498,358

(22) Filed: Jul. 6, 2009

(65) Prior Publication Data
US 2010/0036492 A1 Feb. 11, 2010

Related U.S. Application Data

(60) Provisional application No. 61/078,424, filed on Jul. 6, 2008.

(51) Int. Cl.
*A61F 2/30* (2006.01)
(52) U.S. Cl.
USPC ..................................... 623/14.12; 623/23.51
(58) Field of Classification Search
USPC ........................................... 623/14.12, 23.63
See application file for complete search history.

(56) References Cited

U.S. PATENT DOCUMENTS

| 5,206,028 | A | * | 4/1993 | Li | 424/484 |
| 5,282,861 | A | | 2/1994 | Kaplan | |
| 6,242,247 | B1 | * | 6/2001 | Rieser et al. | 435/297.1 |
| 7,935,363 | B2 | * | 5/2011 | Ratcliffe | 424/443 |
| 2002/0106625 | A1 | | 8/2002 | Hung et al. | |
| 2003/0004578 | A1 | * | 1/2003 | Brown et al. | 623/23.72 |
| 2003/0153078 | A1 | | 8/2003 | Libera et al. | |
| 2004/0197367 | A1 | | 10/2004 | Rezania et al. | |
| 2006/0036331 | A1 | | 2/2006 | Lu et al. | |
| 2007/0128245 | A1 | | 6/2007 | Rosenberg et al. | |

(Continued)

FOREIGN PATENT DOCUMENTS

| DE | 203 15 960 U1 * | 3/2004 | A61F 2/28 |
| WO | WO 96/24310 A1 * | 8/1996 | A61F 2/30 |

(Continued)

OTHER PUBLICATIONS

Machine-generated translation of DE 203 15 960 U1 (published on Mar. 18, 2004).*

(Continued)

*Primary Examiner* — David H Willse
(74) *Attorney, Agent, or Firm* — Senniger Powers LLP

(57) ABSTRACT

Implants for resurfacing or repairing one or more articular cartilage bearing surfaces of a biological organism include an engineered tissue and a biocompatible porous substrate secured to the engineered tissue for attaching the implant to a native bone of the biological organism. The engineered tissue includes a scaffold containing a biocompatible material, and a plurality of living chondrocytes supported by the scaffold. Methods for culturing chondrocytes for incorporation into a biocompatible implant are provided. A bioreactor for producing functional cartilaginous tissue from a cell-seeded scaffold and a system for producing functional cartilaginous tissue are also provided.

39 Claims, 48 Drawing Sheets

(56) References Cited

U.S. PATENT DOCUMENTS

| | | | |
|---|---|---|---|
| 2007/0134291 A1* | 6/2007 | Ting et al. | 424/423 |
| 2007/0173945 A1 | 7/2007 | Wiley et al. | |
| 2007/0255412 A1 | 11/2007 | Hajaj et al. | |

FOREIGN PATENT DOCUMENTS

| | | | |
|---|---|---|---|
| WO | 98/40111 A1 | 9/1998 | |
| WO | 0168800 A1 | 9/2001 | |
| WO | WO 02/17820 A1 * | 3/2002 | A61F 2/30 |
| WO | 2007025290 A2 | 3/2007 | |

OTHER PUBLICATIONS

Ateshian, G. A., et al., "Patellofemoral Joint Biomechanics and Tissue Engineering," Clinical Orthopaedics and Related Research, Jul. 2005, pp. 81-90, No. 81.

Bian, L., et al., "Influence of Decreasing Nutrient Path Length on the Development of Engineering Cartilage," Osteoarthritis and Cartilage, 2008, pp. 1-9.

Francioli, S.-E., et al., "Growth Factors for Clinical-Scale Expansion of Human Articular Chondrocytes: Relevance for Automated Bioreactor Systems," Tissue Engineering, 2007, pp. 1227-1234, vol. 13, No. 6.

Ho, M. M. Y., et al., "Gelling Temperature and Gel Concentration Effects on Tissue Development in Chondrocyte-Seeded Agarose Hydrogels," Summer Bioengineering Conference, Jun. 25-29, 2003, 2 pages.

Hung, C. T., et al., "Anatomically Shaped Osteochondral Constructs for Articular Cartilage Repair," Journal of Biomechanics, 2003, pp. 1853-1864, vol. 36.

Hung, C. T., et al., "Functional Tissue Engineering of Articular Cartilage Using Adult Chondrocytes," International Cartilage Repair Society, Geistlich Surgery, 2009, e-Poster Submission, 14 pages.

Hung, C. T., et al., "A Paradigm for Functional Tissue Engineering of Articular Cartilage via Applied Physiologic Deformational Loading," Annals of Biomedical Engineering, Jan. 2004, pp. 35-49, vol. 32, No. 1.

Kelly, T.-A. N., et al., "Spatial and Temporal Development of Chondrocyte-Seeded Agarose Constructs in Free-Swelling and Dynamically Loaded Cultures," Journal of Biomechanics, 2006, pp. 1489-1497, vol. 39.

Lee, D. A., et al., "Compressive Strains at Physiological Frequencies Influence the Metabolism of Chondrocytes Seeded in Agarose," Journal of Orthopaedic Research, Mar. 1997, pp. 181-188, vol. 15, No. 2.

Lima, E. G., et al., "The Beneficial Effect of Delayed Compressive Loading on Tissue-Engineered Cartilage Constructs Cultured with TGF-β3," Osteoarthritis and Cartilage, 2007, pp. 1025-1033, vol. 15, No. 9.

Lima, E. G., et al., "The Effect of Devitalized Trabecular Bone on the Formation of Osteochondral Tissue-Engineered Constructs," Biomaterials, 2008, pp. 4292-4299, vol. 29.

Lima, E. G., et al., "Physiologic Deformational Loading Does Not Counteract the Catabolic Effects of Interleukin-1 in Long-Term Culture of Chondrocyte-Seeded Agarose Constructs," Journal of Biomechanics, 2008, pp. 3253-3259, vol. 41.

Mauck, R. L., et al., "Influence of Seeding Density and Dynamic Deformational Loading on the Developing Structure/Function Relationships of Chondrocyte-Seeded Agarose Hydrogels," Annals of Biomedical Engineering, 2002, pp. 1046-1056, vol. 30.

Ng, K. W., et al., "A Layered Agarose Approach to Fabricate Depth-Dependent Inhomogeneity in Chondrocyte-Seeded Constructs," Journal of Orthopaedic Research, 2005, pp. 134-141, vol. 23.

Sigma-Aldrich, Agarose Product Information, Oct. 21, 1996, 8 pages.

Tan, A. R., et al., "Type Ix Agarose Gel Produces Better Tissue Engineered Cartilage Constructs than Type VII Agarose," ORS Meeting, 2009, 1 page.

Techman, A., "Zimmer and ISTO Start Clinical Trial of Neocartilage (DeNovo® ET Engineered Tissue Graft), A Novel Cartilage Regeneration Treatment," Musculoskeletal Report, http://www.mskreport.com/articles.cfm?articleID=1190, accessed on May 7, 2009, 2 pages.

Zimmer Holdings, Inc., "Zimmer Holdings and ISTO Technologies Announce Start of Neocartilage Clinical Trial," http://www.accessibility.com.au/news/zimmer-holdings-and-isto-technologies-announce-start-of-neocartilage-clinical-trial, accessed on May 7, 2009, 1 page.

Zimmer Holdings, Inc., "Trabecular Metal™ Technology," http://www.zimmer.com/z/ctl/op/global/action/1/id/33/template/MP/navid/294, date unknown, available at least as early as Mar. 3, 2009, 9 pages.

Invitation to Pay Additional Fees and Partial Search regarding related PCT/US2009/049733, mailed Feb. 2, 2010, 4 pages.

International Search Report, PCT/US2009/049733, dated Mar. 16, 2010, 5 Pages.

Byers, B. A., et al., "Temporal Exposure of TGF-β3 Under Serum-Free Conditions Enhances Biomechanical and Biochemical Maturation of Tissue-Engineered Cartilage," 52nd Annual Meeting of the Orthopaedic Research Society held Mar. 19-22, 2006, Paper No. 0043.

Cook, J. L. et al., "Towards Biologic Osteochondral Resurfacing of the Canine Patella Using Tissue Engineered Anatomic Constructs," 55th Annual Meeting of the Orthopaedic Research Society held Feb. 22-24, 2009, Poster No. 1355.

Lima, E. G., et al., "Porous Tantalum Metal Outperforms Devitalized Bone as a Substrate for Osteochondral Tissue Engineering," 55th Annual Meeting of the Orthopaedic Research Society held Feb. 22-24, 2009, Paper No. 124.

Ng, K. W., et al., "Designing Depth-Varying Cellular and Mechanical Inhomogeneity in Engineered Cartilage," 54th Annual Meeting of the Orthopaedic Research Society held Dec. 11-15, 2005, Paper No. 378.

Ng, K. W., et al., "In Vivo Response to Canine Chondral and Osteochondral Engineering Cartilage Implantation," 55th Annual Meeting of the Orthopaedic Research Society held Feb. 22-24, 2009, Paper No. 60.

Ng, K. W., et al., "Primed Mature Canine Chondrocytes can Develop an Engineered Cartilage Tissue with Physiologic Properties," 54th Annual Meeting of the Orthopaedic Research Society held Mar. 2-5, 2008, Poster No. 599.

Ng, K. W., et al., "The Response of Adult Engineered Canine Cartilage to the Sequential or Combined Application of TGF-β3 and IGF-I," 55th Annual Meeting of the Orthopaedic Research Society held Feb. 22-24, 2009, Poster No. 1017.

Ng, K. W., et al., "The Response of Engineered Cartilage to a Timed Application of Transforming and Insulin-Like Growth Factors," 54th Annual Meeting of the Orthopaedic Research Society held Mar. 2-5, 2008, Poster No. 588.

Cook, J. L., et al., "Biocompatibility of Three-Dimensional Chondrocyte Grafts in Large Tibial Defects of Rabbits," American Journal of Veterinary Research, Jan. 2003, pp. 12-20, vol. 64, No. 1.

Lima, E. G., et al., "Functional Tissue Engineering of Chondral and Osteochondral Constructs," Biorheology, 2004, pp. 577-590, vol. 41, No. 3-4.

Mauck, R. L., et al., "Synergistic Action of Growth Factors and Dynamic Loading for Articular Cartilage Tissue Engineering," Tissue Engineering, Aug. 2003, pp. 597-611, vol. 9, No. 4.

Mauck, R. L., et al., "The Role of Cell Seeding Density and Nutrient Supply for Articular Cartilage Tissue Engineering with Deformational Loading," Osteoarthritis and Cartilage, Dec. 2003, pp. 879-890, vol. 11, No. 12.

Extended Search Report dated Jan. 4, 2013 for Application No. PCT/US2009049733, 6 pages.

\* cited by examiner

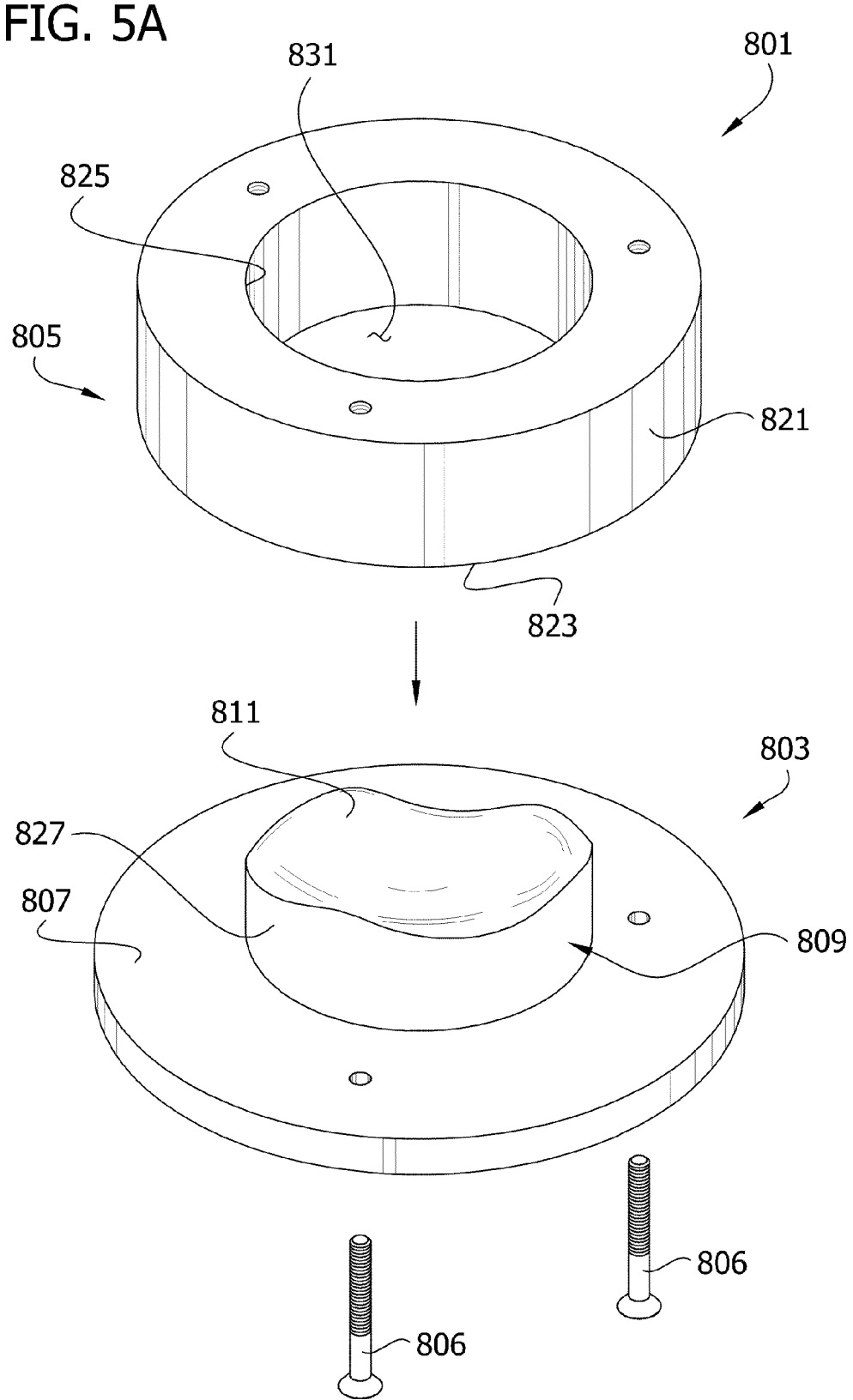

OSTEOCHONDRAL IMPLANTS, ARTHROPLASTY METHODS, DEVICES, AND SYSTEMS

CROSS-REFERENCE TO RELATED APPLICATIONS

This application is a Non-Provisional Patent Application of U.S. Provisional Patent Application Ser. No. 61/078,424, filed Jul. 6, 2008, the entirety of which is herein incorporated by reference.

STATEMENT OF GOVERNMENT INTEREST

This invention was made with United States government support under AR46568 and AR53530 awarded by National Institute of Health. The United States government has certain rights in the invention.

BACKGROUND

Articular cartilage is a specialized connective tissue that bears load and reduces friction across moving joints. It is composed of an extracellular matrix that contains no nerves or blood vessels and relatively few cells (5% volume). Damage can arise due to disease or trauma and is common, especially in the aging population. Cartilage can decrease in strength with age. When damaged, articular cartilage either does not heal or at best heals only very slowly. Instead of healing, damaged cartilage often degenerates further, leading to pain and loss of function. Due to the prevalence of osteoarthritis (OA) and damage to articular cartilage, coupled with this poor intrinsic healing response, there is a great demand for clinical intervention.

Treatment of damaged cartilage in living animals presents difficult challenges. Adult cartilage is difficult to repair. Joint repair is conventionally done by replacing the entire joint or joint surfaces without trying to repair cartilage, usually in the form of a highly-invasive non-biological prosthetic (such as total joint arthroplasty). However, metal/plastic orthopedic implants have a limited lifespan (e.g., about 20 years) and are ideally reserved for use in older patients. The onset of arthritis, however, can begin as early as the age of 40 with much younger patients suffering from the disease as a result of trauma. Thus, some patients face the prospect that an artificial joint implant may wear out and need to be replaced.

One common biological alternative to arthroplasty entails the transplantation of healthy osteochondral autografts (cartilage along with some of the underlying bone) from a non-load bearing region. Osteochondral implants are designed to be press-fit into pre-drilled cavities in the damaged joint, replacing the host cartilage above while anchoring to the bone below. Osteochondral grafts are better anchored than chondral-only grafts and are less likely to be displaced by shearing forces within the joint. While these autologous grafting procedures are promising, they are limited both by the amount of tissue available and donor-site morbidity associated with its harvest. The use of donor cartilage from tissue banks (allografts) or from animal origin (xenografts) addresses these limitations, but introduces the possibility of disease transmission.

Tissue engineering strategies, if successful, could alleviate these problems by creating replacement tissues of the proper size and shape without concurrent damage to other regions of the patient's body. There is a great variety of tissue engineering approaches to form osteochondral constructs. For example, techniques for repairing cartilage have been proposed using scaffolds implanted with progenitor cells such as chondrocytes, stromal cells, stem cells, and such. However, clinical outcomes with biologic replacement materials have not been satisfactory, particularly because of mechanical issues, morphology and durability of biologics-based replacements.

SUMMARY

Briefly, some aspects of the inventions include a two part implant with a biologic part and an artificial (or non-living biologic material) part. The implant can be grown in vitro and implanted such that the biologic part forms an articular surface of a joint. The invention also includes devices, systems, and methods for making, implanting, and treating patients and associated articles of manufacture.

Hybrid Synthetic-Biologic Joint Arthroplasty Systems comprise a group of related implants and techniques that provide a variety of options for performing joint replacement and resurfacing surgeries. The components may be similar for all systems and include implants for replacement or resurfacing of joint cartilage and bone, and techniques for tissue harvest, processing, and implantation. The implants may be composed of a synthetic component (e.g., metal, polymer, biomaterial) and a biologic component (e.g., tissue, cells, matrix) combined together. The hybrid implants are preferably designed to optimize long term success in joint replacement and resurfacing surgery of all major joints (hip, knee, ankle, shoulder, elbow, and fingers) by combining the advantages of synthetic and biologic arthroplasty techniques while minimizing the disadvantages of each.

The basic components for each system are: prostheses designed for replacement or resurfacing of articular cartilage and bone, and techniques for tissue harvest, processing, and implantation. The prostheses are composed of a synthetic component (e.g., metal, polymer, biomaterial) and a biologic component (e.g., tissue, cells, matrix). These hybrid prostheses allow for creating joint specific partial or complete hemi or total arthroplasty.

Some basic embodiments for the hybrid prostheses include a cylindrical synthetic base with tissue engineered chondral layer and an anatomic synthetic base with tissue engineered chondral layer.

An immediate application of an engineered articular cartilage bearing surface is focal defect repair or resurfacing of an entire articular surface. The treatments are used, for example, for focal cartilage defects of the knee, ankle, elbow, and shoulder, partial and complete hemi and total joint arthroplasty of the knee, shoulder, hip, ankle, elbow, wrist, temporomandibular joint (TMJ), fingers, and toes—potentially millions of procedures each year worldwide. A biologic articular surface (versus plastic or metal) anchored to joints via a metal component. In an entire system, the process of using allogeneic chondrocytes that are expanded in culture and then seeded into an appropriate hydrogel that is integrated with an appropriate underlying "bony" base may be used. Additionally, techniques and design elements that provide fixation of the engineered hybrid construct implants are included.

The hybrid implant systems and related methods described herein are designed to improve long term success in joint replacement and resurfacing surgery of the hip, knee, ankle, shoulder, elbow, wrist, TMJ, fingers, and toes by combining the advantages of synthetic and biologic arthroplasty systems while minimizing the disadvantages of each. Specifically, the advantages of synthetic arthroplasty that can be obtained from the hybrid implants include: (1) functional replacement of bone; (2) ability to size and shape implants appropriately; (3) excellent implantation and fixation techniques; (4) immediate biomechanical function. The advantages of biologic arthroplasty that can be obtained from the hybrid implants include: (1) creation of living, site appropriate tissue with implant-host integration; (2) minimizing amount of foreign material in the body; (3) potential for continued remodeling; (4) improvement in tissue/joint characteristics and function; and (5) public perception and interest.

The disadvantages of synthetic systems that can be minimized using hybrid implants are: (1) metal and polymer breakdown products and their effects; (2) lack of long term durability and function; and (3) loss of future arthroplasty options. The disadvantages of biologic systems that can be minimized using the hybrid implants include: (1) the large amount of tissue required; (2) problems associated with cartilage-cartilage and cartilage-bone integration; (3) requirements for immediate load bearing function; (4) devitalized trabecular bone may have an inhibitory effect on in vitro chondral tissue development when used as a base material for the tissue-engineering of osteochondral constructs for cartilage repair.

One aspect of the invention is an implant for resurfacing or repairing one or more articular cartilage bearing surfaces of a biological organism. The implant includes an engineered tissue and a biocompatible porous substrate secured to the engineered tissue for attaching the implant to a native bone of the biological organism. The engineered tissue includes a scaffold containing a biocompatible material, and a plurality of living chondrocytes supported by the scaffold. The porous base substrate is substantially free of trabecular bone. In some instances, the porous substrate includes a metal such as tantalum. In other instances, the porous substrate includes a synthetic polymer or biologic material. The synthetic polymer can be polycaprolactone, poly-l-lactic acid, or polyglycolic acid. In some cases, the biologic material is collagen or hydroxyapatite. The scaffold contains a hydrogel such as agarose or alginate in some embodiments. In some implants, the engineered tissue has a bearing surface that has substantially the same shape of at least a portion of one of the one or more articular cartilage bearing surfaces that is to be resurfaced or repaired. The engineered tissue can have a bearing surface that has substantially the same shape as one of the one or more articular cartilage bearing surfaces that is to be resurfaced. In some cases, the engineered tissue has a total surface area in the range of about 0.05 cm$^2$ to about 50 cm$^2$, or a volume in the range of about 0.005 ml to about 80 ml. In some embodiments, the engineered tissue contains Type II collagen in an amount in the range of about 2 percent (w/w) to about 8 percent (w/w) or about 4 percent (w/w) to about 8 percent (w/w), a glycosaminoglycan (GAG) content in the range of about 4 percent (w/w) to about 10 percent (w/w) or about 5 percent (w/w) to about 8 percent (w/w), or an equilibrium Young's modulus ($E_Y$) of at least about 150 kPa. In some embodiments, the engineered tissue has an equilibrium Young's modulus ($E_Y$) in the range of about 150 kPa to about 1500 kPa, about 185 kPa to about 1300 kPa, about 275 kPa to about 1300 kPa, or about 800 kPa to about 1300 kPa.

Another aspect of the invention is directed to an implant for resurfacing or repairing one or more articular cartilage bearing surfaces of a biological organism, in which the implant includes an engineered tissue. The engineered tissue includes a scaffold containing a biocompatible material, and a plurality of living chondrocytes supported by the scaffold. The engineered tissue has an equilibrium Young's modulus ($E_Y$) of at least about 150 kPa. In some instances, the engineered tissue has an equilibrium Young's modulus ($E_Y$) in the ranges as described above. In some embodiments, the engineered tissue contains Type II collagen in an amount as described above, or has glycosaminoglycan (GAG) content in the range described above. In some aspects of the invention, the implant also includes a porous substrate secured to the engineered tissue for attaching the implant to a native bone of the biological organism. The porous substrate can be substantially free of trabecular bone. In some embodiments, the scaffold contains a hydrogel as described above. In other embodiments, the engineered tissue has a bearing surface as described above or has a total surface area or volume as described above.

Yet another aspect of the invention is directed to a method for culturing chondrocytes for incorporation into a biocompatible implant. A plurality of adult living chondrocytes are passaged in the presence of one or more growth factors. The chondrocytes are suspended in a gelable scaffold material. The chondrocytes and the gelable scaffold material is cultured in a medium containing transforming growth factor-beta3 (TGF-beta3). In some instances, the suspension of chondrocytes and gelable scaffold material is casted into one or more slabs, and the one or more slabs are cored to create one or more disks. In some embodiments, the suspension of chondrocytes and gelable scaffold material are secured to a biocompatible porous substrate. The suspension of chondrocytes and gelable scaffold material can be transferred to a mold and the biocompatible porous substrate substantially free of trabecular bone can be immersed into the chondrocytes and gelable scaffold material. In some instances, the biocompatible porous substrate contains a metal, a synthetic polymer or a biologic material as described above. In further embodiments, chondrocytes obtained from an autologous donor are passaged, while in other instances, chondrocytes obtained from an allogeneic donor are passaged. In some cases, adult canine chondrocytes are passaged. In the method of the invention, the chondrocytes can be passaged in the continuous presence of one or more growth factors.

Another aspect of the invention is a bioreactor for producing functional cartilaginous tissue from a cell-seeded scaffold. The bioreactor includes a support for supporting the cell-seeded scaffold, a platen, and a drive system. The drive system is operable to move the platen relative to the support to compress the cell-seeded scaffold while it is supported by the support and slide the platen on a surface of the compressed cell-seeded scaffold. In some instances, the cell-seeded scaffold has a bearing surface and the drive system is operable to slide the platen on the bearing surface, the platen being configured so no more than about half of the bearing surface is covered by the platen at any time.

Yet another embodiment of the invention is a system for producing functional cartilaginous tissue. The system includes a cell-seeded scaffold, a support supporting the cell-seeded scaffold, a platen, and a drive system. The drive system is operable to move the platen relative to the cell-seeded scaffold to sequentially (a) compress a first portion of the cell-seeded scaffold while temporarily maintaining a second portion of the cell-seeded scaffold different from said first portion in a substantially uncompressed state; and (b) compress the second portion of the cell-seeded scaffold while temporarily maintaining the first portion in a substantially uncompressed state.

Still another aspect of the invention is a method for producing functional cartilaginous tissue from a cell-seeded scaffold. The cell-seeded scaffold is compressed with a platen and the platen is slid on a surface of the compressed cell-seeded scaffold. In some instances, the cell-seeded scaffold is made by a process in which a plurality of living chondrocytes is suspended in a gelable scaffold material, and the chondrocytes and the gelable scaffold material are cultured in a medium containing transforming growth factor-beta (TGF-beta). In some embodiments, the suspension of chondrocytes and gelable scaffold material is molded into one or more slabs. One or more bodies can be excised from the one or more slabs, the bodies each having an average thickness of about 1 mm to about 6 mm or about 1 mm to about 4 mm. In some cases, the suspension of chondrocytes and gelable scaffold material is secured to a biocompatible porous substrate.

The suspension of chondrocytes and gelable scaffold material can be transferred to a mold, and the biocompatible porous substrate substantially free of trabecular bone can be immersed into the chondrocytes and gelable scaffold material. In some instances, the biocompatible porous substrate contains a metal, a synthetic polymer or a biologic material as described above. Chondrocytes obtained from an adult human or animal subject are used in some embodiments, and the chondrocytes are passaged in the presence of one or more growth factors, such as TGF-beta, fibroblast growth factor-2 (FGF-2), and platelet-derived growth factor-BB (PDGF-BB).

Yet another embodiment of the invention is directed to a method for producing functional cartilaginous tissue from a cell-seeded scaffold. A first portion of the cell-seeded scaffold is compressed while temporarily maintaining a second portion of the cell-seeded scaffold different from the first portion in a substantially uncompressed state. The second portion of the cell-seeded scaffold is compressed while temporarily maintaining the first portion in a substantially uncompressed state. In some instances, the cell-seeded scaffold is made by a process in which a plurality of living chondrocytes is suspended in a gelable scaffold material, and the chondrocytes and the gelable scaffold material are cultured in a medium containing transforming growth factor-beta (TGF-beta). In some embodiments, the suspension of chondrocytes and gelable scaffold material is molded into one or more slabs. One or more bodies can be excised from the one or more slabs, the bodies each having an average thickness of about 1 mm to about 6 mm or about 1 mm to about 4 mm. In some cases, the suspension of chondrocytes and gelable scaffold material is secured to a biocompatible porous substrate. The suspension of chondrocytes and gelable scaffold material can be transferred to a mold, and the biocompatible porous substrate substantially free of trabecular bone can be immersed into the chondrocytes and gelable scaffold material. In some instances, the biocompatible porous substrate contains a metal, a synthetic polymer or a biologic material as described above. Chondrocytes obtained from an adult human or animal subject are used in some embodiments, and the chondrocytes are passaged in the presence of one or more growth factors, such as TGF-beta, fibroblast growth factor-2 (FGF-2), and platelet-derived growth factor-BB (PDGF-BB).

Other objects and features will be in part apparent and in part pointed out hereinafter.

BRIEF DESCRIPTION OF THE DRAWINGS

FIGS. 5A-5G illustrate a sequence of one embodiment of a method of making an osteochondral implant;

Corresponding reference characters indicate corresponding parts throughout the drawings.

DETAILED DESCRIPTION

Figure 1:
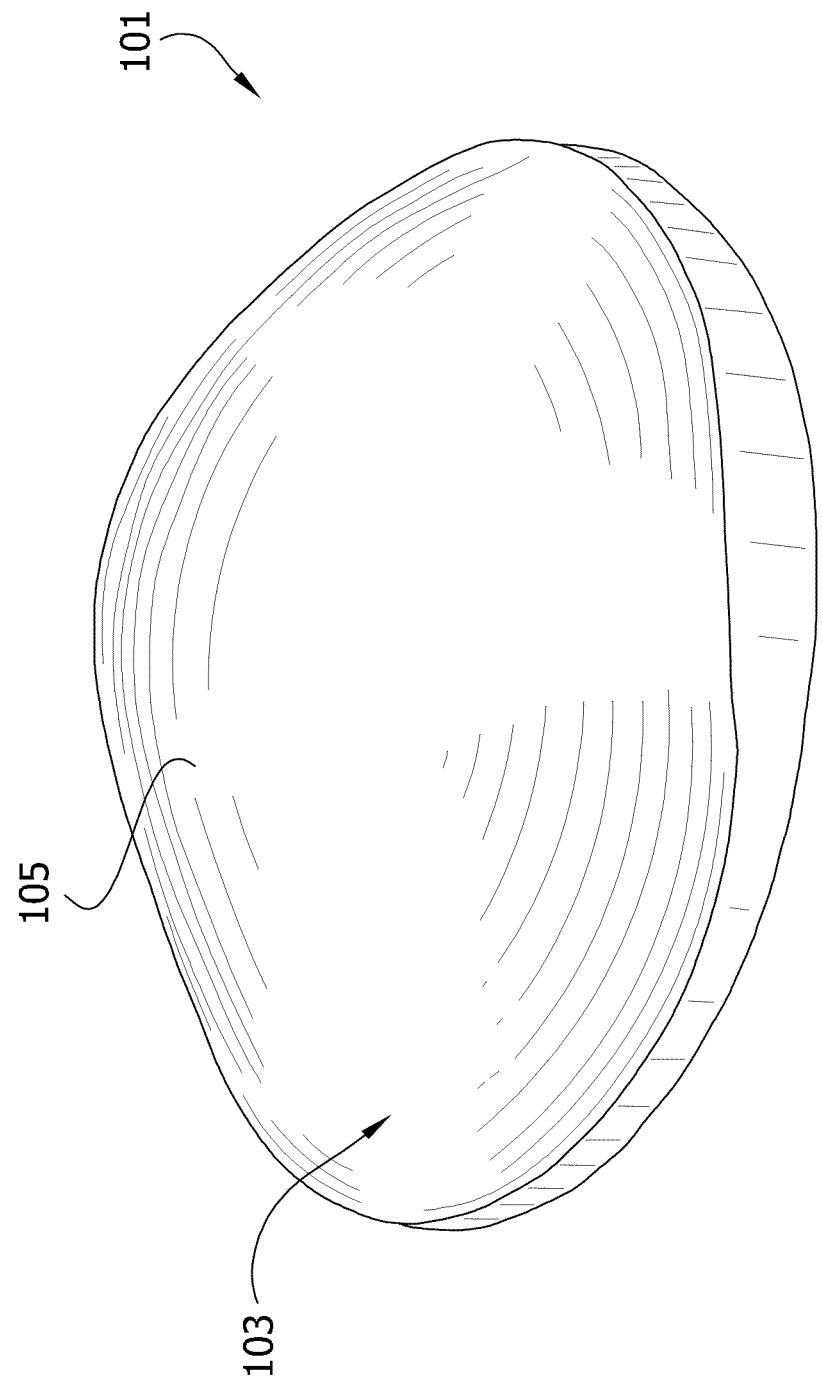
FIG. 1 is a perspective of one embodiment of a chondral implant.

Referring now to the drawings, one embodiment of a chondral implant, generally designated 101, is illustrated in FIG. 1. The chondral implant 101 includes an engineered tissue 103 that is suitable for resurfacing or repairing one or more articular cartilage bearing surfaces of a biological organism, and in particular humans and other vertebrates. The engineered tissue 103 includes a scaffold comprising a biocompatible material and a plurality of living chondrocytes (which are the principle cells that synthesize and maintain extracellular components of cartilaginous tissue) supported by the scaffold. The scaffold, chondrocytes, extracellular components, and other components of the engineered tissue 103 are not illustrated separately in the drawings because on the macro level, they combine to form a body of engineered tissue. A suitable engineered tissue 103 can be produced by incubating a cell-seeded scaffold in a bioreactor and applying mechanical loading to the developing engineered tissue according to the methods described in detail below. The engineered tissue 103 is sometimes referred to herein as a "functional engineered tissue" or "functional engineered cartilaginous tissue" because the engineered tissue has mechanical and chemical characteristics that allow it to function in vivo after implantation in a way similar to or the same as native cartilage.

The chondrocytes can be juvenile chondrocytes and/or adult chondrocytes. Juvenile chondrocytes are those obtained from an organism before ossification of the epiphyseal plates in the subchondral and metaphyseal bone.

Conversely, adult chondrocytes are those obtained from an organism after ossification of the epiphyseal plates. The chondrocytes can be autologous, or allogeneic. The chondrocytes can also consist of or include chondrocytes derived from stromal cells and/or stem cells that have been induced to exhibit the chondrocyte phenotype (e.g., by being subjected to mechanical loading and/or chondrogenic media). Further, the chondrocytes can also be accompanied by other living cells supported by the scaffold, including stromal cells, stem cells, and the like.

In addition to the scaffold and chondrocytes, the engineered tissue 103 suitably also includes an extracellular matrix (ECM) secreted by the chondrocytes. The ECM suitably has characteristics that are similar to the ECM of native cartilage. For example, the ECM is suitably rich in type II collagen and proteoglycans, such as glycosaminoglycan (GAG). For example, the engineered tissue suitably has a Type II collagen content in the range of about 2 to about 8 percent (w/w), more suitably in the range of about 4 to about 8 percent (w/w). Further, the engineered tissue can suitably have a Type II collagen content of about 4 percent (w/w) or more. The engineered tissue suitably has a GAG content in the range of about 4 to about 10 percent (w/w) and more suitably in the range of about 5 to about 8 percent (w/w). The engineered tissue 103 is also suitably functional to maintain an interstitial hydrodynamic pressure. Water is attracted to the feather-like polyanionic chains on the proteoglycan molecules, which are present in the engineered tissue in sufficient amounts to cause an osmotic swelling pressure. The high-tensile strength type II collagen forms a tight network of fibers arranged in a zonal architecture in which a surface layer of the bearing surface has a relatively higher concentration of collagen and a zone of tissue under the surface layer has a relatively lower concentration of collagen. The collagen fibers in the surface layer (which is sometimes referred to as surface tangential layer) are suitably oriented so a majority of the fibers are generally parallel to the surface of the articular bearing surface. The collagen works in opposition to the proteoglycan chains, resisting the swelling pressure and producing the load-bearing characteristics unique to cartilaginous tissue.

The zonal architecture characteristics of the engineered tissue 103 also include more than one characteristic phenotype of chondrocytes in native cartilage including spindyloid, round, or hypertrophic cells with pericellular, territorial, and/or interterritorial ECM such that collagen is primarily concentrated on the periphery and proteoglycan is primarily concentrated deeper in the engineered tissue 103.

Figure 31:
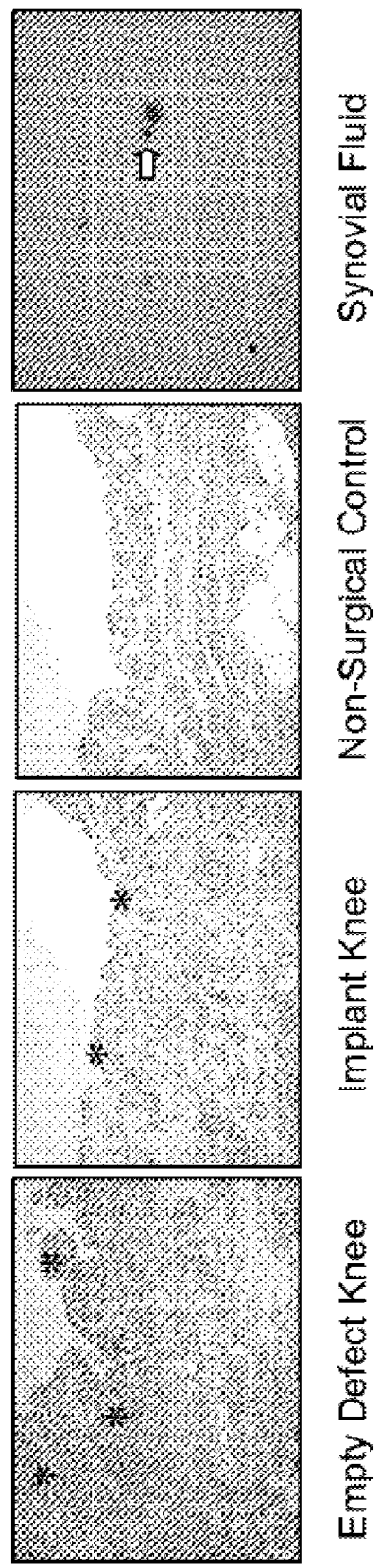
FIG. 31 shows representative histology (H&E) of synovium.
Figure 36:
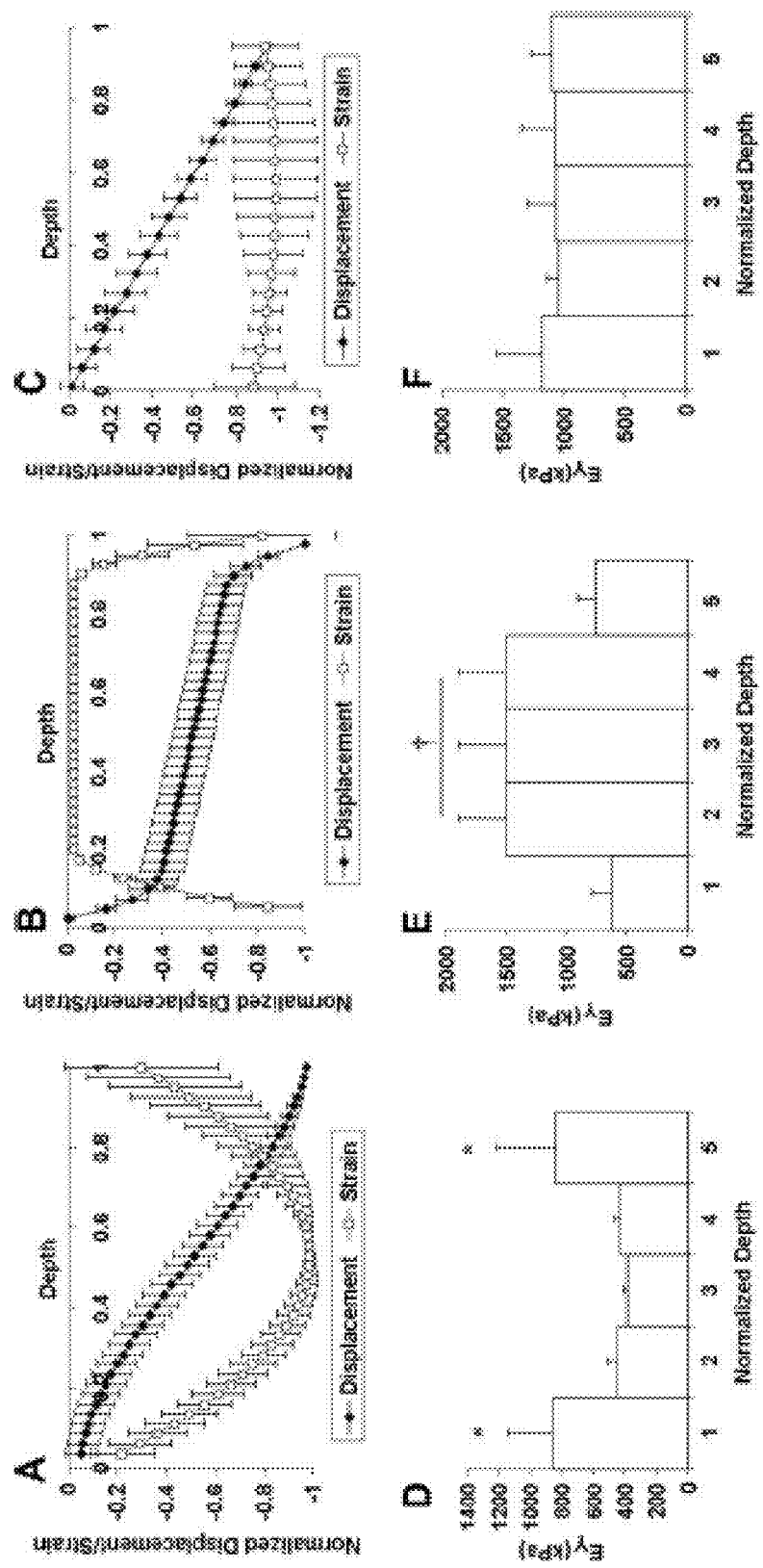
FIG. 36 includes graphical results of experiments.

The cell-seeded scaffold optionally includes one or more diffusion channels to enhance diffusion of nutrients into the scaffold, e.g., in the early stages of maturation. As illustrated in FIGS. 31 and 36, one or more diffusion channels extending at least partially or all the way through the cell-seeded scaffold can be created using a punch biopsy. The diameter of the diffusion channel is suitably selected so the diffusion channel remains open for a sufficient period to enhance diffusion of nutrients into the developing tissue during early maturation, but closes or at least begins to close via production of ECM filling the diffusion channel and/or infiltration of chondrocytes into the diffusion channel by the end of the maturation period.

Various materials can be used to make the scaffold. For example, a suitable scaffold can be made of an agarose hydrogel. However, other materials, including but not limited to alginate, polyethylene glycol, and other hydrogels, can be used within the scope of the invention.

The scaffold suitably has initial mechanical properties, porosity, and biocompatibility that is suitable for seeding the scaffold with cells and producing the engineered tissue according to the methods described below. The scaffold suitably has a hydraulic permeability in the range of about $2.8 \times 10^{-13}$ to about $3.2 \times 10^{-13}$ m$^4$/Ns. Preferably, the scaffold is able to bear and transfer loads to the surrounding tissue without being crushed. The scaffold preferably also has a porosity that allows for cell infiltration and nutrient transport. The scaffold is also preferably biocompatible to mitigate immunogenic issues while allowing engineered tissue to develop and maintain functional properties in vitro and in vivo.

As discussed in greater detail below, certain advantages can be obtained by applying mechanical loading to the cell-seeded scaffold/developing engineered tissue. Initially, it is the mechanical properties of the scaffold that dictate the nature of the mechanical loading that can be applied to the developing engineered tissue. In some cases it may be desirable to begin mechanical loading of the cell-seeded scaffold relatively early in the maturation process to expedite production of the ECM by the cells supported by the scaffold and reduce the amount of time needed to ready the developing engineered tissue for implantation. The scaffold suitably has the ability to withstand application of physiologic deformational loading (e.g., 10 percent peak-to-peak deformation from unconstrained compression at 1 Hz) without resulting in separation of the scaffold from a loading platen of a dynamic loading machine used to apply a load to the scaffold, without resulting in permanent deformation of the scaffold, and without requiring the cells seeded in the scaffold to first produce a matrix before the loading is applied. This allows the mechanical loading to begin shortly (e.g., substantially immediately) after the scaffold is seeded with cells. Further, the scaffold suitably exhibits a similar load-support mechanism as native articular cartilage. For example, the scaffold is suitably able to bear greater than 90% of an applied load via interstitial fluid pressurization. The scaffold also suitably promotes and/or maintains exhibition of the chondrocyte phenotypes by cells in the scaffold. The chondrocyte phenotypes are preferred because chondrocytes tend to produce more of the desirable type II collagen and cartilage specific proteoglycan, aggrecan, (which are desirable in the ECM of cartilaginous tissue for in vivo function) as opposed to other phenotypes such as fibroblasts which tend to produce other types of collagen and proteoglycan, which are less desirable than type II collagen in the ECM of cartilaginous tissue because they are associated with disease and/or dysfunction.

The gelable scaffold material is also suitably permeable to nutrients when in gel form. There are several measures of the permeability of a gelable scaffold material, including for example, the volume fraction of the pores (porosity), the hydraulic permeability to water based solutions, and the diffusion coefficient of solutes of various molecular weights. The gelable scaffold materials of the present invention suitably have an average porosity in the range of about 96 percent to about 99 percent and more suitably about 98 percent, when in gel form.

The hydraulic permeability of a gelable scaffold can be measured, for example, using a permeation device. In particular, the hydraulic permeability can be measured by perfusing a water-based electrolyte solution (such as physiological saline) through the scaffold and measuring the pressure difference across the scaffold at various perfusion flow rates. The gelable scaffold materials used herein suitably have a hydraulic permeability in the range of about $2.8 \times 10^{-13}$ to about $3.2 \times 10^{-13}$ m$^4$/N.s The diffusion coefficient of a gelable scaffold material can be measured, for example, by fluorescent recovery after photobleaching (FRAP). In particular, the diffusion coefficient can be measured by incubating the gelable scaffold material with fluorescein isothiocyanate (FITC)-conjugated dextran having a molecular weight representative of large growth factors or matrix products commonly used or produced during cell culture (e.g., about 70 kDa). The gelable scaffold material can then be exposed to a high intensity monochromatic laser to induce localized photobleaching, and the recovery of fluorophores can be monitored. The gelable scaffold materials used herein suitably have diffusion coefficients ranging from about 8 μm$^2$/second to about 50 μm$^2$/second, and more suitably in the range of about 19 μm$^2$/second to about 25 μm$^2$/second. The diffusion coefficient is a measure of how fast nutrients, growth factors, and other substances diffuse through the scaffold material.

One scaffold that includes all of the characteristics listed above can be made of a thermoreversible agarose hydrogel (e.g., a 2 percent agarose hydrogel). It is noted that the scaffold material is likely to degrade over time. However, in contrast to native cartilaginous tissue, there is at least some residual scaffold material present in the engineered tissue 103 produced and matured by the methods described below.

The scaffold can be shaped (e.g., molded as described below) so the engineered tissue has a bearing surface 105 that has substantially the same size and shape as at least a portion of the native articular bearing surface that is to be resurfaced, restored, or repaired by the implant 101. For example, the scaffold can be molded into a shape having a surface that replicates only a portion of an articular bearing surface for replacement of only a portion of the articular bearing surface (e.g., a circular disk or other plug used to repair focal defects in the articular bearing surface). As another example, the scaffold can be molded to produce a bearing surface that replicates an entire articular bearing surface for total resurfacing of the bearing surface. If desired, suitable molds can be produced in conjunction with magnetic resonance imaging (MRI) or other imaging technology in combination with CAD-based rapid prototyping technology to produce engineered tissue having a shape including a surface that replicates the bearing surface of a particular patient.

As illustrated in FIG. 1, the scaffold has been molded into a shape having a bearing surface 105 that replicates the bearing surfaces of a medial tibial plateau. Accordingly, the engineered tissue 103 also has a shape including a bearing surface 105 that replicates the shape of a medial tibial plateau. It is understood that the scaffold/engineered tissue 103 can have various different shapes within the scope of the invention, including without limitation a shape that replicates all or at least a portion of a native articular bearing surface associated with a patella; a trochlea or other surface associated with a saddle/condlyar joint (knee, stifle, ankle, hock, elbow); or a femoral or humeral head (or other surface associated with a ball and socket joint).

The engineered tissue 103 has characteristics that are substantially similar to or which exceed those of native cartilage. For example, the equilibrium Young's modulus is suitably at least about 150 kPa, more suitably in the range of about 150 kPa to about 1500 kPa, more suitably in the range of about 185 kPa to about 1300 kPa, still more suitably in the range of about 275 kPa to about 1300 kPa, and more suitably in the range of about 800 kPa to about 1300 kPa. As those knowledgeable of the properties of cartilaginous tissue know, the strain in cartilaginous tissue in response to a compression load will vary over time as fluid moves through the tissue in response to the load. Equilibrium Young's modulus is based on the amount of strain after the strain produced by the load has become substantially constant. Engineered tissue having these characteristics can be produced according to methods described in greater detail below.

The size of the body of engineered tissue 103 can vary depending on the amount of articular cartilage that is to be replaced by the implant. Using the methods described below, it is possible to make a significant amount of engineered tissue 103 having the mechanical and chemical properties described herein in a relatively short period of time. For example, the engineered tissue suitably has a total surface area in the range of about 0.05 $cm^2$ to about 50 $cm^2$, more suitably in the range of about 0.5 $cm^2$ to about 50 $cm^2$, more suitably in the range of about 1 $cm^2$ to about 50 $cm^2$, more suitably in the range of about 1 $cm^2$ to about 25 $cm^2$, more suitably in the range of about 1 $cm^2$ to about 12 $cm^2$, and more suitably in the range of about 5 $cm^2$ to about 12 $cm^2$. The engineered tissue suitably has a volume in the range of about 0.005 ml to about 80 ml, more suitably in the range of about 1 ml to about 80 ml, more suitably in the range of about 1 ml to about 25 ml, and still more suitably in the range of about 1 ml to about 10 ml. In the case of a plug type implant, for example, the volume can be in the range of about 0.005 ml to about 1.15 ml. In the case of an anatomically shaped implant for resurfacing a joint, the volume can be in the range of about 0.005 ml to about 25 ml. The engineered tissue suitably has a thickness in the range of about 0.1 mm to about 25 mm, more suitably in the range of about 1 mm to about 20 mm, and more suitably in the range of about 1 mm to about 10 mm, and still more suitably in the range of about 4 mm to about 10 mm.

The implant can be combined with other implants (e.g., a bone graft to make an osteochondral implant) during or prior to surgical restoration of an articular joint to replace or augment native cartilage in the joint. However, it is also contemplated, that the implant can be affixed directly to a native biological structure associated with an articular joint (e.g., native bone and/or native cartilage) using any suitable surgical techniques and without using any other implants within the scope of the invention.

Osteochondral Implants

Although the chondral implant 101 described above can be suitable for some applications, advantages can be obtained in some cases by making an osteochondral implant including the engineered tissue 103 described above as the chondral portion of the implant and, as the osteo portion of the implant, a biocompatible porous substrate secured to the engineered tissue and suitable for attaching the engineered tissue to native bone associated with the articular joint. As noted above, cartilage heals poorly. This presents a further challenge to cartilage repair as the absence of healing response between the engineered tissue 103 and the adjacent native cartilage can result in poor graft-host integration. To facilitate integration of the engineered tissue 103 with native tissue, transplantation of the engineered tissue can be performed with an underlying segment of bone or a suitable non-biological porous substrate that acts as an anchor and secures the implant to the underlying bone. Using an osteochondral implant capitalizes on the ability for bone to heal well. Additionally, injuries that penetrate the subchondral bone (as would be the case during surgical implantation of an osteochondral implant) illicit a temporary cartilage repair response that involves cell migration from the bone marrow, fibrin clot formation, and associated vascular ingrowth.

Figure 2:
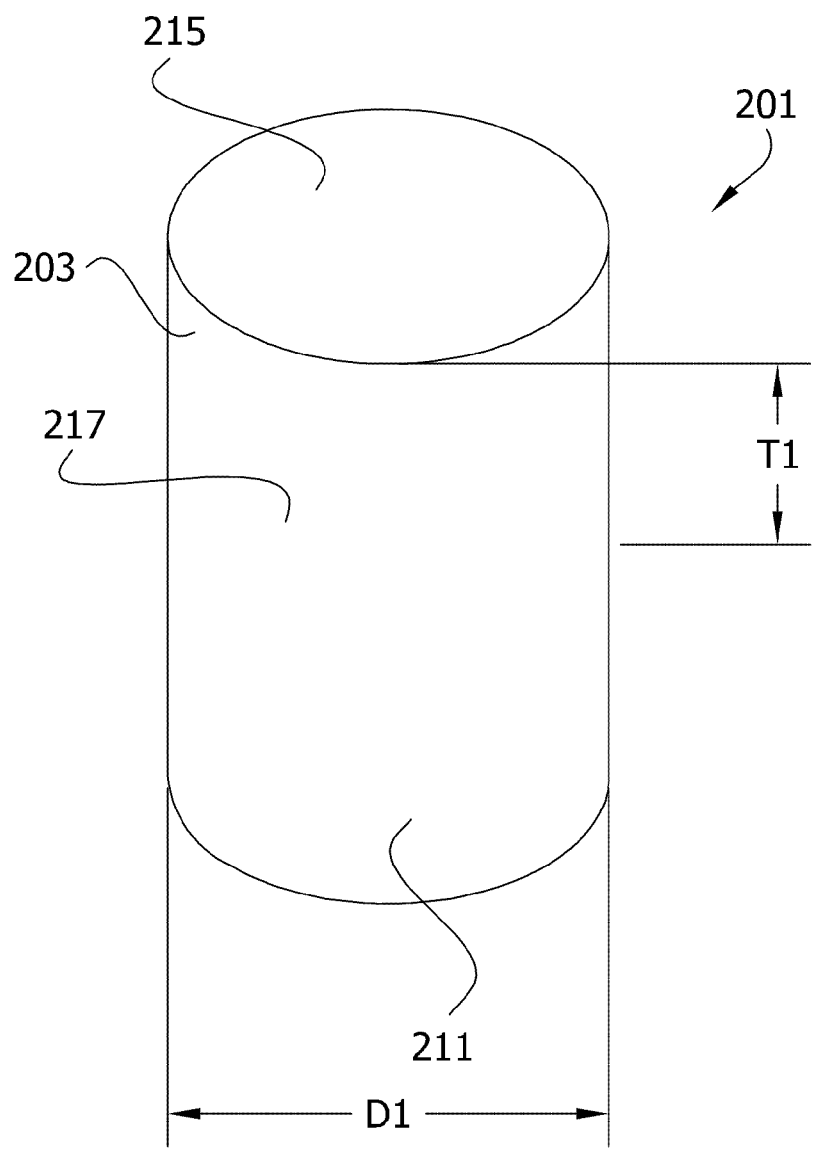
FIG. 2 is a perspective of one embodiment of an osteochondral implant.

One embodiment of an osteochondral implant 201 is illustrated in FIG. 2. The implant 201 includes a functional engineered cartilaginous tissue 203, which is suitably identical to the engineered tissue 103 of the chondral implant 101 described above. The engineered tissue 203 is secured to a porous substrate 211 suitable for use as a bone graft. For example, the porous substrate 211 suitably has an open celled porous structure including a plurality of interconnected voids and the engineered tissue 203 suitably extends from exterior of the substrate 211 into the pores to secure the substrate to the engineered tissue. One way to achieve this is to contact the cell-seeded scaffold with the porous substrate 211 while the scaffold material is liquid to allow the scaffold material to flow into the pores. For example, the liquid is suitably allowed to saturate the pores of an interface layer of the porous substrate 211 having an average thickness in the range of about 0.5 mm to about 20 mm, more suitably in the range of about 0.5 mm to about 10 mm, more suitably in the range of about 0.5 mm to about 4 mm, and still more suitably in the range of about 0.5 mm to about 1 mm. (e.g., about 2 mm) while the pores outside the interface layer are substantially free of the scaffold material. Generally, it is desirable to have a relatively thin interface layer to encourage native cells to colonize the porous substrate and to minimize the number of chondrocytes in the porous substrate. It can be difficult to produce a thin interface layer when the substrate 211 is shaped to correspond to the entire articular bearing surface (for total joint resurfacing). The thickness of the interface layer for anatomically shaped implants is suitably in the range of about 2 mm to about 20 mm.

When the scaffold material saturating the pores of the interface layer sets up as a gel, the cell-seeded scaffold is secured to the porous substrate. The porous substrate 211 remains secured to the cell-seeded scaffold as it matures into the engineered tissue 203. It is understood, however, that the engineered tissue 203 can be secured to the porous substrate 211 in other ways (such as an adhesive, interdigitated design of components, and/or direct mechanical fixation) within the scope of the invention. Also, the porous substrate 211 can be secured to the engineered tissue 203 after it has been matured within the scope of the invention.

Various materials can be used as the porous substrate 211 for the osteochondral implant 201 within the scope of the invention. The porous substrate 211 is suitably made of a material having properties that do not change over time in culture. The porous substrate 211 suitably has an open porous structure that facilitates securing the bone to gelling chondrocyte-laden agarose or other hydrogels that may be used as the scaffold to produce the engineered tissue. The porous substrate is also suitably biocompatible. The porous substrate can be osteoinductive and/or osteoconducive. The porous substrate is also suitably made of a material that can be readily configured to have anatomic size, shape, and geometry such that the substrate can be implanted and secured to the recipient's bone using standard surgical techniques.

In the implant 201 illustrated in FIG. 2, the porous substrate 211 is devitalized trabecular bone. The trabecular bone can be autologous or allogeneic. Trabecular bone is abundantly available and easily shaped into a multitude of forms without expensive equipment. Devitalized and demineralized bone is already FDA approved and used clinically as a scaffold to promote bone growth. Devitalized and demineralized bone is also a source of osteoinductive factors that may facilitate integration of the osteo portion of the implant with bone that is native to the articular joint.

The implant 201 illustrated in FIG. 2 is a plug type implant that is suitable for repair/restoration of a focal defect in an articular bearing surface. The implant is designed to be press-fit into pre-drilled cavities in the damaged joint during surgery, thereby replacing a portion of the articular cartilage bearing surface while anchoring to the bone below. The engineered tissue 103 is suitably generally cylindrical. For example, the engineered tissue is suitably produced by maturation of a cell-seeded scaffold that is substantially cylindrical. Although the engineered tissue 103 is cylindrical in FIG. 2, it is recognized that the shape of the engineered tissue can evolve (e.g., into a frusto-conical shape) in the maturation process and that it may be difficult to precisely control the shape of the matured engineered tissue. The average diameter D1 of the engineered tissue is suitably in the range of about 6 mm to about 20 mm. The thickness T1 of the engineered tissue 103 will varying depending on the joint involved and the size of the human or animal patient or subject that will receive the implant. For example, in canines, the Thickness T1 will usually be in the rage of about 0.1 mm to about 1 mm. For humans, the thickness T1 of the engineered tissue 103 will usually be in the range of about 1 mm to about 10 mm. The porous substrate 211 of this plug-type implant 201 is also substantially cylindrical (or prismatic) and has a cross-sectional area that is about the same as that of the engineered tissue.

The scaffold for the engineered tissue 103 for the implant 201 is suitably substantially identical to the scaffold described above for the chondral implant 101 above. For example, the scaffold can be made of the same agarose hydrogel described above. Other scaffold materials described above can also be used within the scope of the invention. In addition to the factors that impact selection of a scaffold material for the chondral only implant 101, the scaffold material should also be selected to provide a sufficient interface strength between the chondral and osteo portions of the implant 201 to withstand the shear forces that will be encountered at the articular joint.

As illustrated in FIG. 2, the surface of the porous substrate 211 that is secured to the engineered tissue can suitably include irregularities (i.e., be non-planar) to enhance the strength of the interface between the engineered tissue 103 and the porous substrate 211.

Figure 3:
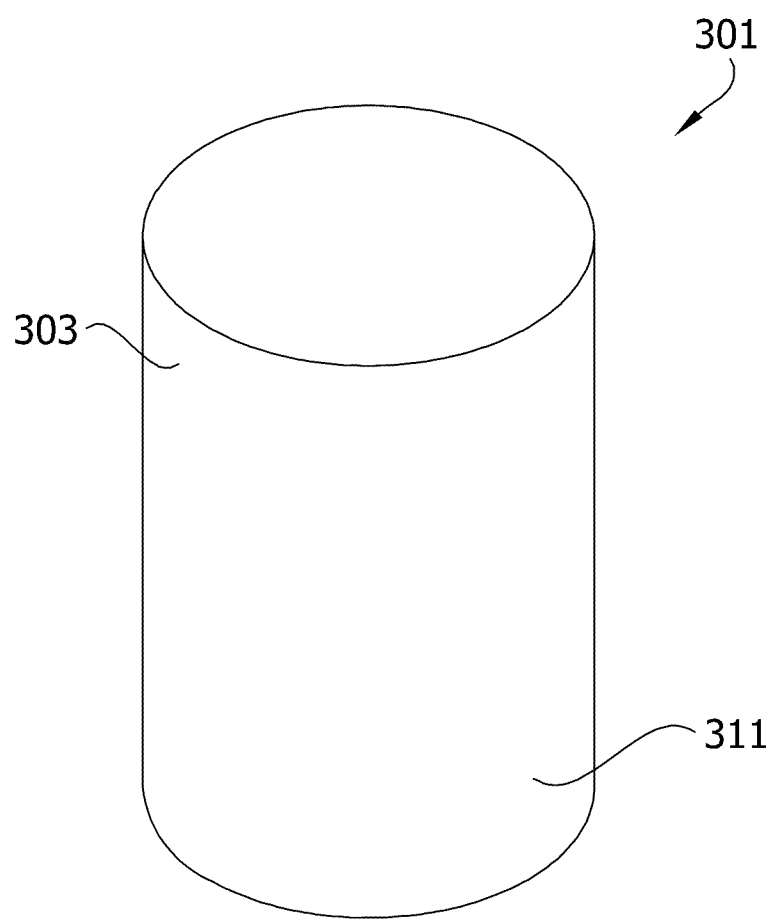
FIG. 3 is a perspective of second embodiment of an osteochondral implant.

Another embodiment of an osteochondral implant 301 is illustrated in FIG. 3. This implant 301 is a plug-type implant and is suitably substantially identical to the implant 201 described above and illustrated in FIG. 2, except as noted. One significant difference between the implant 301 illustrated in FIG. 3 and the implant 201 described above is that the implant 301 has a porous substrate 311 that is substantially free of trabecular bone.

The inventors have found that chondrocyte-seeded agarose hydrogel constructs cultured alone or attached to an underlying bony base in a chemically defined medium formulation yields engineered cartilaginous tissue with native Young's modulus ($E_Y$) and glycosaminoglycan (GAG) content. By day 42 in culture the incorporation of a bony base significantly reduced these properties ($E_Y$=87±12 kPa, GAG=1.9±0.8% w/w) compared to the gel-alone group ($E_Y$=642±97 kPa, GAG=4.6±1.4% w/w). The mechanical and biochemical properties of chondrocyte-seeded agarose constructs were inhibited when co-cultured adjacent to bone (unattached). It is believed that that soluble factors rather than direct cell-bone interactions mediate the chondro-inhibitory bone effects. Altering the method of bone preparation, including demineralization, or the timing of bone introduction in co-culture did not ameliorate the effects. In contrast, osteochondral constructs with native cartilage properties ($E_Y$=730±65 kPa, GAG=5.2±0.9% w/w) were achieved when a porous tantalum metal base material was adopted instead of bone. (Example 1 below).

In particular, the substrate 311 of the embodiment illustrated in FIG. 3 is suitably substantially free of trabecular bone. For example, the substrate 311 can suitably be a biocompatible metal, a synthetic polymer (polycaprolactone, poly-l-lactic acid, polyglycolic acid, and the like) and/or other biologic material (collagen, hydroxyapatite, etc.) that is suitable for implantation in a recipient organism. One particularly desirable non-biological substrate material is a porous tantalum substrate. Tantalum is osteo- and chondroinductive and can therefore promote integration between the two graft halves in culture as well as development of the subchondral plate after implantation. A porous tantalum substrate can also be produced in substantially any desired shape, for example using wire cut electron discharge machining to maintain porosity. A suitable porous tantalum substrate can be obtained from Zimmer, Inc.

Figure 4A:
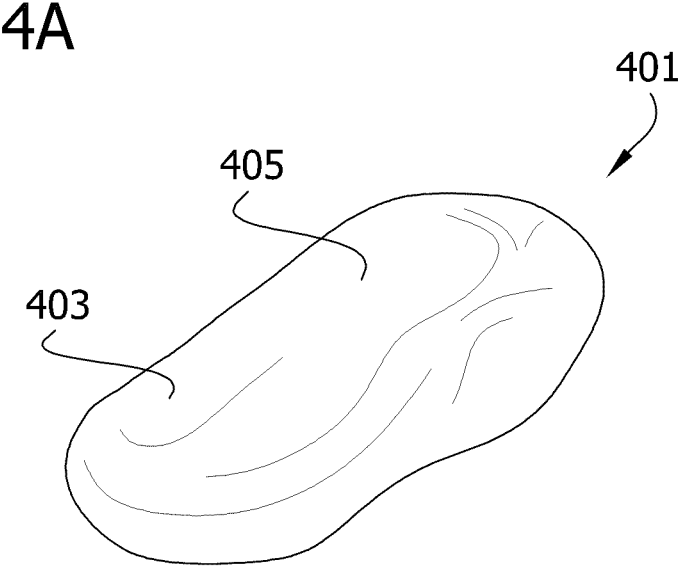
FIG. 4A is a perspective of third embodiment of an osteochondral implant.
Figure 4B:
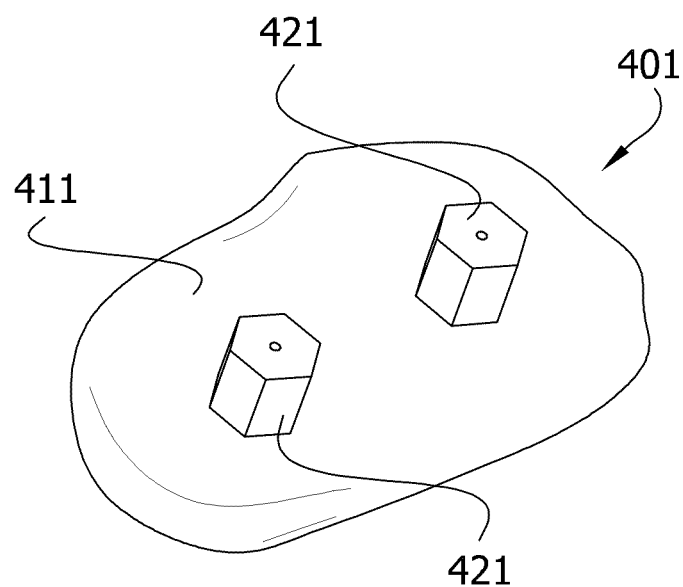
FIG. 4B is another perspective of the osteochondral implant illustrated in FIG. 4B from a different vantage point.

Another osteochondral implant 401 is illustrated in FIGS. 4A and 4B. This implant 401 is substantially identical to the implant 201, except as noted. The implant 401 is not a plug type implant. Instead, the implant 401 includes engineered tissue 403 that has a bearing surface 405 designed to completely replace a native articular bearing surface. For example, the implant 401 illustrated in FIGS. 4A and 4B is configured for complete resurfacing of a canine patella. It is understood that similar implants can be used for complete resurfacing of other articular bearing surfaces. Compared to the plug type implants 201, 301, the total resurfacing implant 401 may include a larger volume of engineered tissue 403. For example, the volume, surface area, and other size related parameters of the engineered tissue 403 in the implant 401 can suitably be the same values set forth above in the description of the corresponding parameters for the engineered tissue 103 of the chondral only implant 101. The engineered tissue 403 can suitably be combined with any porous substrate described above for the implants 201, 301 (including trabecular bone, tantalum, and synthetic polymers) within the scope of the invention. In the embodiment illustrated in FIG. 4B, the porous substrate 411 is made of tantalum and has been machined to have at least one peg (e.g., two pegs as illustrated) sized and shaped to be inserted in a pre-drilled cavity (not shown) in the recipient's subchondral bone during surgical implantation of the implant 401.

Methods for Making Chondral and Osteochondral Implants

Also within the scope of the present invention are methods for producing functional cartilaginous tissue, including methods for making the chondral and osteochondral implants described above. These methods generally include making a cell-seeded scaffold including a plurality of living chondrocytes and a gelable scaffold material, and culturing the cell-seeded scaffold (the gelable scaffold material and chondrocytes) in a medium comprising transforming growth factor-beta (TGF-beta). The culturing is suitably performed in a bioreactor, wherein mechanical loading is applied to the cell-seeded scaffold according to the methods described in detail below.

Method of Making the Cell-Seeded Scaffold

Methods for making the cell-seeded scaffold are also included within the scope of the present invention. The methods for making the cell-seeded scaffolds of the present invention generally include suspending a plurality of living chondrocytes in a gelable scaffold material, and forming the cell-seeded scaffold by shaping the living chondrocytes and gelable scaffold material into a desired shape. In some embodiments, the cell-seeded scaffold is combined with a porous substrate as described above.

As noted above, the living chondrocytes which are incorporated into the cell-seeded scaffolds of the present invention can be juvenile (i.e., immature) and/or adult (i.e., mature) chondrocytes. The chondrocytes are suitably primary chondrocytes or chondrocytes which have been subjected to limited expansion (passaging) in cell culture. Thus, to obtain the chondrocytes, cartilage is suitably harvested from a joint of a human or animal subject and the chondrocytes are isolated from the surrounding extracellular matrix (ECM). The chondrocytes can be chondrocytes from an autologous donor or an allogeneic donor.

In one embodiment, the chondrocytes may suitably be isolated from the surrounding ECM by digesting away the collagen with a collagenase (e.g., collagenase type VI) and separating the chondrocytes from the digested collagen, e.g. by filtering the suspension of digested collagen and chondrocytes. The chondrocytes may then suitably be concentrated (for example by centrifugation), counted (for example, using a hemocytometer), and resuspended in a physiologically compatible buffer to create a cell suspension having a suitable concentration of chondrocytes. In some embodiments, other types of living cells may also be added to the cell suspension, for example, stromal cells, stem cells, and the like. Suitable concentrations of chondrocytes in the cell suspension range from about 20 million cells/ml to about 400 million cells/ml. In some embodiments, the concentration of chondrocytes in the cell suspension is suitably about 30 million cells/ml to about 200 million cells/ml. In other embodiments, the concentration of chondrocytes in the cell suspension is about 60 million cells/ml.

If primary chondrocytes are to be used to make the implant, the isolated primary chondrocytes (with or without additional types of living cells) are suitably suspended in a gelable scaffold material. In one embodiment, a volume of the cell suspension is suitably mixed with a gelable scaffold material.

In some embodiments, in order to increase the number of chondrocytes available for incorporation into the cell-seeded scaffold, the primary chondrocytes can be subjected to limited expansion (passaging) in cell culture prior to being mixed with the gelable scaffold material. Passaging the chondrocytes is advantageous where the amount of cartilage which can be obtained is limited, for example where the cartilage is obtained from a living human subject. Furthermore, passaging has been found to be particularly suitable when the chondrocytes are adult chondrocytes. Following isolation of the chondrocytes from the cartilage of a human or animal subject, the chondrocytes are suitably plated in tissue culture dishes, tissue culture flasks, or the like, and grown at 37° C., 5% $CO_2$ until substantially confluent. The chondrocytes are suitably cultured in Dulbecco's Modified Eagle Medium (DMEM) in the presence of serum and one or more growth factors, for example, TGF-beta, fibroblast growth factor (FGF), and platelet-derived growth factor (PDGF). The serum is suitably FBS, the TGF-beta is suitably TGF-beta1 or TGF-beta3, the FGF is suitably FGF-2 and the PDGF is suitably PDGF-BB. In one embodiment, the chondrocytes are suitably cultured in DMEM containing fetal bovine serum (FBS), about 0.1 ng/ml to about 10 ng/ml TGF-beta1 or TGF-beta3, about 0.5 ng/ml to about 50 ng/ml FGF-2 and about 1 ng/ml to about 100 ng/ml PDGF-BB. In another embodiment, the chondrocytes are suitably cultured in DMEM containing FBS, about 1 ng/ml TGF-beta, about 5 ng/ml FGF-2, and about 10 ng/ml PDGF-BB. Once the chondrocytes are substantially confluent, they are removed from the tissue culture plate (e.g., using trypsin or the like) and replated into two or more tissue culture dishes, flasks, or the like. The chondrocytes are again cultured in DMEM containing serum and growth factors described as described above until the chondrocytes reach substantial confluency. The replating can be repeated, and replating counts as one passage.

Persons having ordinary skill in the art will recognize that the number of passages to which the chondrocytes can be subjected will be limited by the tendency of the chondrocytes to become undifferentiated during passaging. The skilled artisan will also recognize that some level of de-differentiation during passaging is acceptable within the scope of the present invention, so long as the chondrocytes are capable of returning to a substantially differentiated state once incorporated into the cell-seeded scaffold and cultured in the presence of TGF-beta. The number of passages will therefore suitably be limited to a number of passages where although some de-differentiation may occur, the chondrocytes substantially return to their differentiated state once incorporated into the cell-seeded scaffold and cultured in the presence of TGF-beta, suitably in a bioreactor wherein mechanical loading is applied to the cell-seeded scaffold according to the methods described below. For example, the chondrocytes are suitably passaged for fewer than about five passages, and more suitably for fewer than about three passages. Following passaging, the chondrocytes are suitably removed from the tissue culture plate and suspended in a physiologically compatible buffer to create a cell suspension having a suitable concentration of chondrocytes, as described above, and the cell suspension is suitably mixed with a gelable scaffold material.

The gelable scaffold material is suitably an agarose hydrogel material. However, as noted above, other materials, including but not limited to alginate and various synthetic and natural (e.g., collagen, hyaluronan) hydrogels, can be used within the scope of the invention. When the gelable scaffold material is a thermoreversible gelable scaffold material, the gelable scaffold material suitably gels at a temperature at which the viability and health of the cells will not be substantially detrimentally affected during the time it takes the gelable scaffold material to gel. For example, the gelable scaffold material suitably has a gel point of about 4° C. to about 38° C. When the gelable scaffold material is thermoreversible gelable scaffold material, the gelable scaffold material also suitably has a low melting point. For example, when the gelable scaffold material is agarose, the agarose is suitably a low melt agarose, for example Sigma agarose Type VII (having a gel point of 26° C.±2.0° C. at 1.5% and a melting temperature of ≤65° C.) or Sigma agarose Type IX (having a gel point of 8-17° C. at 0.8% and a melting temperature of ≤50° C.).

In one embodiment of the method of making the cell-seeded scaffold, a volume of the cell suspension is mixed with an approximately equal volume of about 2% to about 6% agarose, to yield a final agarose concentration of about 1% to about 3%. In addition, mixing the volume of the cell suspension with the gelable scaffold material will suitably yield a chondrocyte concentration in the cell suspension/gelable scaffold material suspension of about 10 million cells/ml to about 200 million cells/ml. More suitably, the mixing will yield a chondrocyte concentration of about 10 million cells/ml to about 60 million cells/ml. For example, in some embodiments, a volume of a cell suspension having a chondrocyte concentration of 60 million cells/ml is mixed with an approximately equal volume of 4% low-melt agarose at 37° C. to yield a chondrocyte concentration of 30 million cells/ml and an agarose concentration of 2%.

Casting/Molding the Cell-seeded Scaffold

Once the plurality of living chondrocytes have been suspended in the gelable scaffold material, the cell-seeded scaffold can be formed by shaping the suspension of living chondrocytes and gelable scaffold material into a desired shape.

In one embodiment of a method for shaping the living chondrocytes and gelable scaffold material into a desired shape, the suspension of chondrocytes and gelable scaffold material is suitably casted or molded into one or more slabs. One or more bodies can then suitably be excised from the one of more slabs. The bodies suitably each have an average thickness of about 0.1 mm to about 10 mm (e.g., about 0.5 mm to about 6 mm). In some embodiments, the bodies are disks having substantially circular cross-sections and have average diameters in the range of about 3 mm to about 20 mm (e.g., about 4 mm to about 10 mm). For example, a chondrocyte/agarose suspension can be cast into slabs and cored using a sterile disposable punch to final dimensions of about 3 mm to about 4 mm (diameter) by about 2.3 mm (thickness).

Another embodiment of a method for shaping the scaffold/engineered tissue 103, 203, 303, 403 into a desired shape and combining the scaffold/engineered tissue with a porous substrate 211, 311, 411 is illustrated in FIGS. 5A-5G. The method uses a casting/molding system to shape the mixture of cells and gelable scaffold material into the shape of the cell-seeded scaffold/engineered tissue.

Figure 5B:
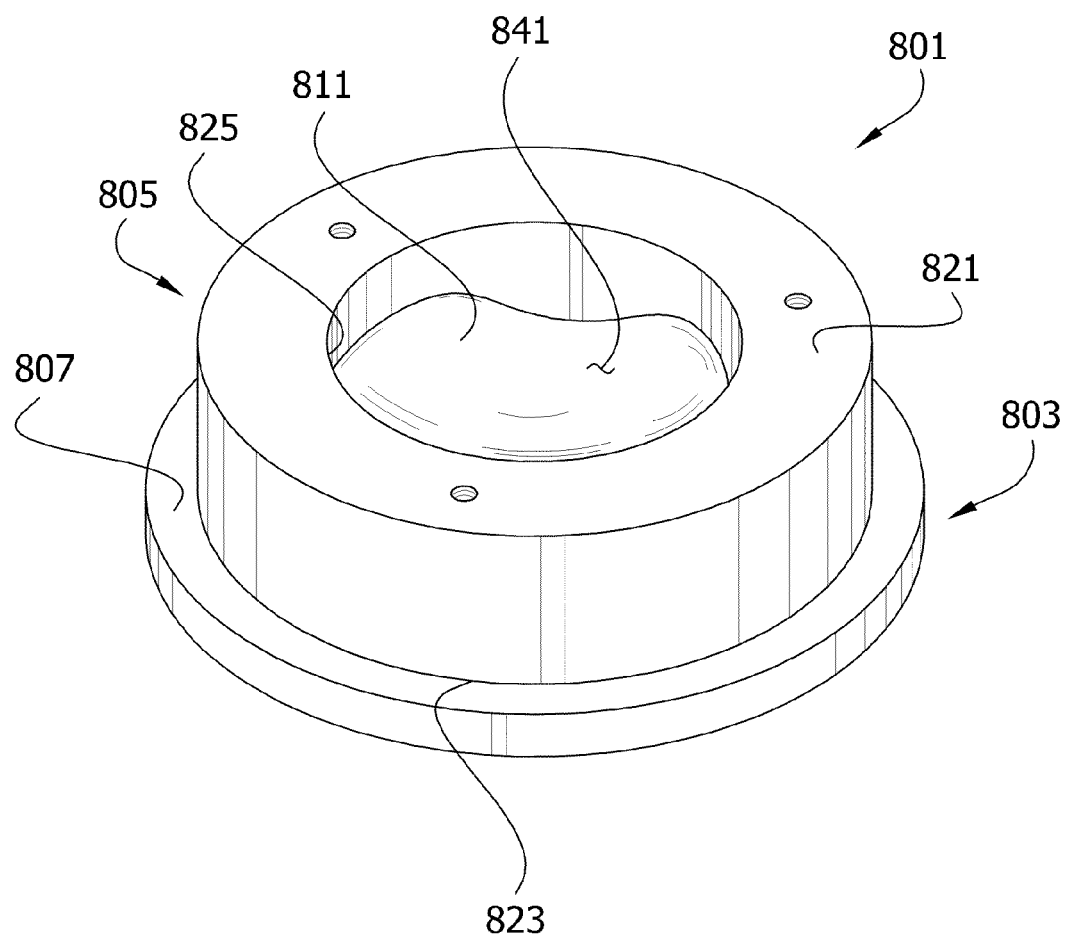

One embodiment of a molding system uses a mold 801 (FIG. 5A) that includes a mold base 803 and a retainer 805. The retainer 805 is suitably a separate piece that can be releasably secured to the mold base 803 (e.g., using bolts 806 or other suitable fasteners), as illustrated in FIGS. 5A-5B. However, the mold base and retainer can be a single unitary structure within the scope of the invention. The mold 801 can be used to make a chondral only implant or an osteochondral implant. Further, molds as described herein can be used to make implants designed to replace only a portion of an articular cartilage bearing surface or for complete resurfacing of an articular cartilage bearing surface.

The mold base 803 suitably includes a plate 807 and a projection 809 extending from the plate. The projection 809 suitably extends up from a central portion of the plate 807 so the plate forms a shoulder extending circumferentially around the projection. The retainer 805 includes a circumferential sidewall 821 having an inner surface 825 that forms an opening 831 extending through the retainer from the top to the bottom. The opening 831 is sized and shaped to receive the projection 809 when the bottom 823 of the retainer is placed on the shoulder 807 of the mold base 803. The projection 809 suitably has a side surface 827 sized and shaped to conform to the inner surface 825 of the retainer sidewall 821. If desired, a gasket or other seal (not shown) can be positioned between the inner surface 825 of the retainer sidewall 821 and the side surface 827 of the projection and/or between the bottom 823 of the retainer 805 and the shoulder 807 of the mold base to form a fluid-tight seal between the mold base and the retainer.

When the mold base 803 and retainer 805 are secured together with the bottom 823 of the retainer on the shoulder 807 of the mold base as illustrated in FIG. 5B, a mold cavity 841 is formed by the upper portion of the inner surface 825 of the retainer sidewall 821 and the upper surface 811 of the projection 809 on the mold base.

The upper surface 811 of the projection 809 suitably has a shape designed to produce the articular bearing surface of the cell-seeded scaffold/engineered tissue. For example, the shape of the projection 809 at its upper surface 811 is suitably a negative of the articular bearing surface. The shape of the projection 809 at the upper surface 811 can be customized for a particular recipient. For example, digitized anatomical data from an MRI or other imaging system can be used in combination with a CAD-based rapid prototype system to create a mold base 803 in which the projection 809 (including the shape of the upper surface 811) is customized to account for the recipient's anatomy and thereby facilitate implantation of the resulting implant in the recipient. Alternatively, the mold base 803 can be selected from a set of standardized mold bases designed to produce implants having various standardized sizes and shapes that are suitable for commonly performed procedures. Because the mold base 803 and retainer 805 illustrated in FIGS. 5A and 5B are separable, the retainer can be used with any of various interchangeable mold bases (e.g., from a set of mold bases that are substantially identical except for the shape of the upper surface of their respective projections).

Figure 5C:
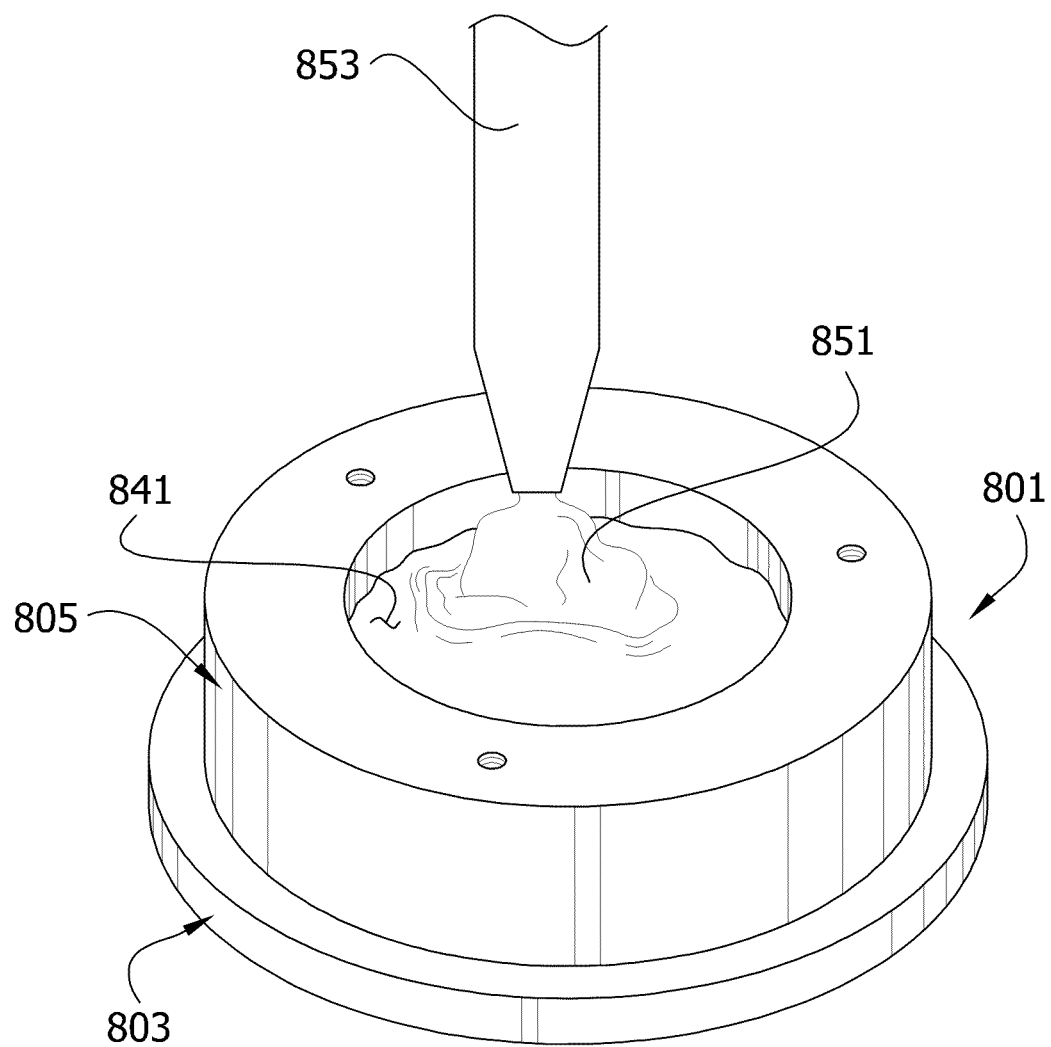

To use the mold 801, the retainer 805 is secured to a mold base 803 having a projection 809 defining an appropriately shaped upper surface 811 to form a mold cavity 841 that is shaped to produce the desired implant. Then a mixture 851 of cells and gelable scaffold material (e.g., produced as described above) is dispensed into the mold cavity 841. For example, the mixture 851 can be dispensed in the mold 841 cavity using a pipette 853 or other suitable device, as illustrated in FIG. 5C. Before the gelable material has set, a porous substrate 871 (which can be made of any of the materials described above, including but not limited to trabecular bone, other biological materials, tantalum, gold, titanium, and synthetic polymers) is pressed into or partially immersed in the mixture 851.

Figure 5D:
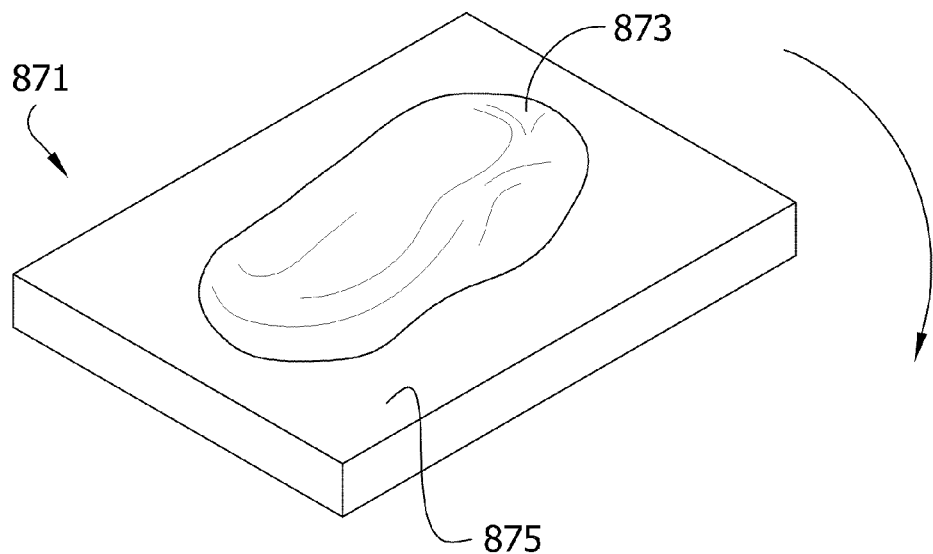
Figure 5D:
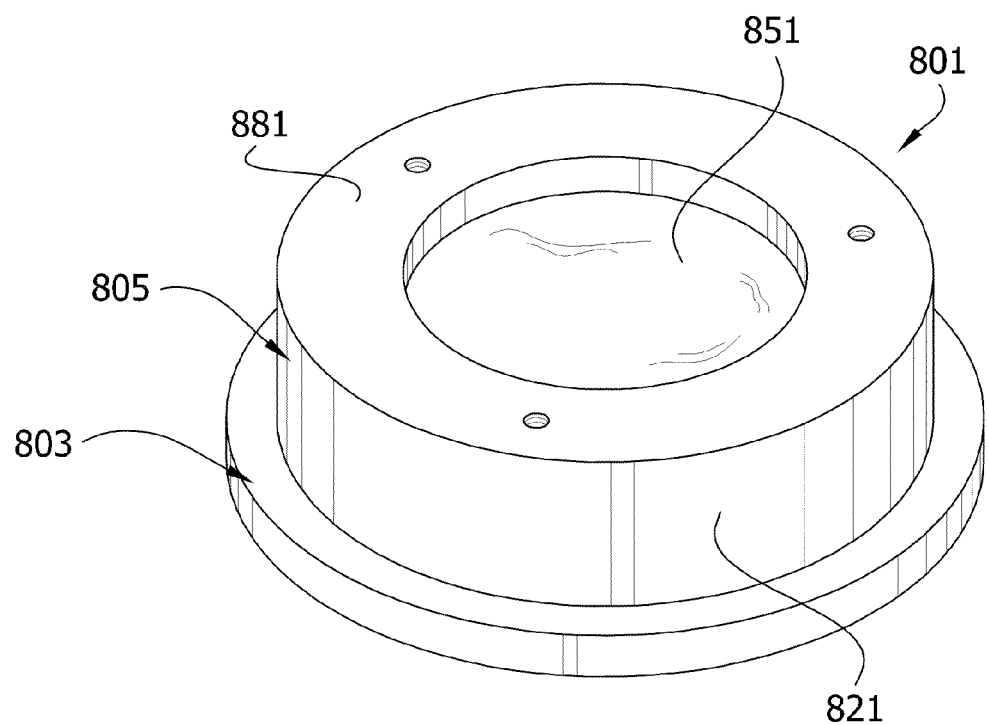
Figure 5E:
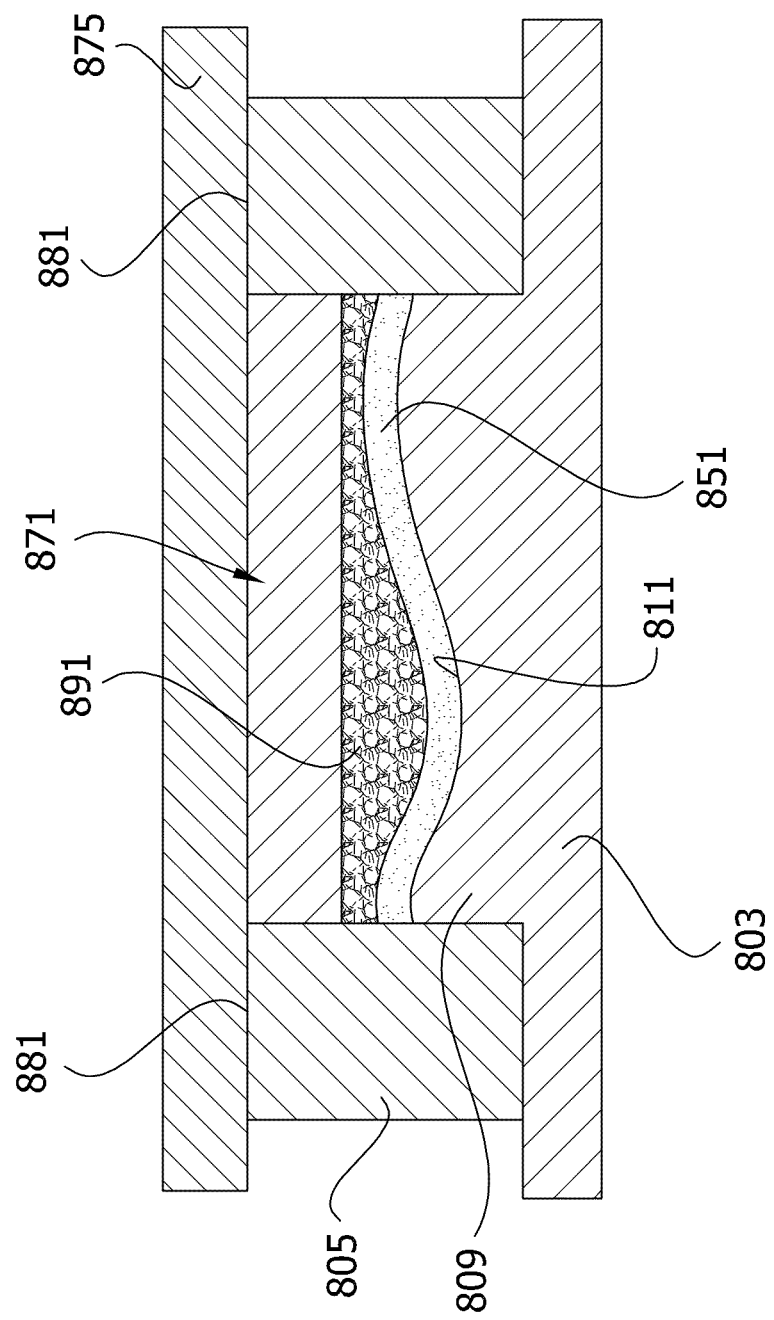
Figure 5F:
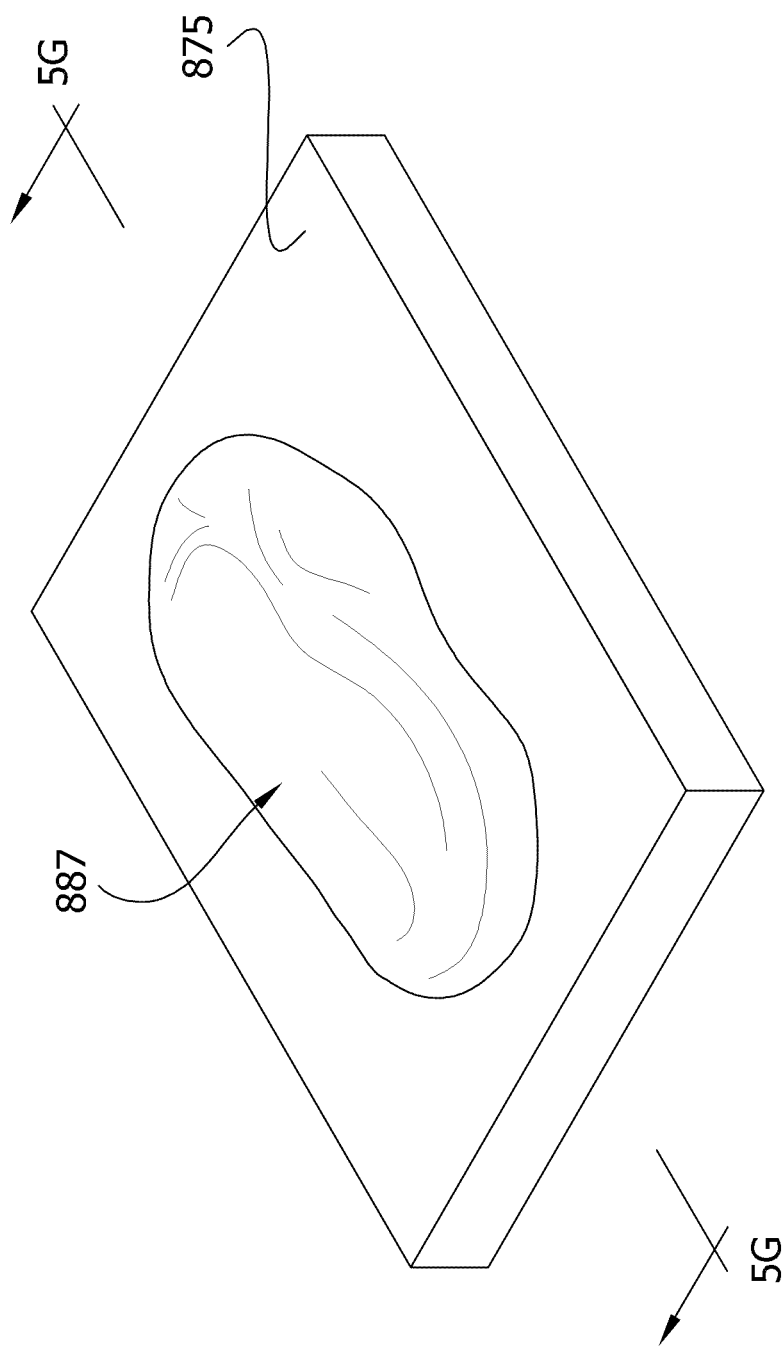
Figure 5G:
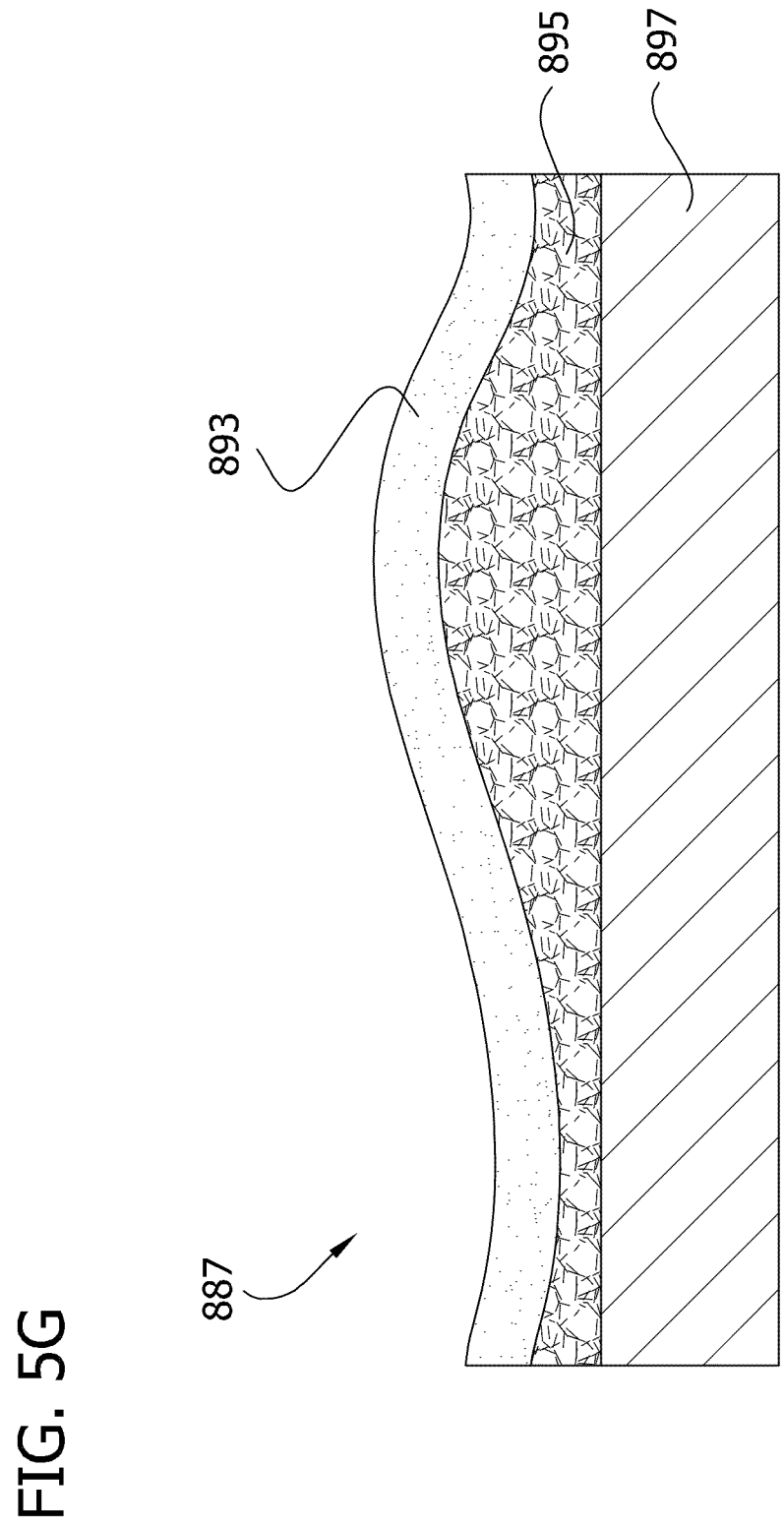

As illustrated in FIG. 5D, the porous substrate suitably includes a shaped portion 873 having a surface shaped to correspond to the desired shape of the porous substrate that will underlie the chondral portion of the implant and a temporary retaining portion 875 operable limit the extent to which the shaped portion 873 can be pressed into the mold cavity 841 to control the depth to which the shaped portion of the substrate 871 is pressed into the gelable mixture 851 (FIG. 5E). The temporary retaining portion 875 can a separate backing material secured to the shaped 873 porous substrate (e.g., with adhesive or any other suitable means), as illustrated. In this case the entire porous substrate can comprise the shaped portion 873. Alternatively, the porous substrate can be shaped to have a temporary retaining portion integral with the shaped portion, in which case the temporary retaining portion is removed after casting. The shaped portion 873 can be produced using a computer controlled machining process and digitized data from an anatomical model having the desired shape.

For example, if the porous substrate 871 is made of tantalum, computer controlled wire electrical discharge machining can be used to shape the porous tantalum substrate while maintaining the porous structure of the tantalum. Virtually any shape that would be needed for a tantalum porous substrate of an osteochondral implant can be obtained from Zimmer, Inc. of Warsaw, Ind., which sells a suitable tantalum substrate as Trabecular Metal™.

The gelable mixture 851 penetrates a portion of the porous substrate 871 creating a layer 891 of substrate that is saturated with the gelable mixture. The gelable material is allowed to set up in the mold 801. The result is a multilayer construct 887 including a cell-seeded scaffold only layer 893, a scaffold-porous substrate interface layer 895, and a substrate only layer 897. The shape of the mold cavity 841, the shaped portion 873 of the porous substrate 871, and the temporary retaining portion 875 of the porous substrate are suitably selected so the cell-seeded scaffold layer 993 has a thickness in the range of about 0.1 mm to about 10 mm (e.g., about 2 mm), the interface layer 995 has a thickness in the range of about 0.1 mm to about 10 mm (e.g., about 2 mm), and the porous substrate layer has a thickness in the range of about 0.2 mm to about 40 mm (e.g., about 2 mm).

Then the construct 887 is placed in a bioreactor to allow the cell-seeded scaffold to develop into the engineered tissue through maturation, as described in more detail below.

Method of Culturing the Cell-seeded Scaffold in a Bioreactor

The cell-seeded scaffold (the gelable scaffold material and living chondrocytes) is suitably cultured in a medium which includes TGF-beta. The medium can also suitably include ascorbate and/or dexamethasone. The culturing is suitably carried out in a bioreactor which can also be configured for applying mechanical loading to the developing engineered tissue, as described in detail below.

The cell-seeded scaffold is suitably cultured in the bioreactor for a period of about 28 days to about 70 days, and more suitably for a period of about 28 days to about 56 days. It has been discovered that by using the methods of the present invention, engineered cartilaginous tissue having properties similar to those of native cartilage can be grown in the bioreactor in less than about 4, 5, 6, 7, or 8 weeks.

The medium in which the cell-seeded scaffold is incubated is suitably substantially serum-free. The use of tissue culture supplements such as serum is undesirable because such supplements are not chemically well-defined and can possess batch-to-batch compositional variations, raising quality control concerns for clinical applications of engineered tissue grown in the presence of serum.

In embodiments wherein the chondrocytes are chondrocytes derived from the cartilage of an adult human or animal subject, the TGF-beta is suitably present in the medium for substantially the entire period during which the cell-seeded scaffold is cultured in the bioreactor. For example, in one embodiment, the cell-seeded scaffold is cultured for 60 days with continuous growth factor (TGF-beta3) supplementation.

In embodiments wherein the chondrocytes are chondrocytes derived from the cartilage of an immature human or animal subject, it is advantageous to culture the cell-seeded scaffold in a medium in which TGF-beta is transiently present. For example, cell-seeded scaffolds containing immature chondrocytes can suitably be cultured in a medium supplemented with TGF-beta for about the first 14 days of the culture period, and subsequent culturing can be carried out in a medium which is substantially free of TGF-beta. When immature chondrocytes are used, these culture conditions lead to dramatic increases in the Young's modulus and the GAG content The TGF-beta is suitably present in the medium at a concentration of about 1 ng/ml to about 100 ng/ml. For example, the TGF-beta can be suitably present in the medium at a concentration of 10 ng/ml. The TGF-beta can suitably be TGF-beta1 or TGF-beta3. Furthermore, in addition to the TGF-beta, one or more other growth factors may also be included in the medium. In particular, it has been found that the addition of insulin-like growth factor-1 (IGF-1) to the medium results in a high compressive Young's modulus and a high GAG content in the engineered cartilage.

Dynamic Loading

The maturation process suitably includes periodic mechanical loading of the cell-seeded scaffold/developing engineered tissue to facilitate development of cartilaginous tissue having the desirable characteristics described above. The mechanical loading subjects the chondrocytes to conditions that are similar to what they would encounter in vivo in an articular joint. The chondrocytes respond to the loading by producing an ECM that is more similar in composition and arrangement to the ECM of native articular cartilage than would be produced in the same amount of time by chondrocytes that are not subjected to mechanical loading.

When mechanical loading is used, the maturation process suitably includes an exercise period in which the constructs are subjected to dynamic loading (meaning the load is repeatedly applied and removed) for a period of time followed by a rest period in which the constructs are not subjected to any significant mechanical loading. For example, the exercise period may include one or more exercise periods per day that are about 3 hours in total length and rest periods can include one or more rest periods totaling about 21 hours in length. The mechanical loading does not need to be applied every day. Good results have been obtained by exercising the constructs for about 3 hours daily for five days a week followed by two days without mechanical loading.

Various types of dynamic loading can be applied to the developing engineered tissue within the scope of the invention. One type of dynamic loading is unconstrained compression loading. Unconstrained compression loading can be applied by compressing the cell-seeded scaffold/developing engineered tissue axially (e.g., between two platens) while movement in the radial direction is unconstrained. See U.S. Pub. Pat. App. No. 20020106625, the contents of which are hereby incorporated by reference, for an example of a bioreactor operable to apply unconstrained compression loading. The axial load is suitably sufficient to produce deformation that reduces the thickness of the developing engineered tissue by up to about 50 percent, more suitably in the range of about 10 percent to about 30 percent, and still more suitably about 20 percent. The axial load is suitably applied with a frequency in the range of about 0.1 Hz to about 5 Hz.

Figure 6A:
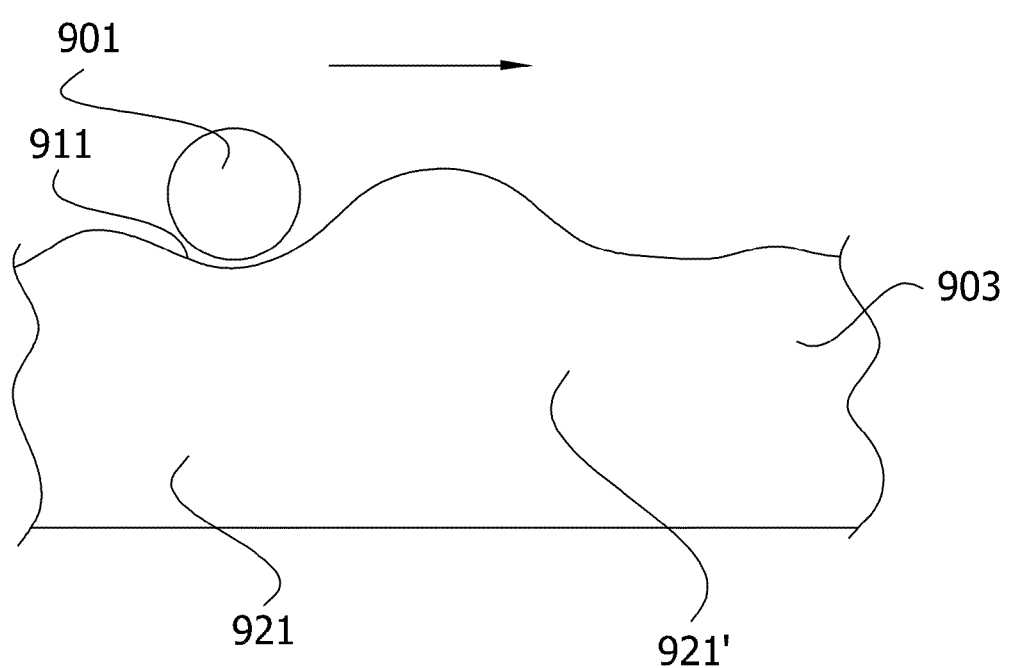
FIGS. 6A-6B are schematic diagrams illustrating a sequence in which the bioreactor illustrated in FIG. 6 is used to apply a sliding deformational load to developing engineered tissue.
Figure 6B:
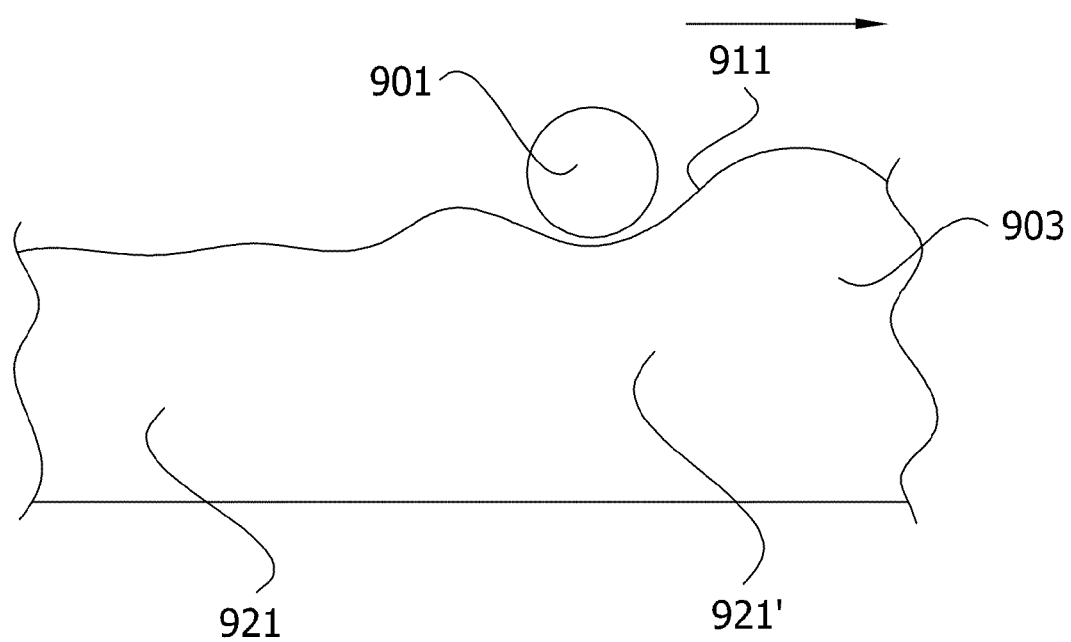

Another type of dynamic loading that can be applied is a combination of compression loading and sliding/friction loading. This type of loading can be achieved by compressing a portion or all of the cell-seeded scaffold/developing engineered tissue with a platen and sliding the platen across a surface thereof. For example, as illustrated in FIGS. 6A and 6B, a platen 901 can be pressed against only a portion of the articular bearing surface 911 of the cell-seeded scaffold/developing engineered tissue 903 and slid across the articular bearing surface (e.g., in the direction of the arrow). As illustrated in FIG. 6A, the platen compresses a portion 921 of the cell-seeded scaffold 903 while another portion 921' of the cell-seed scaffold is temporarily maintained in a substantially uncompressed state. As the platen slides across the developing articular bearing surface 911 the zone of compression in the cell-seeded scaffold 903 under the platen 901 migrates through the scaffold/developing tissue. Accordingly, after the platen has been slid across the articular bearing surface to a new position, as illustrated in FIG. 6B, the portion 921' of the scaffold 903 that was not compressed in FIG. 6A is compressed by the platen 901 and the portion 921 of the scaffold that was compressed in FIG. 6A is temporarily maintained in a substantially uncompressed state.

While not being bound by any particular theory, it is believed the sliding regime can provide improved results in some cases because the smaller contact area between the platen 901 and the scaffold 903 provides the scaffold with improved access to culture media during the exercise period, particularly when compared to a compression loading regime in which the upper and lower surfaces of the scaffold 903 are completely covered by the platens and the most significant pathway available for diffusion of nutrients into the scaffold radially inward from unconstrained edge margins of the scaffold.

In contrast, in the sliding/friction loading regime illustrated in FIGS. 6A and 6B, no more than about 5 to about 50 percent of the surface of the developing articular bearing surface is contacted by the platen 901 at any time. In other words, the dynamic loading is conducted so at least about 50 percent to about 95 percent of the developing articular bearing surface 911 of the engineered tissue 903 is in contact with the culture media while the platen 901 is sliding across the articular bearing surface.

The axial deformation load applied by the sliding platen 901 to the scaffold 903 can vary within the scope of the invention. The axial load is suitably sufficient to compress the tissue thickness in the range of about 0.1 mm to about 5 mm. The amount of compression can vary according to the thickness of the cell seeded scaffold. In general, it is best to avoid compressing the tissue more than about 20 percent because this can lead to chondrocyte deactivation and other undesirable outcomes.

For example, the axial load applied by the sliding platen 901 to the scaffold is suitably sufficient to reduce the thickness of the compressed tissue in the range of about 10 percent to about 20 percent.

Dynamic mechanical loading as described above, can be applied to the cell-seeded scaffold/developing engineered tissue 903 using the bioreactor described below and illustrated in FIGS. 7-12B.

Figure 7:
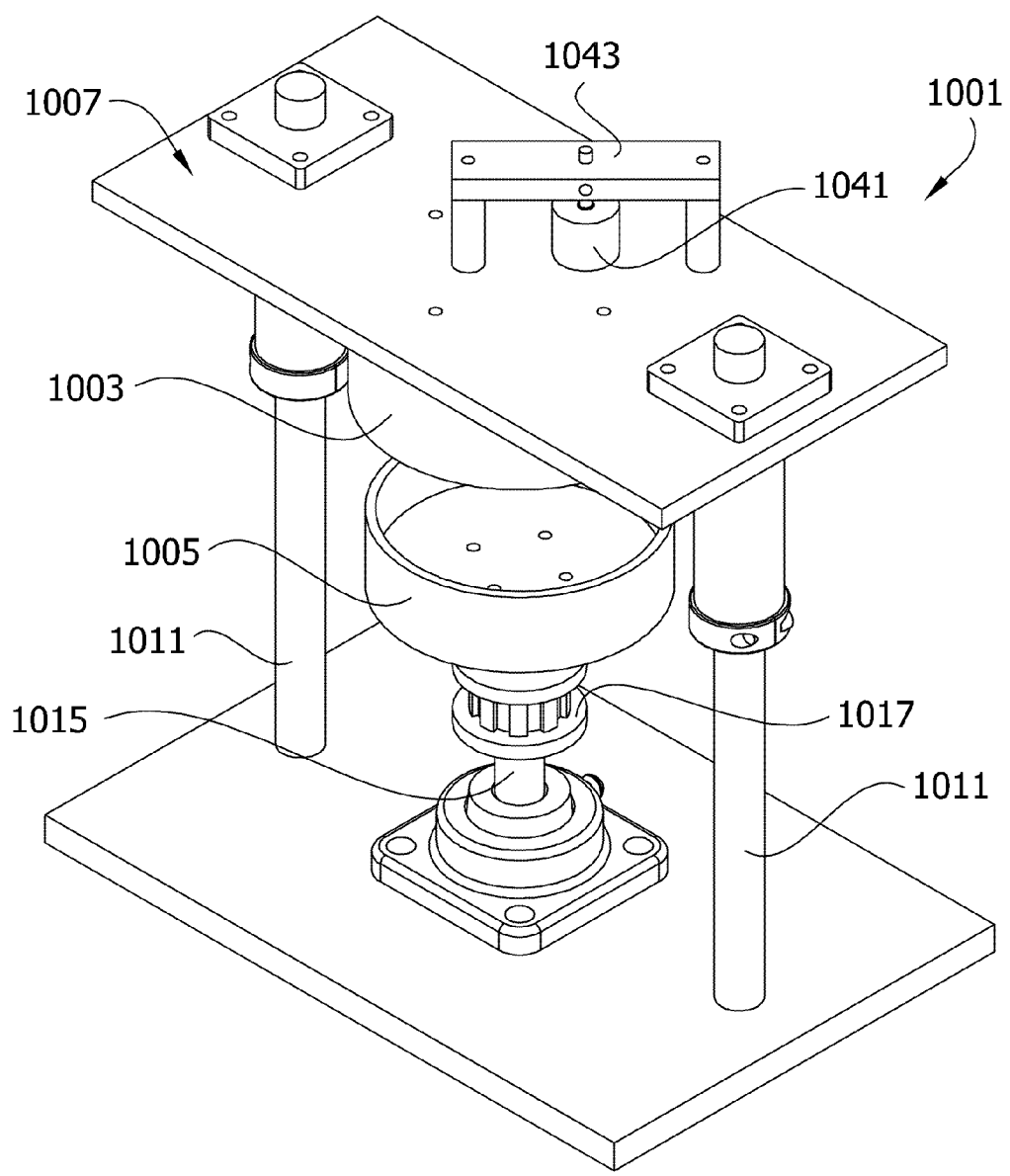
FIG. 7 is a perspective of one embodiment of a bioreactor operable to apply sliding mechanical loading of developing engineered tissue.
Figure 10:
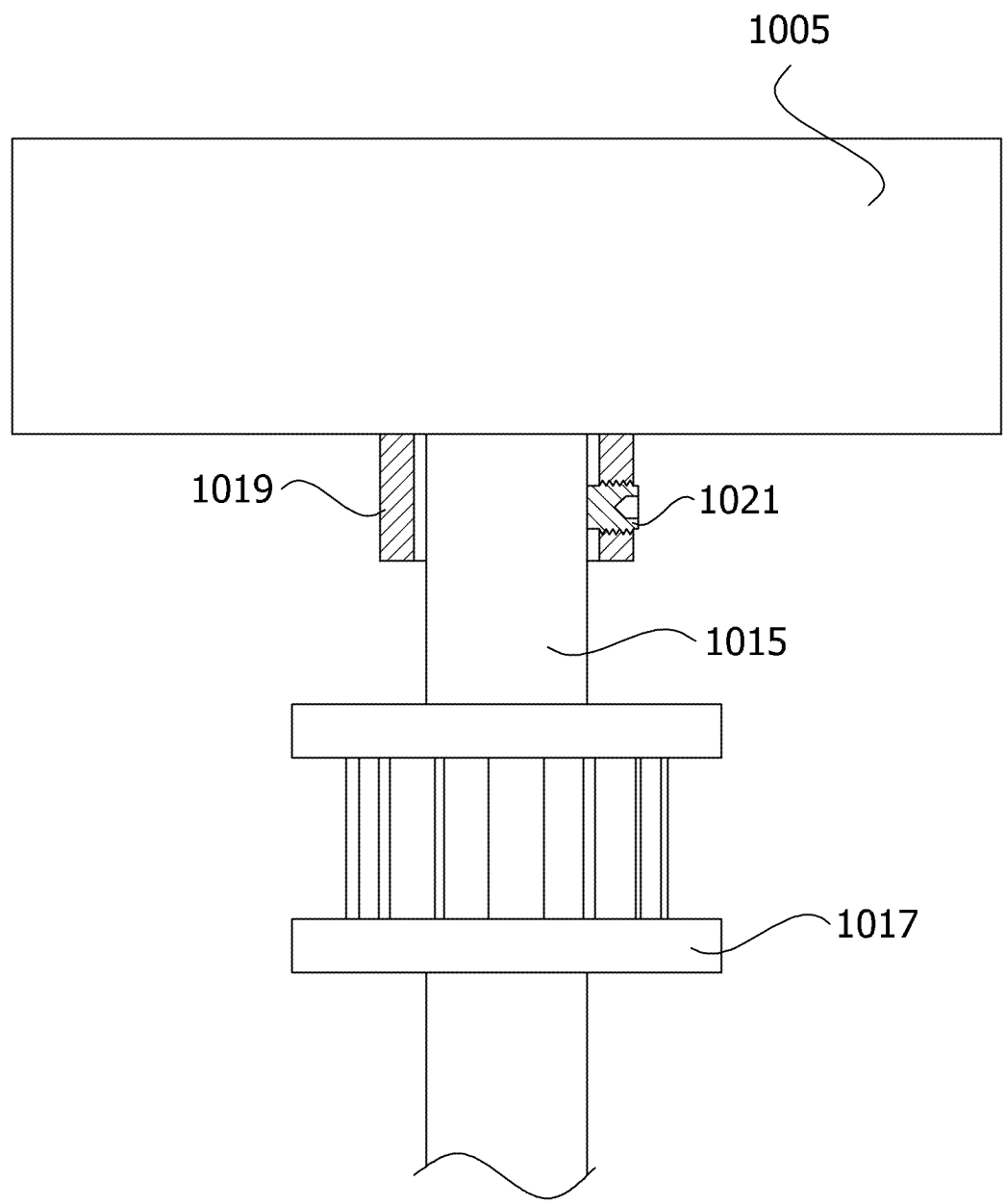
FIG. 10 is a front elevation of various components of the bioreactor illustrated in FIG. 7 showing connection of a bottom dish to a drive system for rotation of the bottom dish.

Referring to FIG. 7, one embodiment of a bioreactor, generally designated 1001, suitable for applying dynamic mechanical loads to cell-seeded scaffolds/developing engineered tissue has a chamber defined by a cover 1003 and a container 1005 (broadly a "support"). The cover 1003 is suitably fixed to a top plate assembly 1007 slideably mounted on a pair of substantially vertical rods 1011 allowing the top plate assembly and cover to be lifted to access the chamber and lowered to replace the cover on the container 1005. As best illustrated in FIG. 10, the container 1005 is supported by the upper end of a lead screw 1015 to which the container is connected for conjoint rotation with the lead screw. For example, a plurality of set screws 1021 (only one of which is visible in FIG. 10) can be used to center the lead screw 1015 within an oversized retainer 1019 so the threads of the lead screw do not engage the container 1003 in a manner that drives up or downward movement of the container. The lead screw 1015 suitably includes flats (not shown) positioned so the set screws 1021 can engage the flats to make a stronger connection between the lead screw and the container 1005.

Figure 9:
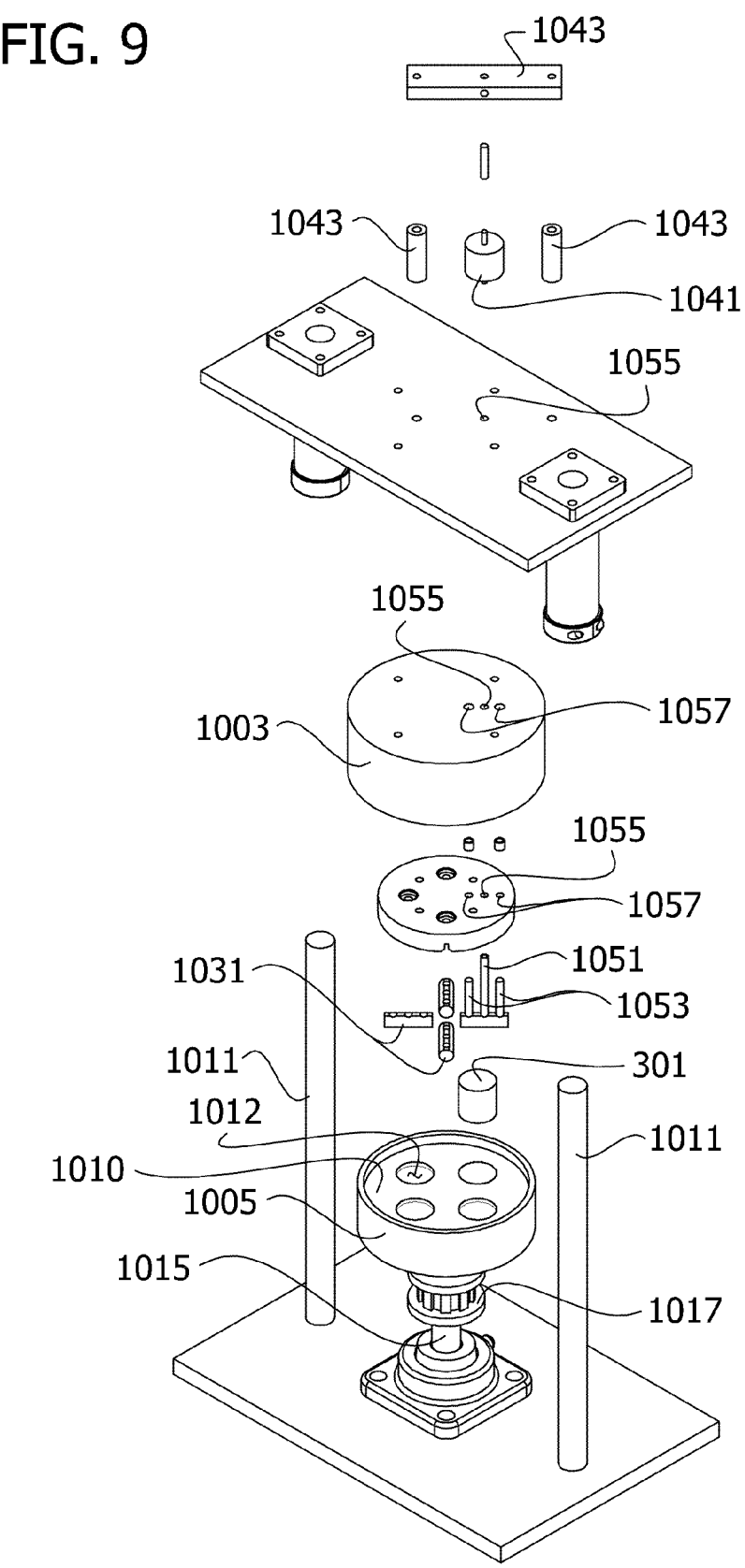
FIG. 9 is an exploded perspective of the bioreactor illustrated in FIG. 7.

The bottom of the container 1005 is suitably filled with a layer of gel 1010 (e.g., agarose). A plurality of wells 1012 are cut or otherwise formed in the gel for holding a developing engineered tissue construct, which in FIG. 9 is illustrated as the tantalum based osteochondral plug type implant 301 described above. The sides of the well 1012 hold the construct so it does not move when frictional loading is applied to it, as described below.

A pulley 1017 mounted on the lead screw can is suitably connected to a motor by a belt (motor and belt not shown) to drive rotation of the lead screw. The motor is suitably operable to drive cyclical rotation of the lead screw 1015 back and forth in opposite directions (e.g., at a frequency of about 1 Hz). As the lead screw 1015 rotates back and forth, e.g., over a range of about 360 degrees, the container 1005, which is rotatably fixed to the lead screw by the set screws 1021, rotates along with the lead screw relative to the cover 1003 and top assembly 1007.

Figure 8:
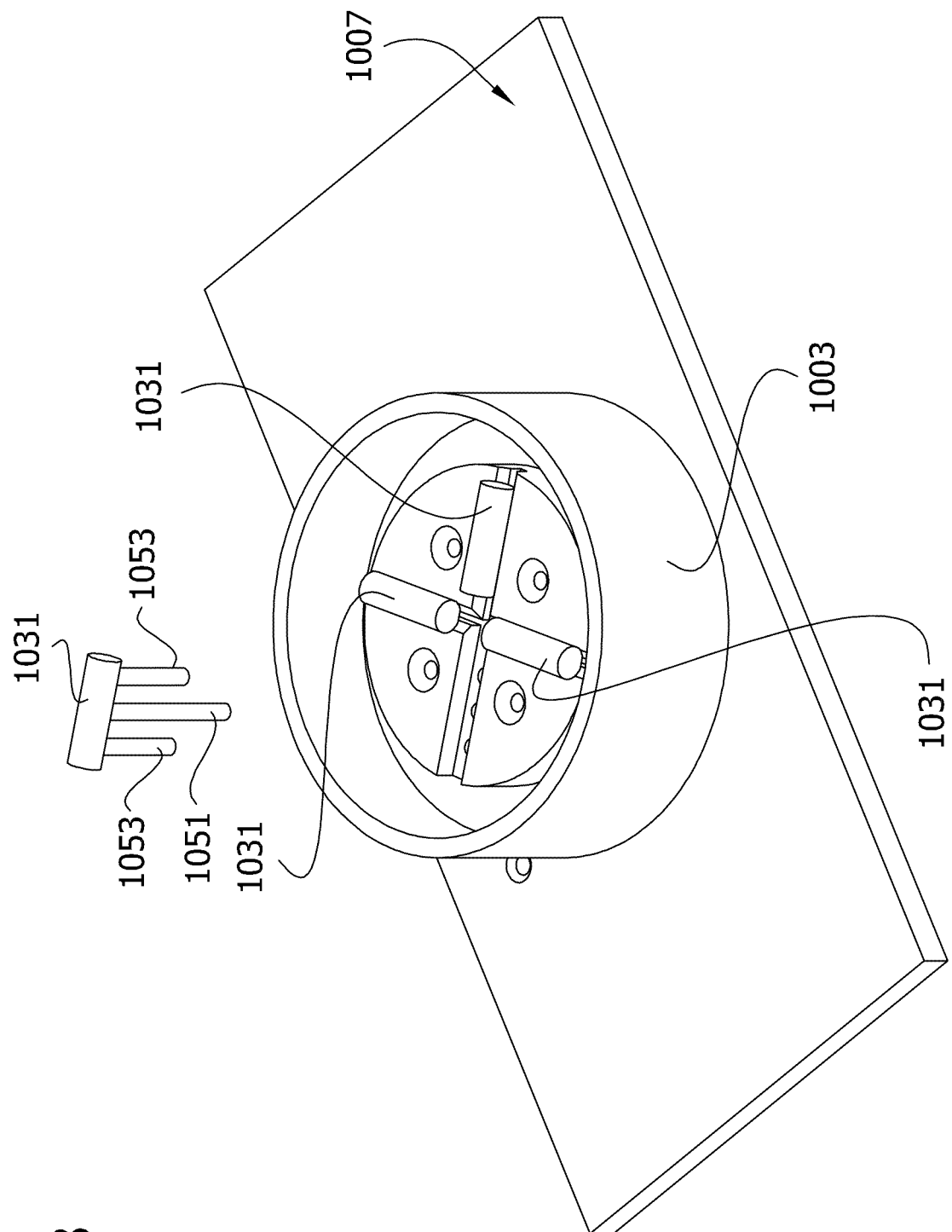
FIG. 8 is a perspective of components of the bioreactor illustrated in FIG. 7.

As illustrated in FIG. 8, the cover includes one or more platens 1031 (e.g., four platens) positioned to contact the upper surface (e.g., the developing articular bearing surface) of the engineered tissue constructs in the chamber supported by the container 1005. As the container 1005 is rotated by the motor, the platens 1031 slide across the upper surface of the developing engineered tissue constructs in the manner illustrated in FIGS. 6A-6B and described above.

A load cell 1041 is supported on the top plate assembly 1007 by a bracket 1043 (FIGS. 7 and 9). The load cell 1041 is operable to measure the axial compressive load applied by one of the platens 1031 to the scaffold/engineered tissue. The load cell 1041 is suitably connected to one of the platens 1031 by a connecting rod 1051 that extends through an opening 1055 in the top plate assembly 1007 from the load cell to the platen. Guide rods 1053, which are vertically slideable within generally cylindrical openings 1057 in the top plate assembly, 1007 are connected to the platen 1031 on either side of the connecting rod 1051. When the platen 1031 contacts a cell-seeded scaffold/engineered tissue, the force exerted on the platen is transmitted to the load cell 1041 through the connecting rod 1051. Although it is desirable for each of the engineered tissue constructs in the bioreactor to have the same size and shape, there will be some variation in the size and shape of the tissue constructs. There can also be alignment problems that could impact loading of the developing engineered tissue constructs by the platen. The load cell 1041 monitors the force applied to each of the developing tissue constructs as it slides under the platen connected to the load cell. If one or more of the tissue constructs is receiving too much loading, this will be indicated by a spike in the output of the load cell 1041. Load measurements may be made in any suitable manner within the scope of the invention.

Figure 11:
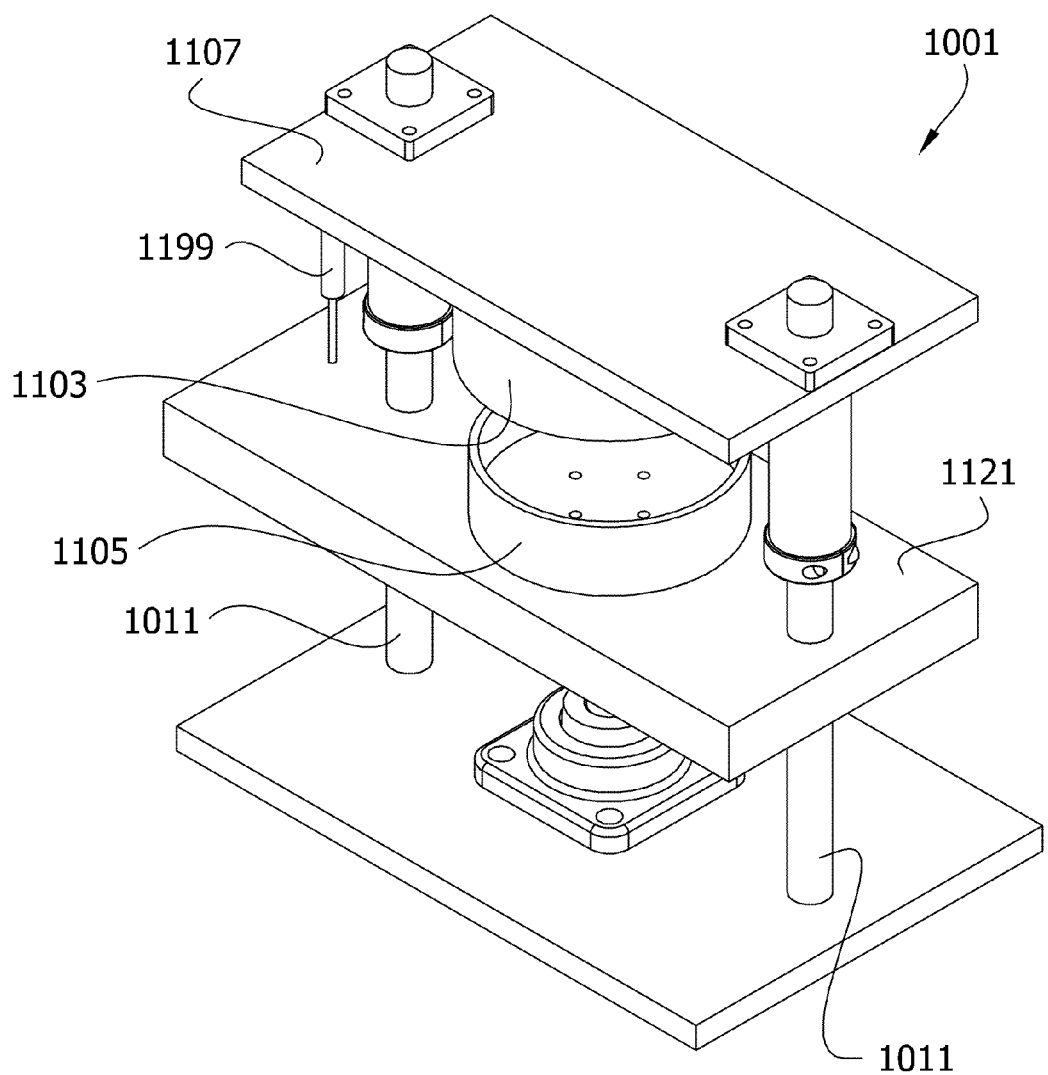
FIG. 11 is a perspective of the bioreactor illustrated in FIG. 6 in which various modular components have been replaced to convert the bioreactor from a mode in which it applies axial compression loading to developing engineered tissue instead of the sliding deformation load.
Figure 12A:
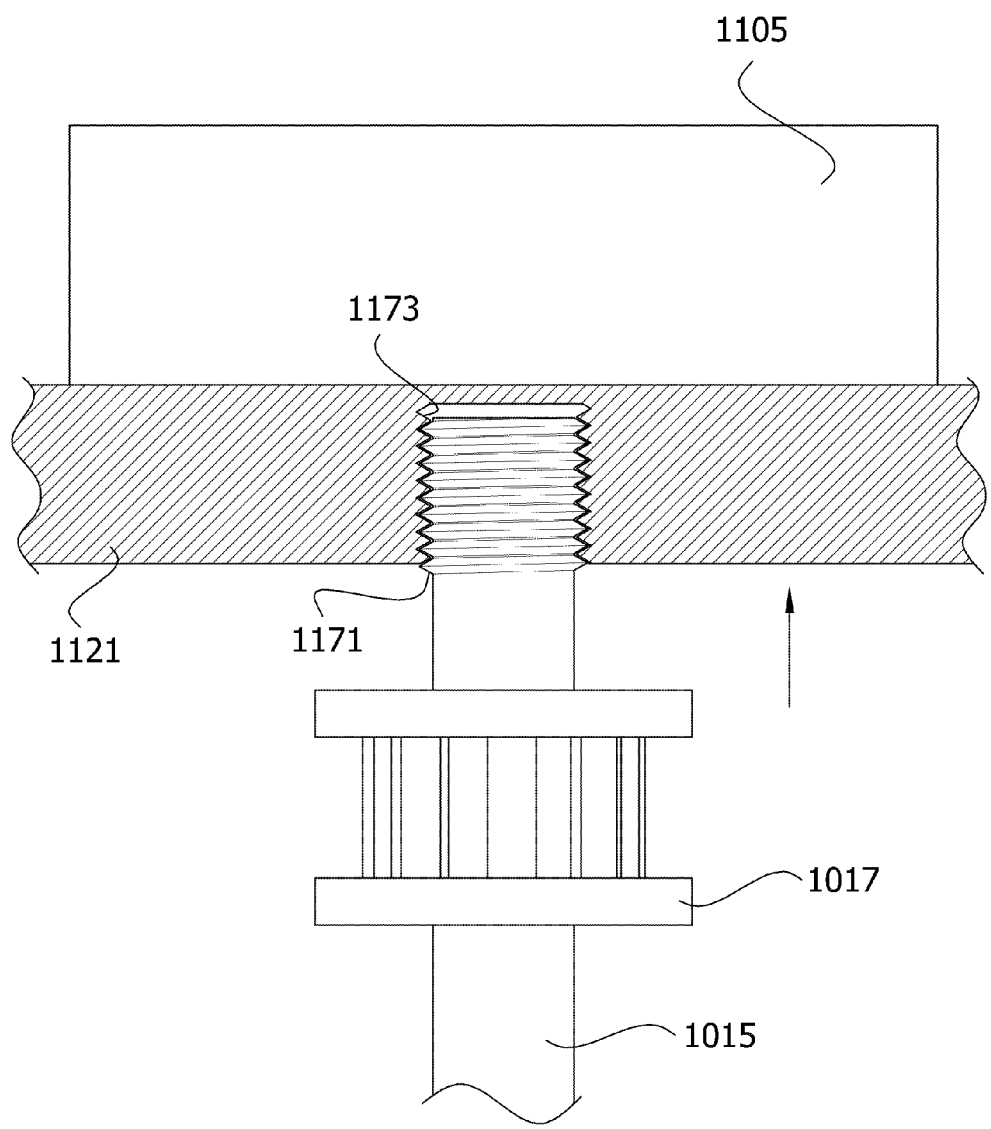
FIGS. 12A and 12B illustrate a connection of the bottom dish to the drive system for cyclical raising and lowering of the bottom dish by the drive system.
Figure 12B:
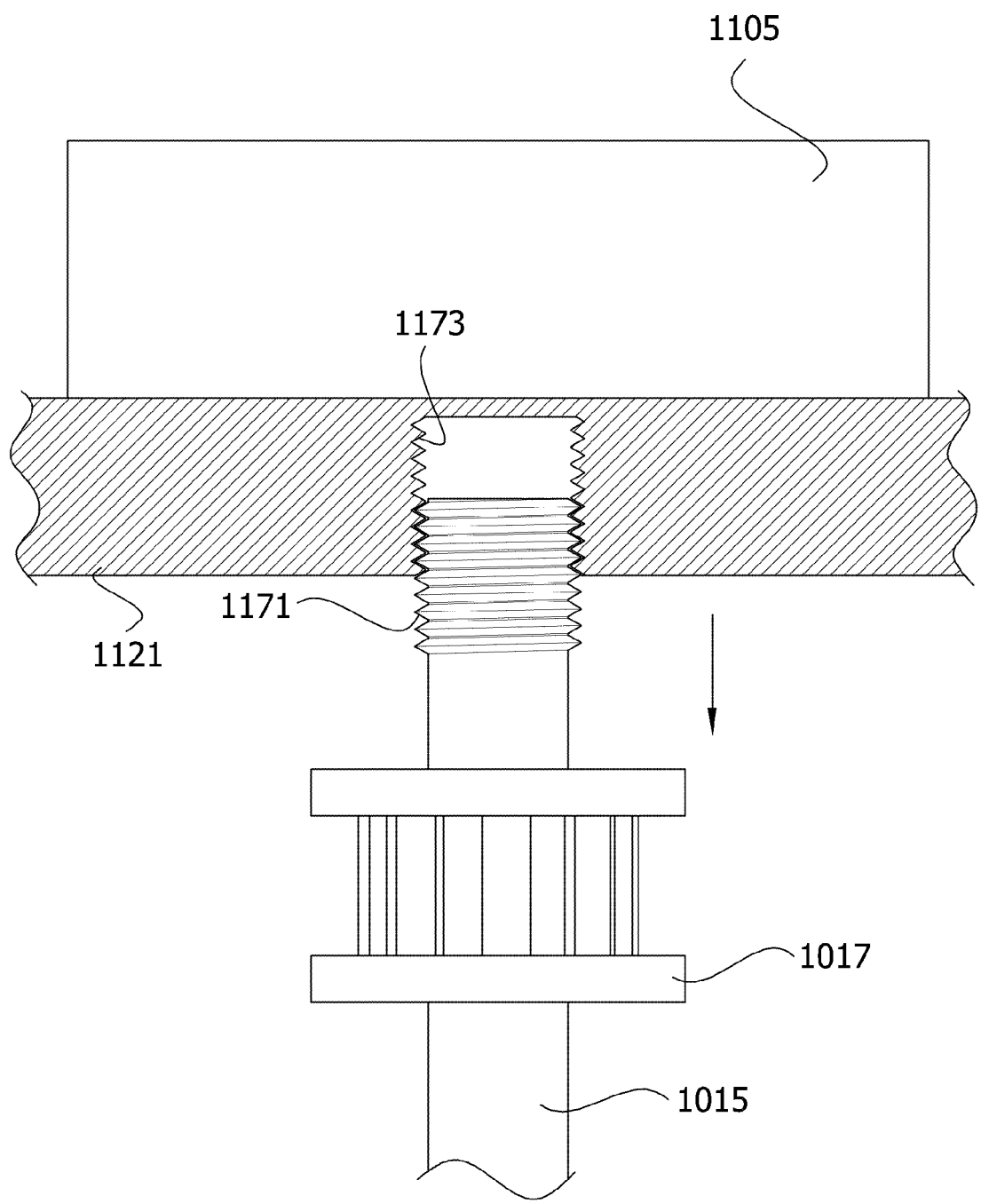

The bioreactor 1001 can readily be converted for application of unconstrained dynamic compression loads by replacing the top plate assembly 1007 with the top assembly 1107 illustrated in FIG. 11 and by replacing the container 1005 with the container 1105 illustrated in FIGS. 11, 12A, and 12B. The container 1105 is supported by a plate 1121 slidably mounted on the rods 1011. The plate 1121 has a threaded opening 1173 than engages the threads 1171 of the lead screw 1015. The plate 1121 is held against rotation so rotation of the lead screw 1015 by the motor in the same back and forth cyclical manner described above drives the plate (and therefore the container 1105) to move up and down in a cyclical manner (e.g., at a frequency of about 1 Hz). As the container 1105 is raised by the motor, the cell-seeded scaffolds/engineered tissues are pressed against the ceiling (not shown) provided by the cover 1103. Thus, the developing engineered tissues are subjected to cyclical deformational loading. A sensor 1199 (e.g., a linear variable displacement transducer) is suitably positioned between the top plate assembly 1107 and the plate 1121 to monitor the position of the plate 1121 and send a output a signal that causes the motor to reverse directions at appropriate times.

EXAMPLE 1

Example 1 illustrates the effects two different materials (devitalized trabecular bone and tantalum) have on chondral development when used as the material for the porous substrate for an osteochondral implant.

Experimental Design of Example 1

Figure 13:
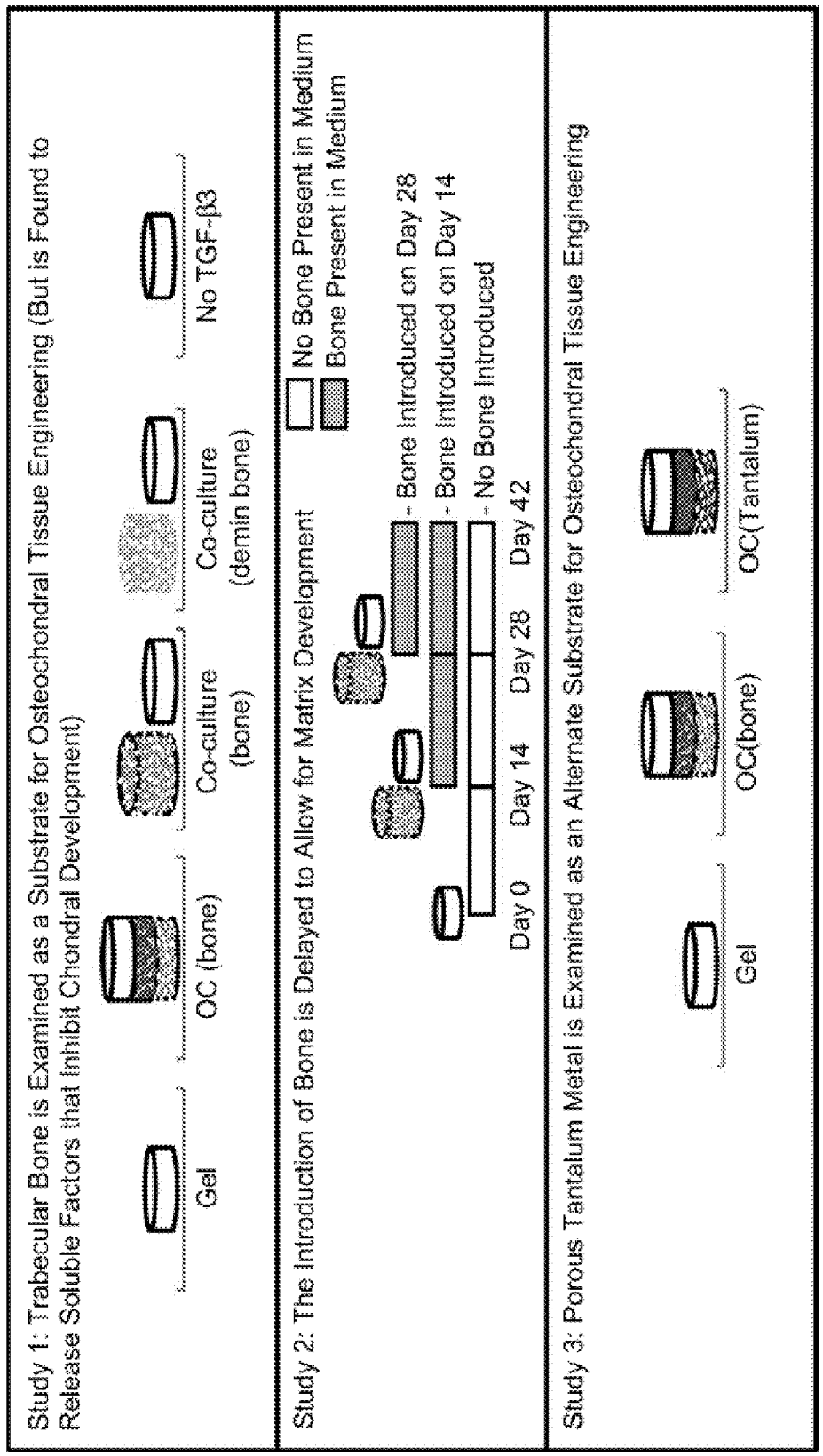
FIG. 13 is a schematic diagram representing the experimental design for Example 1, which explores the impact the material selected for osteo portion of osteochondral implant has on chondral development.

Referring to FIG. 13, three related studies were conducted in Example 1.

In Study 1 of Example 1, the development of chondrocyte-seeded agarose hydrogel constructs and osteochondral constructs were directly compared using the same tissue-engineering protocol. To assess the effects of soluble factors released by bone, chondral only constructs were also co-cultured adjacent (but unattached) to devitalized bone. To exclude the effect of soluble minerals, chondral only constructs were also cultured adjacent to demineralized bone. Finally, to test for the possibility that the inhibitory effect of bone is not related to soluble factors, but rather due to a decrease in the availability of growth factors through the absorption into bone, chondral only constructs were cultured in medium without TGF-β3.

In Study 2 of Example 1, the formation of functional osteochondral implants after separate cultivation of the chondral region was examined by delaying the introduction of bone to day 14 of culture or on day 28. Chondral only constructs were also cultured without any bone to serve as controls.

In Study 3 of Example 1, osteochondral constructs were formed with a porous tantalum metal substrate and compared to osteochondral constructs that included trabecular bone and chondral only constructs that did not include any bone.

Each study was carried out separately and all groups were cultured for 42 days.

Materials and Methods for Example 1

Cell Isolation. Articular cartilage was harvested from bovine carpo-metacarpal (CMC) joints of freshly slaughtered 1-3 weeks old calves. Three to five joints were used for each study and cells were pooled from all joints. Cartilage chunks were digested in DMEM with 390 U/ml collagenase type VI (Sigma Chemicals, St. Louis, Mo.) for 11 hours at 37 C with stirring. The resulting cell suspension was then filtered through a 70 μm pore-size mesh and sedimented in a bench top centrifuge for 10 minutes at 1000 g. Viable cells were counted using a hemocytometer and trypan blue.

Osteochondral Substrate preparation. To prepare devitalized bone, cylindrical cores (about 15 mm long) of trabecular bone were isolated from the subchondral region of bovine tibia using a diamond-tipped, hollow drill (Starlite, Rosemont, Pa.). Cores were rough cut to about 6 mm in length and centered in a custom 4 mm thick stainless steel mold such that there were overhanging surfaces on both sides of the mold. These surfaces were then sanded flat with a hand-held device to ensure that the final bone cores had uniform dimensions (4 mm diameter×4 mm±50 μm length) with parallel faces cut normal to the axis of symmetry. The bone cores were then cleaned of marrow in one of three ways: 1) with a water pick and subsequently sterilized in 70% ethanol for four hours, 2) by washing in hypotonic buffer with detergent and DNAse and RNAse solutions, or 3) as provided by a commercial vendor through their FDA approved BioCleanse processes (RTI Biologics). To keep the quantity of bone consistent between experiments, cleansed bone was sorted to within a 10% deviation in mass and volume. The experiments presented in Study 1 of Example 1 and Study 2 of Example 1 were repeated with each of these cleaning methods with no significant differences in results. The data presented here are averaged across all experiments.

Demineralized bone. For the co-culture (Demin) group in Study 1 bone was demineralized in 6 N HCl for 12 hours.

Tantalum metal. Porous tantalum metal substrates (Zimmer) were prepared using wire cut electron discharge machining (to maintain the scaffold porosity) to final construct dimensions of 4 mm diameter×4 mm length.

Growth medium. The growth medium was changed every other day and consisted of high glucose Dulbecco's Modified Eagle's Medium supplemented with 1×PSF (100 units/ml Penicillin, 100 μg/ml Streptomycin, 0.25 μg/ml Fungizone), 0.1 μM dexamethasone, 50 μg/mL ascorbate 2-phosphate, 40 μg/mL L-proline, 100 μg/mL sodium pyruvate, and 1×ITS+premix (insulin, human transferrin, and selenous acid, Becton Dickinson, Franklin Lakes, N.J.). The ITS+premix is a 100× aqueous solution containing 12.5 mg human recombinant insulin, 12.5 mg human transferring, 12.5 μg selenous acid, 2.5 g BSA, and 10.7 mg linoleic acid. Chemically defined medium was further supplemented with 10 ng/mL of TGF-β3 (R&D Systems, Minneapolis, Minn.) for the first 14 days of culture.

Material Testing. The equilibrium Young's modulus (EY) is commonly used as a measure of the behavior of cartilage that has been allowed to reach equilibrium after a known load or displacement has been applied. Constructs were tested for Young's modulus in unconfined compression using a custom computer-controlled testing system. An initial 0.02 N tare load was applied, followed by a compression to 10% strain (of the chondral region), at a strain rate of O.O5%/sec. Young's modulus was calculated from the equilibrium stress at 10% strain. Previous studies have shown Young's modulus to remain invariant across strain magnitudes ranging from 0% to 20%.

Figure 18:
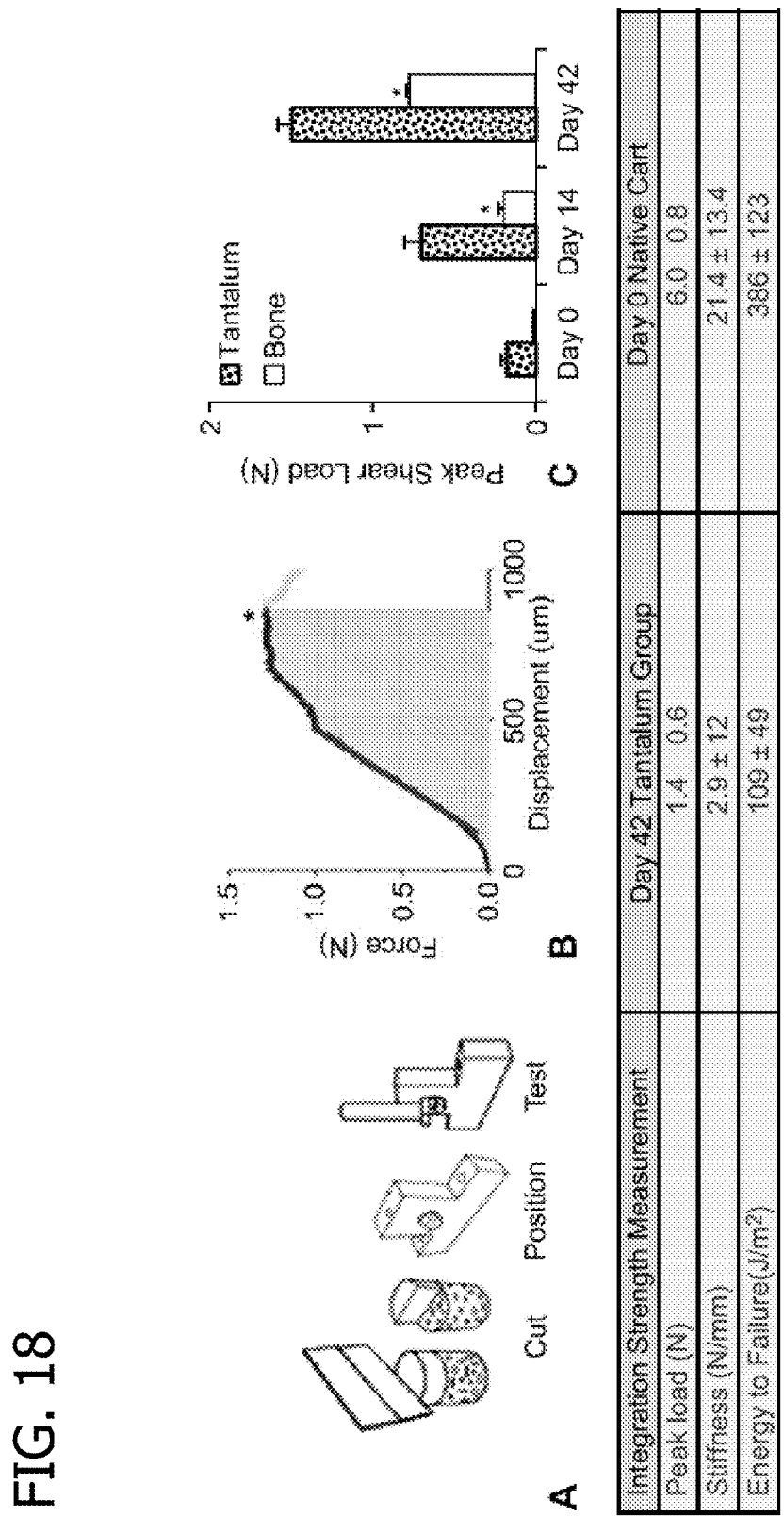
FIG. 18 includes schematic diagram illustrating shear testing of osteochondral implants and graphical results of experiments.

To determine the shear strength at the interface, the chondral region of osteochondral constructs were cut in half (FIG. 18A), and mounted in a custom mold as to allow a platen to come into contact with the newly created flat surface (FIG. 18A). A linear displacement velocity (10 μm/s) was then applied to the platen and the load measured. The shear strength at the interface was calculated in three ways, as is commonly expressed in the literature. Peak load was determined as the highest force before failure (FIG. 18B, indicated by the asterisk). Shear stiffness was determined by curve fitting the linear region on the force/displacement curve (FIG. 18B), Energy to Failure was determined by integrating the area under the force/displacement curve to the peak load and normalizing by interface area (FIG. 18B).

Biochemical Content. The biochemical content of each sample was assessed by first measuring sample wet weight, lyophilizing for 24 hours, and then measuring the sample dry weight. Once dry, the samples were digested in proteinase-K overnight at 56 C. Aliquots of digest were analyzed for glycosaminoglycan (GAG) content using the 1,9-dimethylmethylene blue dye-binding assay. A further aliquot was acid hydrolyzed in 12 N HCl at 110° C. for 16 hours, dried over NaOH, and resuspended in assay buffer. Orthohydroxyproline (OHP) content was then determined via a calorimetric assay by reaction with chloramine T and dimethylaminobenzaldehyde. OHP content was converted to total collagen content using the conversion of 1:10 ratio of OHP:collagen. Each biochemical constituent (GAG and collagen) was normalized to tissue wet weight.

Histological Analysis. Chondral samples were fixed in acid formalin ethanol, paraffin embedded, sectioned (8 μm thick), and stained to view proteoglycan or total collagen or type II collagen distribution. For osteochondral constructs histological specimens were prepared and stained at the Department of Surgical Sciences, University of Wisconsin. Live/dead assays were carried out using manufacture's protocol (Molecular Probes).

Statistics. Statistics were performed with the Statistica (Statsoft, Tulsa, Okla.) software package. Each data point represents the mean and standard deviation. Groups were examined for significant differences by analysis of variance (a=0.05), with EY, GAG, or OHP as the dependent variable using the Tukey's Honest Significant Difference Test (HSD).

Results of Study 1 of Example 1. Study 1 showed both osteochondral (OC(bone)) and chondral (Gel) constructs developed significantly better mechanical and biochemical properties over time, as illustrated in FIG. 14.

However the chondral constructs consistently performed better than the osteochondral constructs and the chondral constructs that were co-cultured with bone or demineralized bone. For example, the day 42 values for the osteochondral group were EY=87±12 kPa and GAG=1.9±0.8% w/w. In comparison, the values for the chondral only group were EY=642±97 and GAG=4.6±1.4% w/w.

Figure 15:
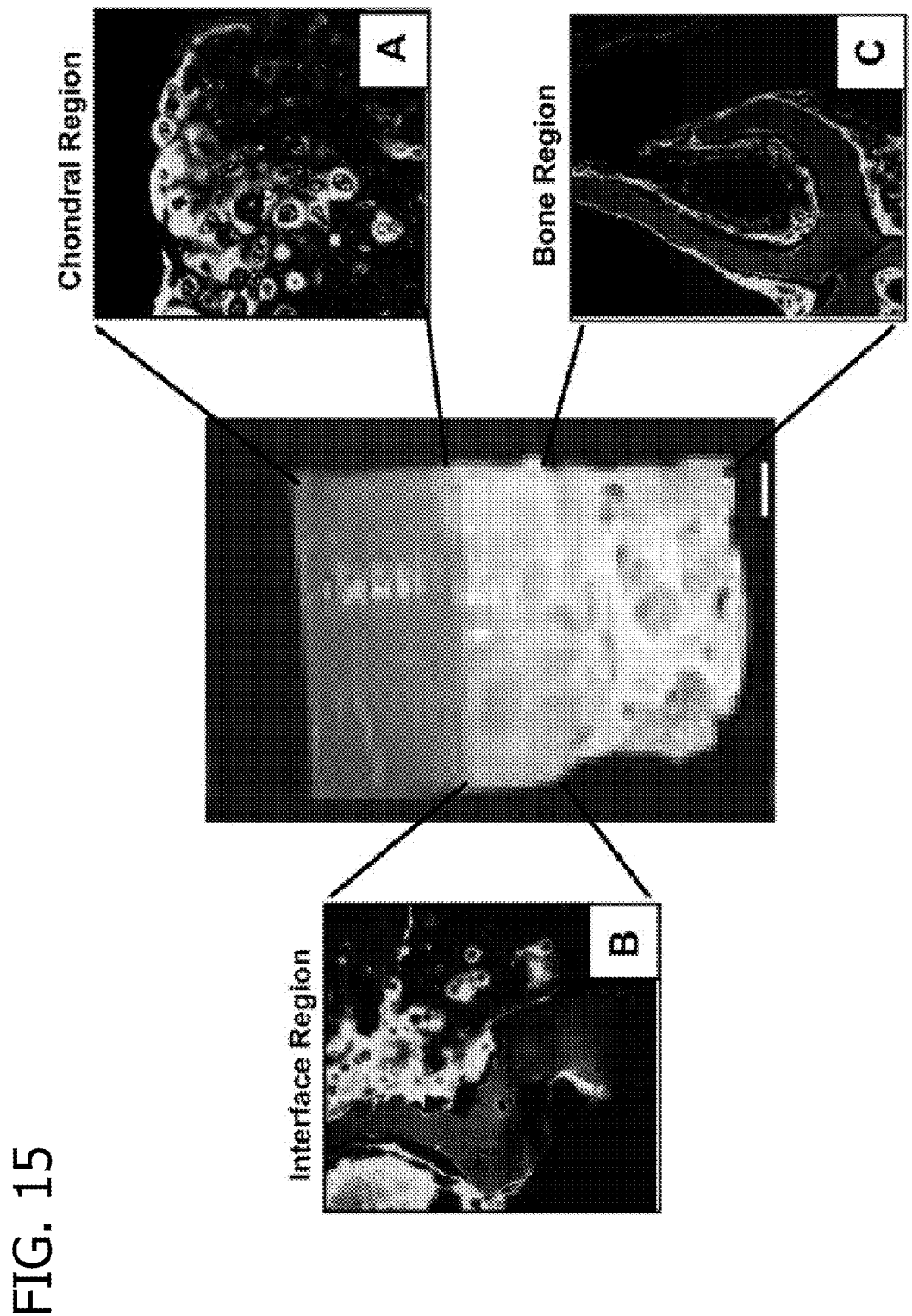
FIG. 15 contains photographs (Magnification 40×) illustrating Type II collagen deposition in the chondral region of an osteochondral implant, in the interface region between the chondral and osteo portions of the implant, and in the osteo portion of the implant.

Collagen values were not significantly different between the two groups. DNA quantification indicated a 30% increase in cell number over the culture period with no significant differences between the two groups. Live/dead staining revealed the presence of vital cells in all three regions of the osteochondral constructs, including the bone-only region where no cells were initially seeded. These cells appeared elongated and seemed to have attached to the underlying bony substrate. Immunohistological staining indicated the continued deposition of type I1 collagen in all three regions (FIG. 15), suggesting that the chondrocyte phenotype was maintained, even with the change in morphology.

Figure 14:
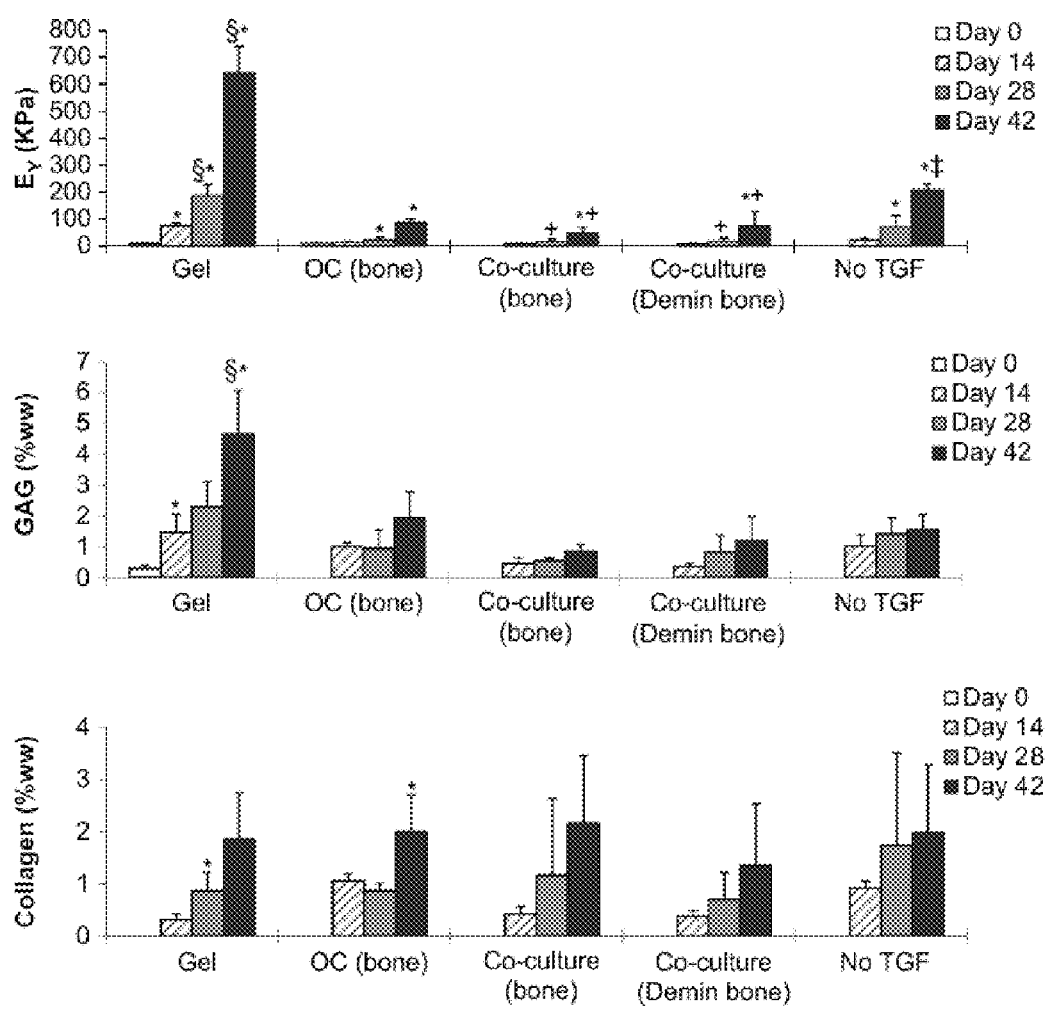
FIG. 14 includes graphical results of experiments.

The presence of separate bone plugs in the co-culture experiments (co-culture (bone)) resulted in significantly lower EY and GAG by day 42 than the chondral only groups and no statistical differences from the osteochondral group (FIG. 14). The demineralization of the bone (co-culture (demin) did not ameliorate these effects, yielding no statistical differences in EY, GAG, or collagen from the osteochondral groups and yielding statistically lower EY and GAG than the Gel group (FIG. 14).

Constructs cultured without TGF-3 (noTGF) resulted in significantly lower EY and GAG when compared to the chondral only groups, but higher EY than the osteochondral group (FIG. 14). Histological staining indicated a well-distributed extracellular network in all groups. Von Kossa staining did not indicate an osteogenic phenotype.

Figure 16:
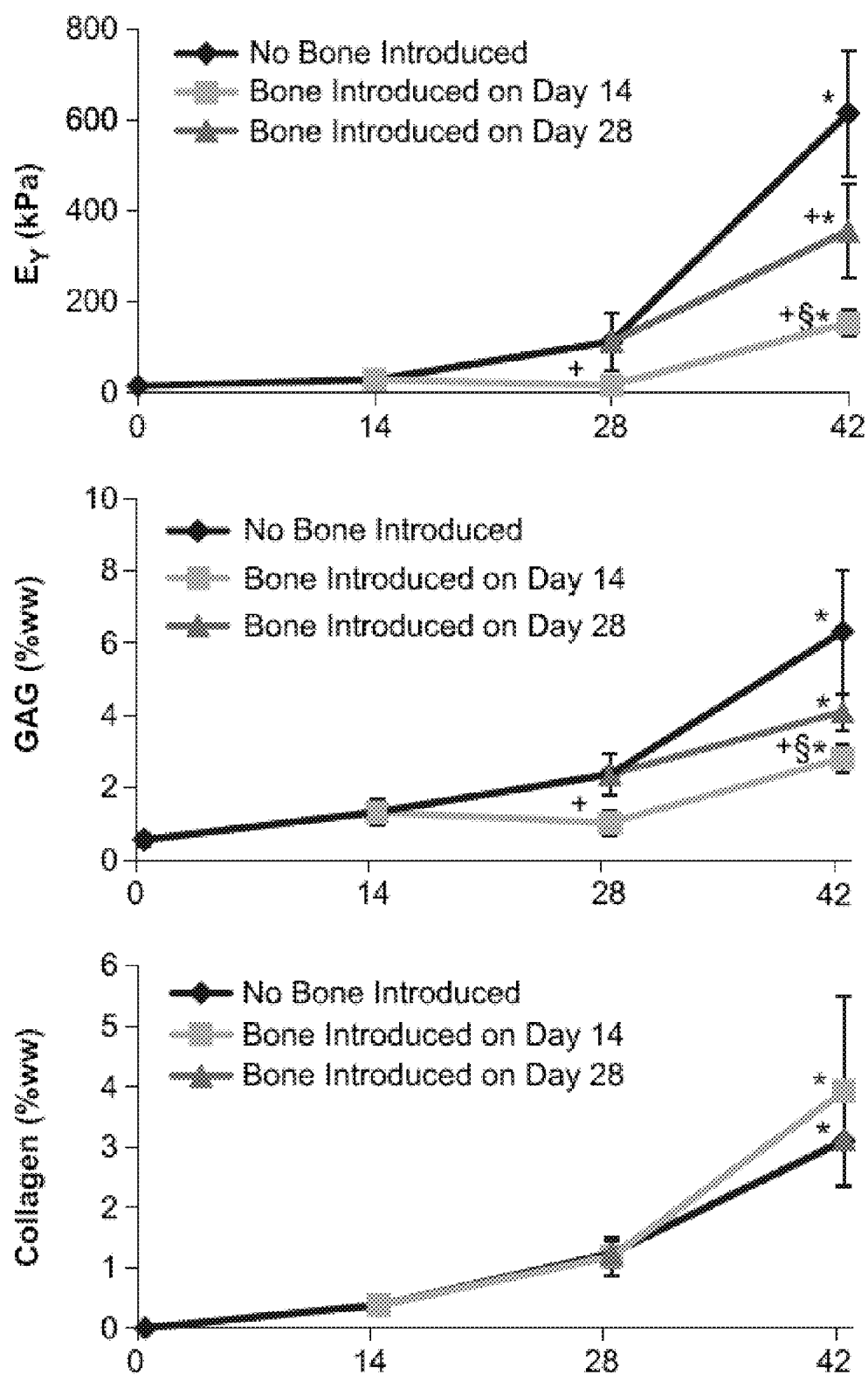
FIG. 16 includes graphical results of experiments.

Results of Study 2 of Example 1. Study 2 showed the addition of bone to the culture medium resulted in lower EY values regardless of whether the bone was added later in culture (FIG. 16). The introduction of bone on day 14 resulted in an EY that was 15% of the chondral only (Gel) group by day 28 and 25% of the Gel group by day 42. Likewise introduction of bone on day 28 resulted in 58% of the EY of Gel group by day 42. GAG values were similarly lower between the two bone groups and the gel group, with the exception of the day 42 bone introduced on d28 group versus Gel. There were no significant differences in collagen values between any of the groups.

Figure 17:
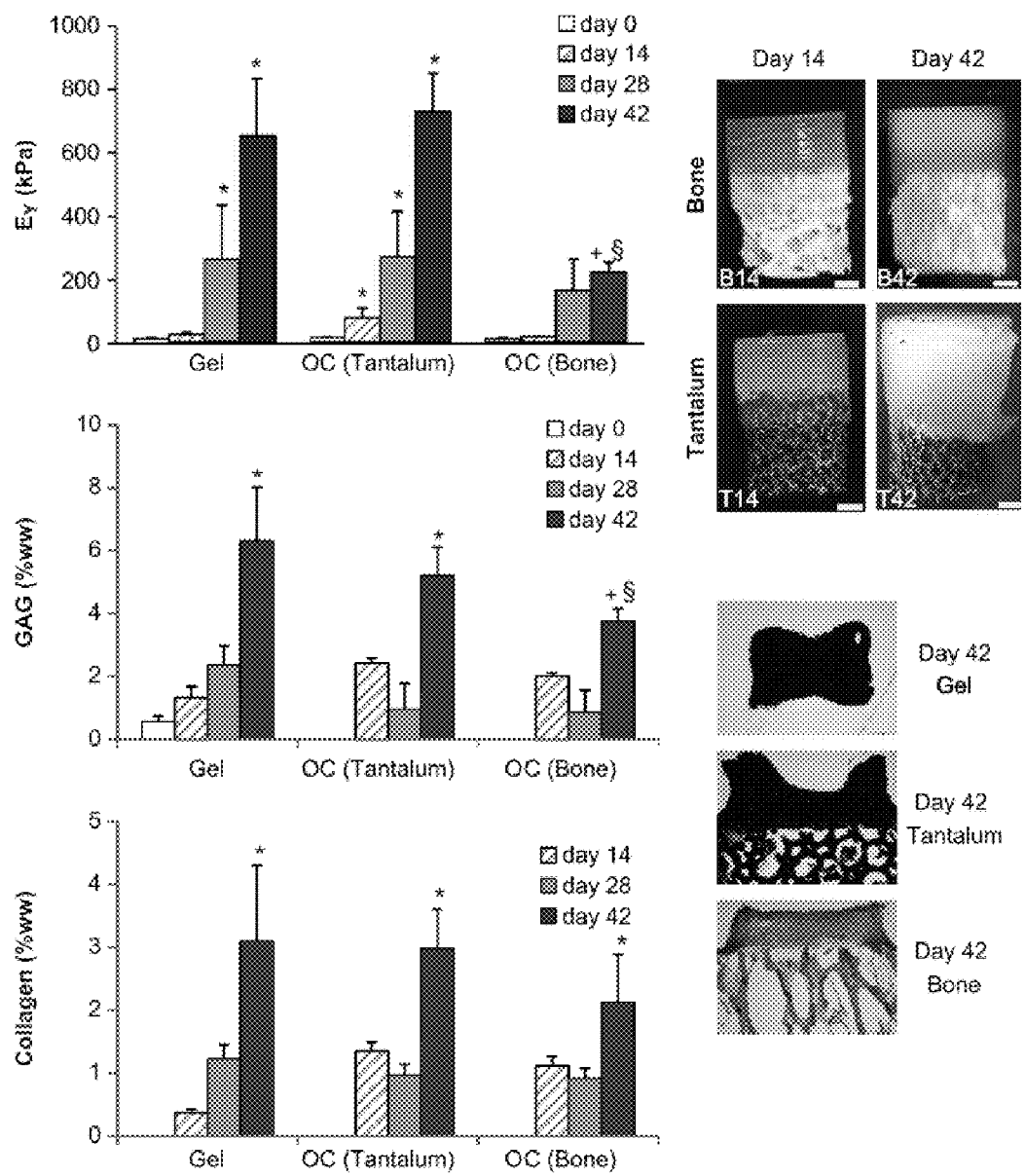
FIG. 17 includes graphical results of experiments and photographs illustrating the results of the experiments.

Results of Study 3 of Example 1. Study 3 showed that by day 42, osteochondral groups formed with bone substrate (OC (Bone)) developed significantly lower EY and GAG than chondral only (Gel) groups (FIG. 17), consistent with what was observed in Studies 1 and 2 of this example. Osteochondral constructs formed using a porous tantalum base, on the other hand, were not adversely affected by the porous substrate and developed an EY of 730±65 kPa; a value within the range of native cartilage (500–1500 kPa). Gross morphology indicated a robust, cartilage-like chondral layer by day 42 in OC (tantalum) specimens. The chondral region in OC (Bone) specimens appeared in some cases to have developed a gradient of extracellular deposition, becoming whiter and denser farther from the bony substrate (see photos in FIG. 17). Unfortunately, there was some shrinkage in the histological preparation of the specimens of Study 3. Nevertheless staining clearly indicated rich accumulation of proteoglycans in both the Gel and the OC (tantalum) groups, with less intense staining in OC (bone) groups. Shear testing (FIG. 18C) showed that the integration strength of the chondral region to the tantalum base was more than 200% that of the OC (bone) groups expressed as peak load. Similar results (not shown) were obtained when the integration strength was expressed as stiffness and energy to failure. By comparison OC (tantalum) groups developed 28% of the energy to failure observed in native osteochondral specimens.

Discussion of Example 1 Results. Taken together the Studies in Example 1 demonstrate that devitalized trabecular bone has in at least some cases an inhibitory effect on in vitro chondral tissue development when used as a base material for the tissue-engineering of osteochondral constructs for cartilage repair. Although not bound by any particular theory, it appears likely the bone was adversely affecting tissue development because soluble chemical mediators were inhibiting the observed chondral tissue development. It may be that osteoinductive factors released by bone may contribute to suppression of the chondrogenic phenotype. Bone matrix is known to contain intrinsic cytokines and growth factors that have a wide and largely unknown range of effects on cell development. The type and concentration of these factors vary even between the bones of the same animal.

The generation of osteochondral constructs was most successful when bone was substituted with a non-biological alternative. Using porous tantalum metal, native Young's modulus values and GAG and collagen content similar to chondral-only constructs were achieved. The integration strength (between the layers) of tantalum/agarose scaffolds were on par with, or exceeded, values reported in the literature, but remained below native levels.

EXAMPLE 2

Cell Isolation and Culture: Immature Chondrocytes

Articular cartilage was harvested from bovine carpometacarpal (CMC) joints of freshly slaughtered 1-3 week old calves. Three to five joints were used for each study and cells were pooled from all joints. Cartilage chunks were digested in DMEM with 390 U/ml collagenase type VI for 11 hours at 37° C. with stirring. The resulting cell suspension was then filtered through a 70 μm pore-size mesh and sedimented in a bench top centrifuge for 10 minutes at 1000×g. Viable cells were counted using a hemocytometer and trypan blue.

One volume of chondrocyte suspension (at $60 \times 10^6$ cells/ml) was then mixed with an equal volume of 4% low-melt agarose (Type VII, Sigma) at 37° C. to yield a final cell concentration of $30 \times 10^6$ cells/mL in 2% agarose. To create cell-seeded scaffolds for chondral implants (containing chondrocytes and gelable scaffold material, without any attached porous substrate), the suspension of chondrocytes and agarose was cast into slabs and cored using a sterile disposable punch to final dimensions of about 4 mm diameter and about 2.3 mm thickness. To create cell-seeded scaffolds for osteochondral implants (containing the chondrocytes and gelable scaffold material secured to a biocompatible substrate), 60 μL of the chondrocyte/agarose suspension was poured into the cylindrical wells of a custom mold. Biocompatible porous osteochondral substrates immersed in the chondrocyte/agarose suspension from above to the desired depth (adjusted using a temporary retaining ring). With this technique a multi-layered construct was formed with the following dimensions: a 2 mm agarose-only top region, a 2 mm agarose plus substrate interface region, and a 2 mm substrate-only region.

The cell-seeded scaffolds were cultured in chemically-defined medium containing high-glucose DMEM Dulbecco's Modified Eagle's Medium supplemented with 1×PSF (100 units/ml penicillin, 100 µg/ml Streptomycin, 0.25 µg/ml Fungizone (Amphotericin B)), 0.1 µM dexamethasone, 50 µg/mL ascorbate 2-phosphate, 40 g/mL L-proline, 100 µg/mL sodium pyruvate, and 1×ITS+premix (insulin, human transferrin, and selenous acid). The chemically defined medium was further supplemented with 10 ng/mL of TGF-α3 for the first 14 days of culture. The growth medium was changed every other day.

EXAMPLE 3

The Beneficial Effect of Delayed Compressive Loading on Tissue-engineered Cartilage Constructs Cultured with TGF-Beta3

The objective of these studies was to determine whether the functional properties of tissue-engineered cartilage constructs cultured in a chemically-defined medium supplemented briefly with TGF-β3 could be enhanced with the application of dynamic deformational loading. The application of dynamic compressive loading (DL) within appropriate ranges of magnitude and frequency can be a beneficial tool for the functional tissue engineering of articular cartilage. It has been shown to increase synthesis of cartilage ECM components such as proteoglycans, collagens, and other matrix elements using a variety of loading apparatuses and culture systems when compared to control constructs maintained in free-swelling (FS) culture. The effect of dynamic loading is influenced by other factors in the tissue-engineering system such as the choice of scaffold, the formulation of feed media, and cellular factors such as species, age, and seeding density, and therefore protocols must be developed for a given set of experimental conditions.

It has been shown that temporal supplementation with transforming growth factor 3 (TGF-β3) (a 2-week exposure to TGF-β3 followed by 6 additional weeks of culture in medium substantially free of TGF-β3) in free-swelling, serum-free cultures of chondrocyte-laden agarose hydrogel constructs resulted in the development of constructs possessing cartilage-like compressive mechanical properties ($E_Y$>800 kPa). These values are significantly higher than modulus values obtained for engineered cartilage using any other culture system over the same culture duration; the only comparable outcome previously required over 7 months of continuous cultivation to develop similar properties. Prior to the current study, however, there was no data showing how chondrocyte-seeded constructs would respond to the application of dynamic loading under these media conditions.

In the present study, dynamic deformational loading applied concurrently with TGF-β3 supplementation yielded significantly lower (−90%) overall mechanical properties when compared to free-swelling controls. In contrast, the same loading protocol applied after discontinuation of the TGF-β3 supplementation resulted in significantly increased (+10%) overall mechanical properties relative to free-swelling controls. Equilibrium modulus values reached 1,306±79 kPa and glycosaminoglycan (GAG) levels reached 8.7±1.6% w/w during a 8 week culture period and are similar to host cartilage properties (994±280 kPa, 6.3±0.9% w/w). Thus, one strategy for the functional tissue engineering of articular cartilage, particularly to accelerate construct development, may incorporate sequential application of different growth factors and applied deformational loading.

Materials and Methods

A. Experimental Design. Three studies are discussed in this example (see FIG. 19). Study 1 examined the effect of temporal supplementation of TGF-β3 to the basal media; Study 2 examined the effect of dynamic deformational loading applied concurrently with TGF-β3 supplementation; and Study 3 examined the effect of dynamic deformational loading applied non-concurrently with TGF-β3 supplementation (i.e., dynamic deformational loading was initiated only after TGF-β3 supplementation was discontinued). Each study was performed independently, using individual cell isolations pooled from different animals. To ensure consistency, Study 3 was repeated twice and results have been pooled.

Figure 19:
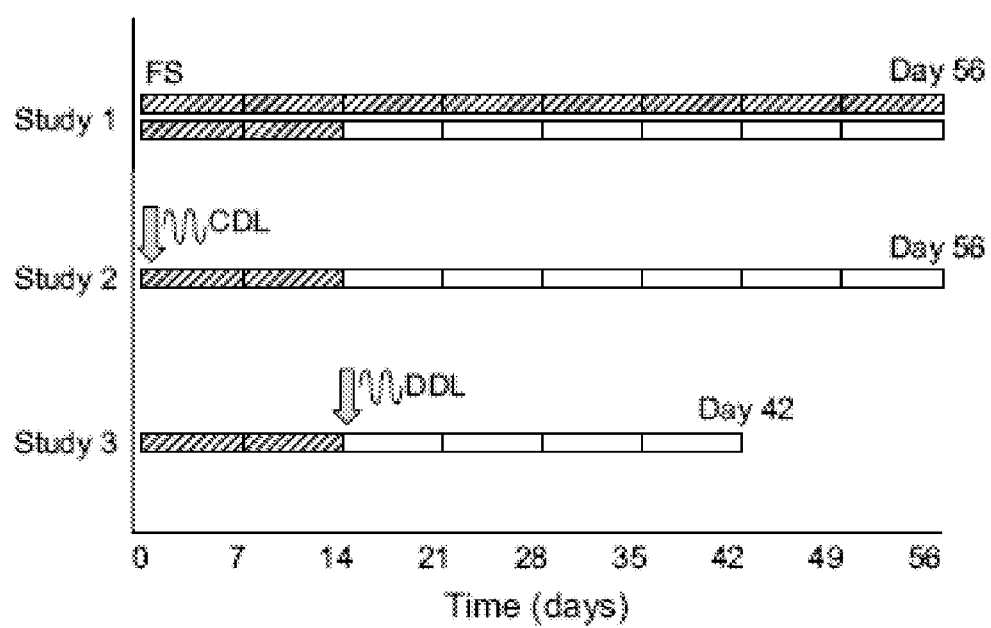
FIG. 19 is a schematic diagram representing the experimental design for Example 3, which discusses the beneficial effect of delayed compressive loading on tissue-engineered cartilage constructs cultured with TGF-beta3.

The timeline of the studies are detailed in FIG. 19. Dynamic deformational loading was initiated at the days indicated by the arrow (concurrent deformational loading (CDL)). The culture medium was supplemented with TGF-β3 during the periods indicated by hatch marks. Thus, there were two variables in the studies: 1) the day on which TGF-3 supplementation was discontinued, and 2) the day on which dynamic deformational loading of the constructs was initiated.

In Study 1 (n=4 per group), TGF-3 was supplemented to the media either for the first 14 days only (discontinuous) or it was supplemented throughout the duration of the study (continuous). There was no loading introduced to these developing constructs at any time.

Based on the results of Study 1, a protocol of discontinuous TGF-β3 supplementation was adopted for both Study 2 and Study 3.

In Study 2 (n=5 per group), dynamic deformational loading was initiated on day 0 and was continued throughout the culture period.

In Study 3 (n=8 per group), dynamic deformational loading was initiated on day 14 (delayed until the day TGF-3 was discontinued). In all studies, dynamic deformational loading is abbreviated CDL when initiated at day 0, and DDL when delayed until after the discontinuation of TGF-3. A follow up study (n=5 per group) was also performed with loading initiated on day 0 on the basal media without TGF-β3.

B. Cell Isolation. Articular cartilage was harvested from bovine carpo-metacarpal (CMC) joints of freshly slaughtered 2-3 month old calves. Three to five joints were used for each study and cells were pooled from all joints. Cartilage was rinsed in high-glucose Dulbecco's Modified Essential Medium (hgDMEM) supplemented with 5% fetal bovine serum (FBS), amino acids (0.5× minimal essential amino acids, 1× nonessential amino acids), buffering agents (10 mM HEPES, 10 mM sodium bicarbonate, 10 mM TES, 10 mM BES), and antibiotics (100 U/ml penicillin, 100 µg/ml streptomycin). The cartilage chunks were then combined and digested in DMEM with 390 U/ml collagenase type VI for 11 hours at 37° C. with stirring. The resulting cell suspension was then filtered through a 70 µm pore size mesh and sedimented in a bench top centrifuge for 10 minutes at 1000×g. Viable cells were counted using a hemocytometer and trypan blue.

One volume of a chondrocyte suspension (at 60×10$^6$ cells/ml) was then mixed with an equal volume of 4% low-melt agarose (Type VII, Sigma) at 37° C. to yield a final cell concentration of 30×10$^6$ cells/ml in 2% agarose. The chondrocyte/agarose mixture was cast into slabs and cored using a sterile disposable punch to final dimensions of 0.3 cm diameter and 0.23 cm thickness (0.016 cm$^3$). Constructs were maintained in culture in a chemically-defined serum-free growth medium for 42 days or up to 56 days depending on the study (See FIG. 19). The chemically-defined serum-free growth medium consisted of hgDMEM supplemented with 1×PSF (100 units/ml penicillin, 100 µg/ml Streptomycin, 0.25 µg/ml Fungizone (Amphotericin B)), 0.1 µM dexamethasone, 50 µg/ml ascorbate 2-phosphate, 40 µg/ml L-proline, 100 µg/ml sodium pyruvate, and 1×ITS+ (insulin, human transferrin, and selenous acid). Growth medium was changed every three days and maintained at a cell/media volume ratio of less than 1 million cells/ml media. In some experiments growth medium was further supplemented with 10 ng/ml TGF-β3 for either the first 14 days of culture or the entire culture period as shown in FIG. 19.

C. Loading Protocol. The prescribed loading protocol consisted of a nominal 5% dynamic strain (10% peak-to-peak deformation) above a 10% tare strain in unconfined compression with impermeable platens loading at 1 Hz frequency, for 3 hrs/day, 5 days/week (as had been previously found to be optimal for media formulations containing FBS). The duty cycle consisted of 3 hrs of continuous loading followed by 21 hrs of rest. Deformational loading was carried out at 37° C. and 5% $CO_2$ in a humidified incubator. FS controls were positioned adjacent to the loading device.

Figure 20:
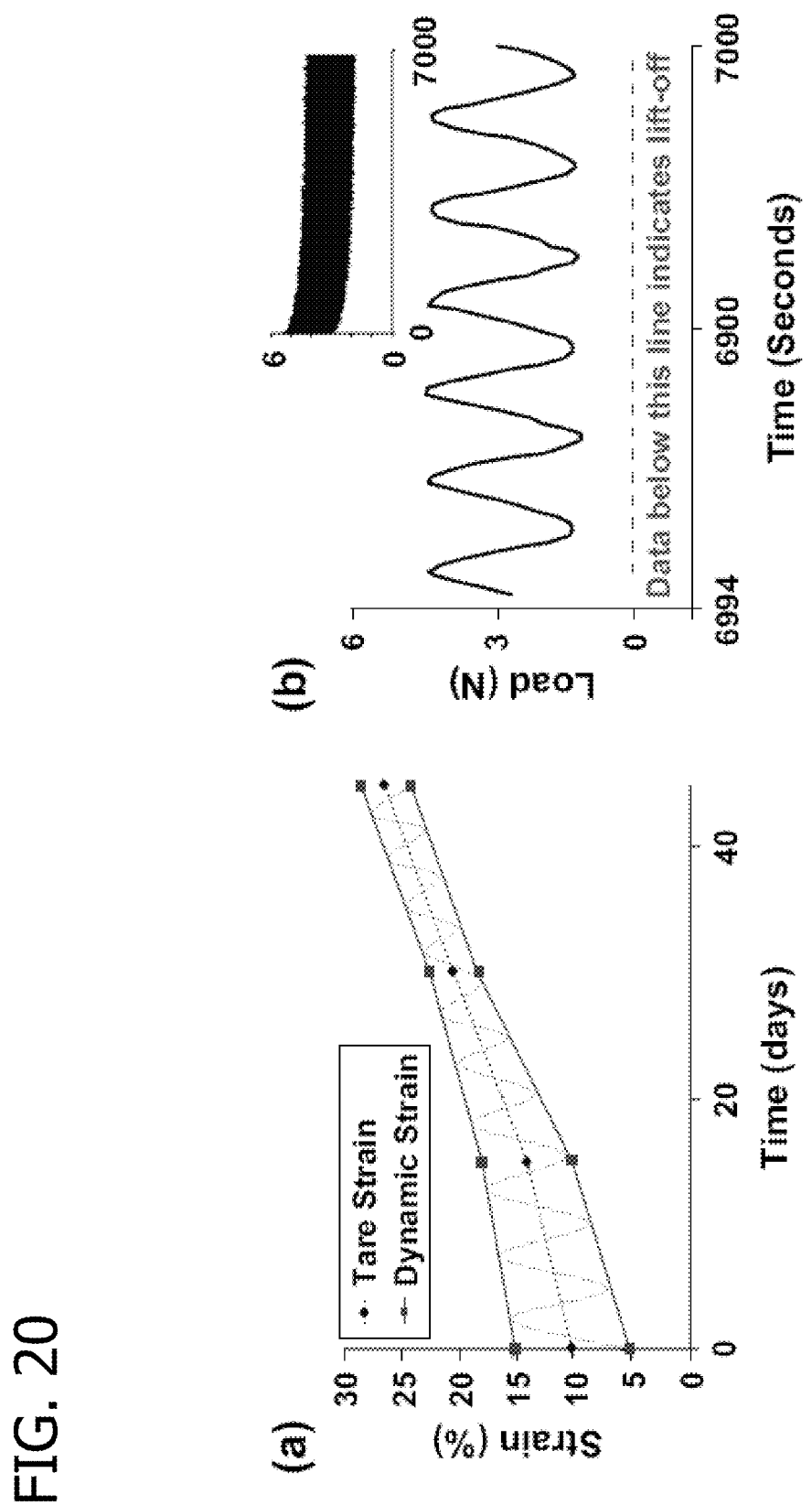
FIG. 20 includes graphical results of experiments.

The load and displacement profiles delivered by the bioreactor were analyzed in a small sample of specimens at the completion of all the experiments. In practice, the applied sinusoidal displacement had a consistent frequency of 1.05 Hz, with a total harmonic distortion of 6.03±0.95%. Due to inherent compliance of the loading bioreactors, the applied strain amplitude decreased over the culture period, as tissue elaboration produced specimens with increasing stiffness; the dynamic strain amplitude started at 5% and tapered to 2% by day 42 in culture (4% peak-to-peak). This compliance, coupled with the increasing tare strain resulting from growing construct thickness, had the beneficial effect of compensating passively for the increasing construct stiffness to prevent any loading platen lift-off through the entire culture period (see FIG. 20). FIG. 20(a) shows the loading profile adjusted for system compliance delivered by the bioreactor over time in culture. Dotted line shows increasing tare strain as a result of increasing tissue thickness with time. Solid lines show decreasing applied dynamic strain as a result of tissue stiffening over time. FIG. 20(b) shows the representative load vs. time curve of tissue-engineered constructs on day 42. A load of zero would have indicated platen lift-off. Inset represents full curve.

C. Material Testing. Cylindrical constructs were tested in unconstrained compression using a custom computer-controlled testing system. Initially, a series of stress-relaxation tests were conducted for each sample to 5%, 10%, 15%, and 20% strain and the Young's modulus ($E_Y$) of the construct was calculated from the equilibrium stress at each strain value and from the initial cross-sectional area. Since the resulting $E_Y$ was found to remain invariant across the strain amplitudes tested, the remaining samples were tested at 10% strain only and at a strain rate of 0.05% strain/sec after an initial 0.02 N tare load. The unconstrained dynamic modulus was also measured, after reaching stress-relaxation equilibrium to 10% strain, by superimposing 2% strain at 1 Hz. Tests of static and dynamic compressive properties were selected since the normal physiological loading mode of cartilage is compressive. More specifically, the most functionally relevant mechanical property is the dynamic modulus in compression, since joint loading is typically intermittent.

D. Biochemical Content. The biochemical content of each sample was assessed by first measuring sample wet weight, lyophilizing for 72 hours, and then measuring the sample dry weight. Gross water content was determined from the difference. Once dry, the samples were digested in proteinase-K overnight at 56° C. Aliquots of digest were analyzed for GAG content using the 1,9-dimethylmethylene blue dye-binding assay. A further aliquot was acid hydrolyzed in 12 N HCl at 110° C. for 16 hours, dried over NaOH, and resuspended in assay buffer. Ortho-hydroxyproline (OHP) content was then determined via a calorimetric assay by reaction with chloramine T and dimethylaminobenzaldehyde, scaled for microplates. OHP content was converted to total collagen content using the conversion of 1:7.64 ratio of OHP:Collagen. DNA content was determined using the PicoGreen (Molecular Probes) assay following the manufacturer's standard protocols. Each biochemical constituent (GAG and collagen) was normalized to tissue wet weight.

E. Histological Analysis. Samples were fixed in acid formalin ethanol, paraffin embedded, sectioned (8 µm thick), and stained with either Safranin O (1% in $dH_2O$, pH 6.7) to view proteoglycan distribution, Picrosirius Red to view collagen distribution, or hematoxylin and eosin to view cell and tissue morphology. Samples were also stained for Type II collagen as follows: sections were digested in 0.5 mg/ml of testicular hyaluronidase, swollen in 0.5 M of acetic acid, blocked in 10% normal goat serum (NGS) and labeled with 10% NGS containing monoclonal primary antibody for types I and II collagens (Developmental Studies Hybridoma Bank). Non-immune controls were incubated in 10% NGS alone. Alexa 488-conjugated goat anti-mouse secondary antibody labeling and propidium iodide nuclear counterstaining were performed to visualize the ECM and cells, respectively. After staining, the slides were coverslipped and sections were analyzed using an inverted microscope with an Olympus Fluoview confocal system with dual wavelengths excitation at 488 and 568 nm (20× to 100×-oil objective lens).

F. Statistics. Statistics were performed with the Statistica (Statsoft) software package. Each data point represents the mean and standard deviation of four or five samples. Groups were examined for significant differences by two-way analysis of variance (ANOVA), with $E_Y$, G* (dynamic modulus), GAG, DNA, or OHP as the dependent variable, and time in culture and loading condition as the independent variables. Tukey's Honest Significant Difference Test (HSD) post-hoc tests were carried out with a statistical significance set at α=0.05.

III. Results

A. Study 1: The Effect of Transient TGF-β3 Exposure on Free Swelling Constructs

Figure 21:
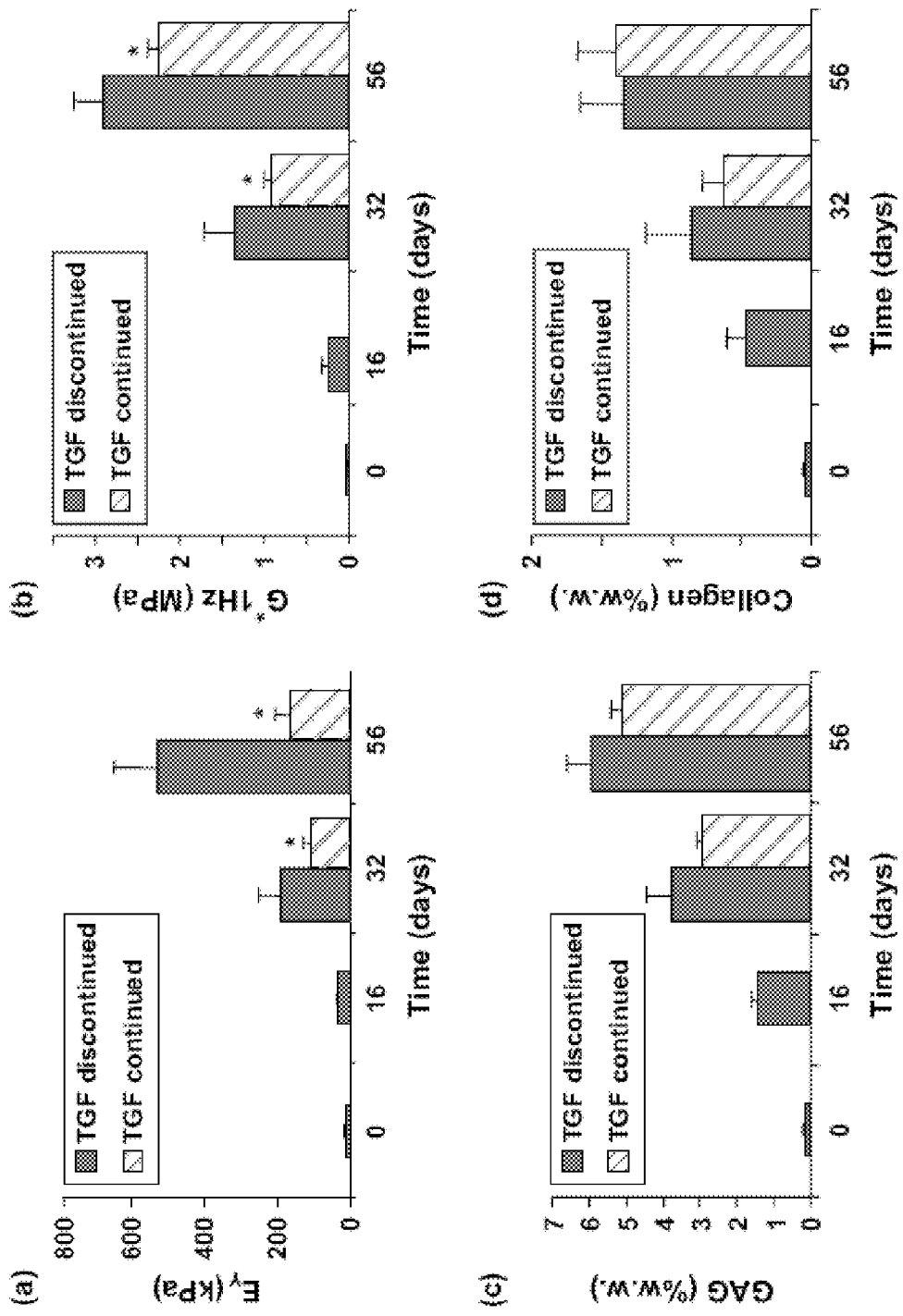
FIG. 21 includes graphical results of experiments.

Constructs developed significantly different mechanical properties and biochemical composition depending on culture condition and time. In Study 1, performed in free-swelling cultures, constructs that were transiently exposed to TGF-β3 elaborated significantly stiffer tissue ($E_Y$=528±122 kPa, G*=2.9±0.3 MPa) than constructs that were exposed to TGF-β3 continuously ($E_Y$=165±42 kPa, G*=2.2±0.1 MPa) (FIG. 21(a), (b), day 56). However, no differences were observed in GAG (TGF discontinued=6.0±0.6% w/w, TGF continued=5.1±0.3% w/w) or collagen (TGF discontinued=1.3±0.3% w/w, TGF continued=1.4±0.3% w/w) content between these groups (FIG. 21(c),(d)). In FIG. 21, *p<0.05 for TGF continued vs. TGF discontinued (n=4).

Figure 22:
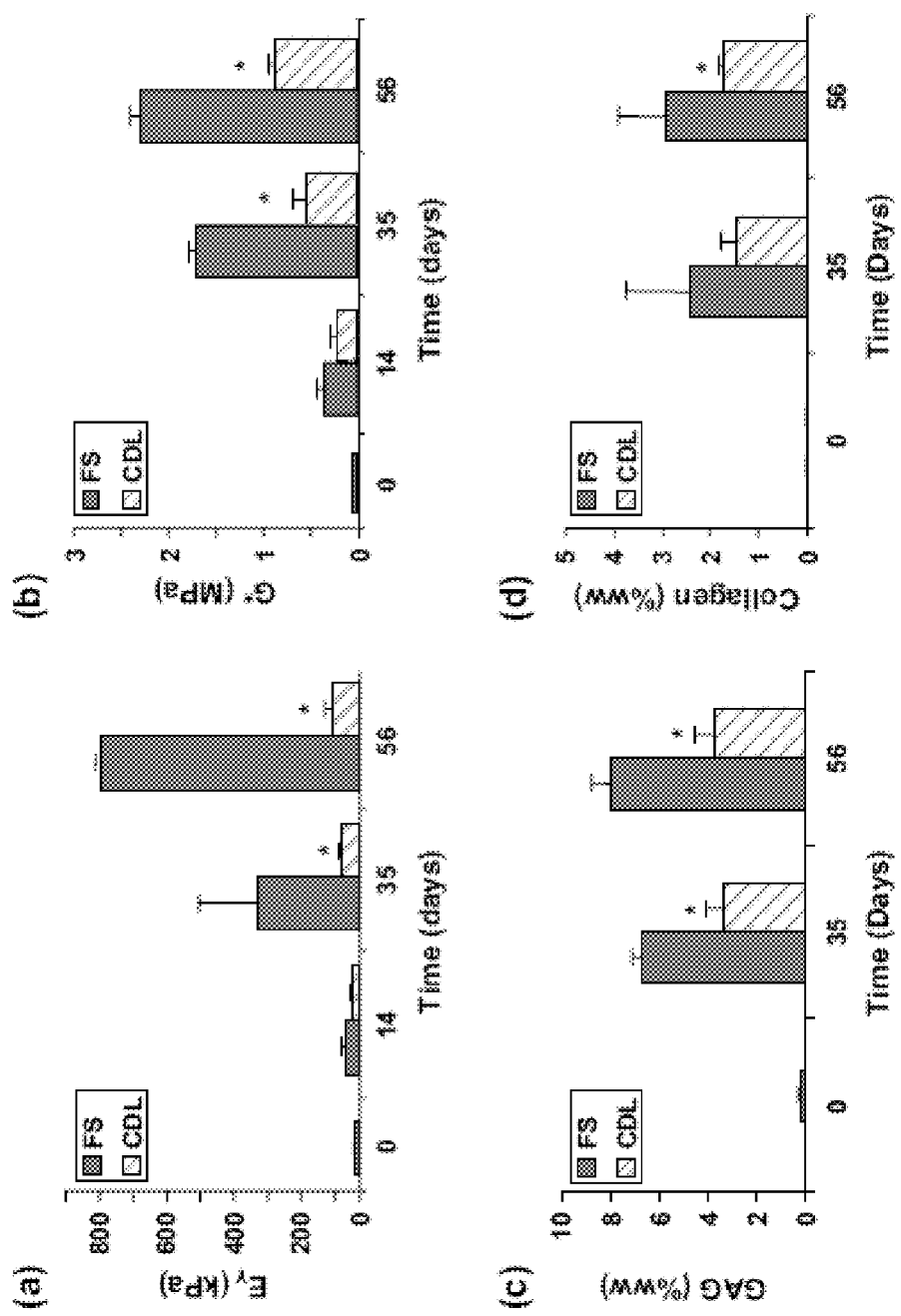
FIG. 22 includes graphical results of experiments.

B. Study 2: The Effect of Transient TGF-β3 Exposure on Dynamically Loaded Constructs The results of Study 2 demonstrate the detrimental effects of dynamic deformational loading in the concurrent presence of TGF-β3 (FIG. 22): when loading was applied to constructs in basal media with TGF-β3, the CDL group achieved significantly lower mechanical properties ($E_Y=78\pm22$ kPa, $G^*=0.88\pm0.08$ MPa) compared to the FS control ($E_Y=780\pm8$ kPa, $G^*=2.3\pm0.1$ MPa) (FIG. 22(a), (b), day 56). The GAG content and collagen content also showed significantly lower values in CDL versus FS (GAG: CDL=3.7±0.8% w/w, FS=8.0±0.8% w/w; collagen: CDL=1.75±0.1% w/w, FS=3.16±1.0% w/w; FIG. 22(c), (d), day 56). In FIG. 22, *p<0.05 for FS vs. CDL (n=5).

C. Study 3: Temporal Application of Dynamic Deformational Loading

Figure 23:
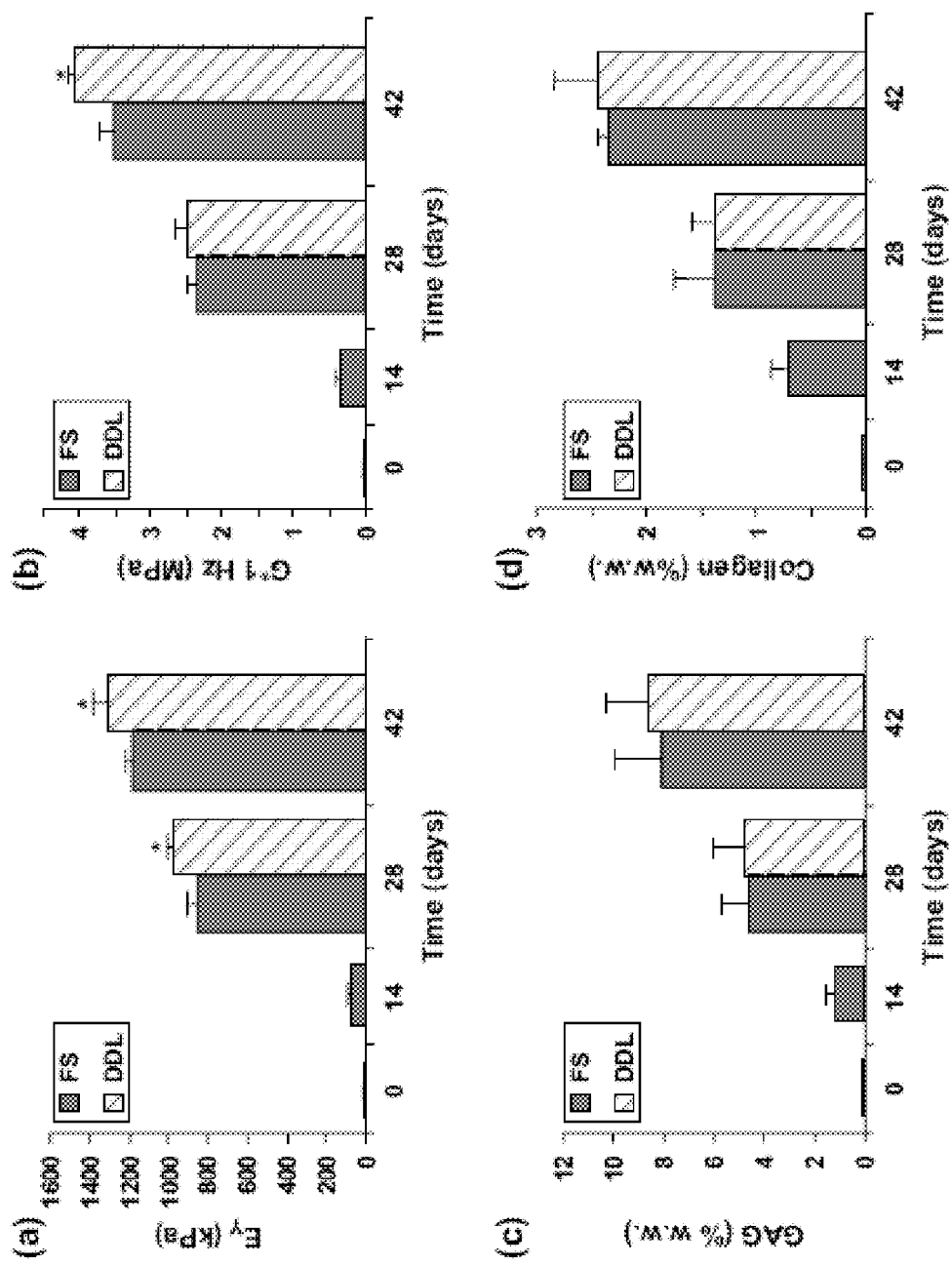
FIG. 23 includes graphical results of experiments.

The results of Study 3 show that when loading was applied after the discontinuation of TGF-β3, the DDL group achieved mechanical properties ($E_Y=1,306\pm79$ kPa, $G^*=4.1\pm0.1$ MPa) significantly higher than FS ($E_Y=1,178\pm40$ kPa, $G^*=3.5\pm0.2$ MPa) (FIG. 23(a), (b), day 42). However, no differences were observed in GAG (DDL=8.6±1.7% w/w, FS=8.1±1.8% w/w) or collagen (DDL=2.4±0.4% w/w, FS=2.3±0.1% w/w) content (FIG. 23 (c), (d)). In FIG. 23, *p<0.05 for FS vs. DDL (n=8).

Figure 24:
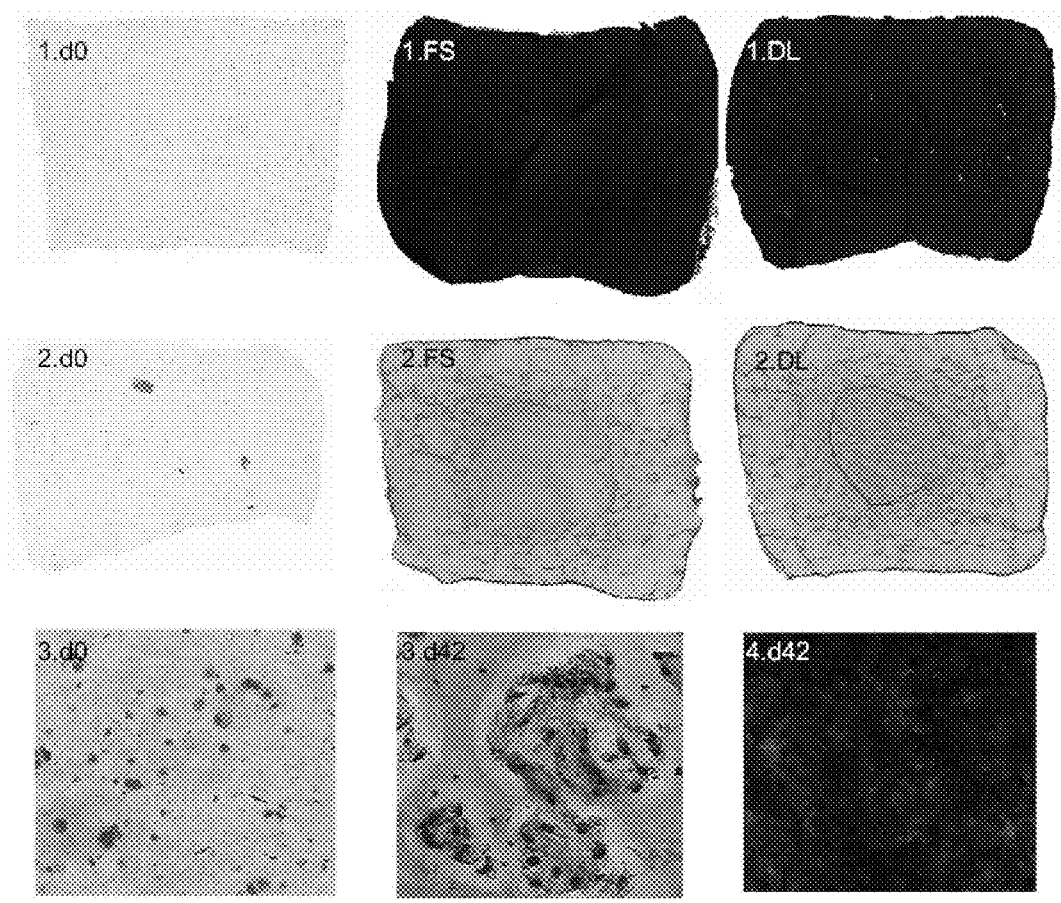
FIG. 24 contains photographs from histological studies.
Figure 25:
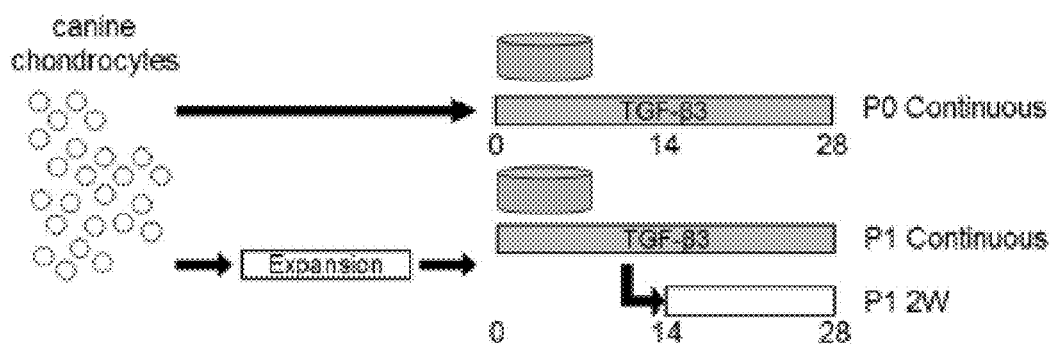
FIG. 25 is a schematic diagram representing the experimental design for Example 4, which shows that primed mature chondrocytes can develop an engineered cartilage tissue with physiologic properties.

Histological analysis confirmed abundant deposition of GAG throughout the constructs and a uniform distribution of type II collagen (FIGS. 24(1) and (2)) with little or no staining for type I collagen (not shown). Staining indicated that cells multiplied in localized pockets throughout the constructs (FIG. 24(3)). Cells proliferated with time, increasing on average 3-fold from day 0 concentrations, but did not differ significantly between any groups reported here. In FIG. 24, the (1) panels show Safranin O staining for GAG, the (2) panels show Picrosirius Red staining for collagen, the (3) panels show hematoxylin and eosin staining for visualization of local multiplication of cell nuclei (Mag. 40×), and the (4) panel shows immunohistochemical staining for type II collagen. All slides were taken from study 3 on either day 0 or day 42 with either free-swelling (FS) or dynamically-loaded (DL) groups.

For comparison, the mechanical and biochemical properties of juvenile CMC articular cartilage were also measured (n=5) and were found to be $E_Y=994\pm280$ kPa, $G^*$ (at 1 Hz)=13±2.5 MPa, GAG=6.3±0.9 (% w/w), 24±3.5 (% d.w.), collagen=16±0.5 (% w/w), 66±5.5 (% d.w.). While $E_Y$ for DDL and FS for Study 3 equaled or exceeded that of native cartilage by day 28 (FIG. 23(a)), $G^*$ was at most 32% that of native values at day 42 (FIG. 23(b)). Similarly GAG values equaled or exceeded those of native cartilage in DDL and FS groups (FIG. 23(c)), but collagen content was only 15% that of native tissue (FIG. 23(d)).

IV. Discussion

In this investigation a protocol of transient supplementation of serum-free media with TGF-β3 was adopted and a regimen of dynamic deformational loading was applied, the timing of which was adjusted towards achieving the most robust mechanical properties. The findings of this study indicate that coordination of the timing (introduction and duration) of the application of an appropriate chemical stimulus as well as the timing of the introduction of mechanical stimuli represents a strategy to optimize engineered tissue growth (i.e., a sequential loading protocol).

In Study 1, earlier results finding that discontinuation of TGF-β3 supplementation after two weeks in culture yields much better material properties than continuous supplementation were confirmed (FIG. 21). In Study 2, it was found that dynamic loading initiated at the same time as TGF-β3 supplementation yields significantly poorer properties than the free-swelling control group, after discontinuation of supplementation (FIG. 22). However, the application of deformational loading initiated after culturing with growth factor TGF-β3 for 2 weeks (Study 3) yields significantly stiffer chondrocyte-seeded agarose constructs than free-swelling controls. Using this sequential loading protocol, engineered constructs continued to display the dramatic improvement in properties associated with the removal of the growth factor (Studies 1 and 2) while benefiting from the deformational loading protocol. Young's modulus and GAG levels achieved values similar to those of native cartilage after as little as 28 days in culture (FIG. 23(a)). Dynamic modulus values, which are more representative of the functional tissue properties, however, remain at 32% of those manifested by native cartilage, after 42 days in culture (FIG. 23(b)). As has been shown both theoretically, and in vivo, dynamic modulus values are largely influenced by collagen content and organization as well as construct permeability whereas the equilibrium modulus is influenced to a greater degree by GAG content.

Related to this observation, collagen levels for constructs in all the studies presented here remained relatively low (FIG. 21(d), FIG. 22(d), FIG. 23(d)). This suggests that application of dynamic loading as well as the temporary supplementation of TGF-β3 has a much greater effect on GAG production compared to collagen production. In fact, the increase in the equilibrium compressive modulus over time of developing constructs can be attributed almost entirely to the increase in GAG levels. While the average content of GAG and collagen were not statistically different between DDL versus FS constructs in Study 3, the compressive moduli were significantly stiffer (~15%) for DDL constructs (FIG. 23(a), (b)).

The results of this study address a number of important issues related to functional tissue engineering of articular cartilage. The most positive outcome is the finding that temporary supplementation of TGF-β3 followed by dynamic loading can produce an equilibrium modulus and GAG content which match those of native tissue over a culture period of 4 to 6 weeks only; the dynamic modulus and collagen content remain lower than in native tissue, but are as good as, or better than reported in previous studies.

EXAMPLE 4

Primed Mature Chondrocytes can Develop an Engineered Cartilage Tissue with Physiologic Properties In previous studies, mature chondrocytes exhibited diminished proliferative and synthetic ability compared to younger cells. In this example, it is shown that growth factor treatment during passaging of adult cells leads to an engineered cartilage tissue with physiologic compressive stiffness.

I. Materials and Methods

A. Cell culture. Canine chondrocytes were isolated from shoulder and knee cartilage of adult mongrel dogs (2-5 years old, 90+ lbs.) according to the method described above. Cells were either used immediately after isolation or passaged in DMEM with 10% FBS, 1 ng/mL TGF-β1, 5 ng/mL FGF-2, and 10 ng/mL PDGF-BB. Primary (unpassaged) or passaged chondrocytes were suspended in 2% agarose at $30\times10^6$ cells/mL. Disks created as described above and having diameters of 0.4 mm and thicknesses of 1.5 mm (ø4.0×1.5 mm) were cultured in 35 mL of chondrogenic media and ascorbate at 37° C. and 5% $CO_2$. More specifically, the media consisted of hgDMEM supplemented with 1×PSF (100 units/ml penicillin, 100 µg/ml Streptomycin, 0.25 µg/ml Fungizone (Amphotericin B)), 0.1 µM dexamethasone, 50 µg/ml ascorbate 2-phosphate, 40 μg/ml L-proline, 100 μg/ml sodium pyruvate, and 1×ITS+ (insulin, human transferrin, and selenous acid).

Primary chondrocyte-seeded hydrogels were cultured with 10 ng/mL TGF-β3 throughout the culture period ("P0 Continuous"). Passaged chondrocyte constructs were exposed to TGF-β3 either continuously ("P1 Continuous") or only for the first 2 weeks in culture ("P1 2W"). Media was changed every 48 h. A schematic of the experimental design is shown in 25.

B. Mechanical Testing. Young's modulus ($E_Y$) and dynamic modulus ($G^*$) of samples (n=4-5 per group) were calculated from static and 0.1 Hz unconfined compression testing on day 0, 14, and 28. Following testing, constructs were weighed wet and frozen for biochemical analysis.

C. Biochemical Analysis. GAG and collagen contents were measured for each sample and normalized to construct wet weight (% w/w) according to the methods described above.

D. Statistics. Data were analyzed using 2-way ANOVA, with time and growth factor treatment as factors. Fisher LSD post-hoc test was used to determine significant differences (α=0.05).

II. Results

Figure 26:
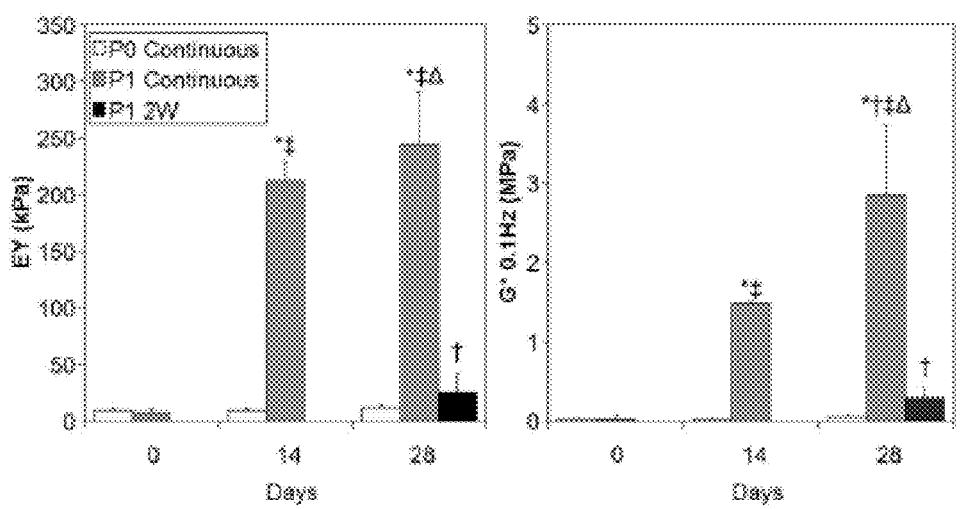
FIG. 26 includes graphical results of experiments.
Figure 27:
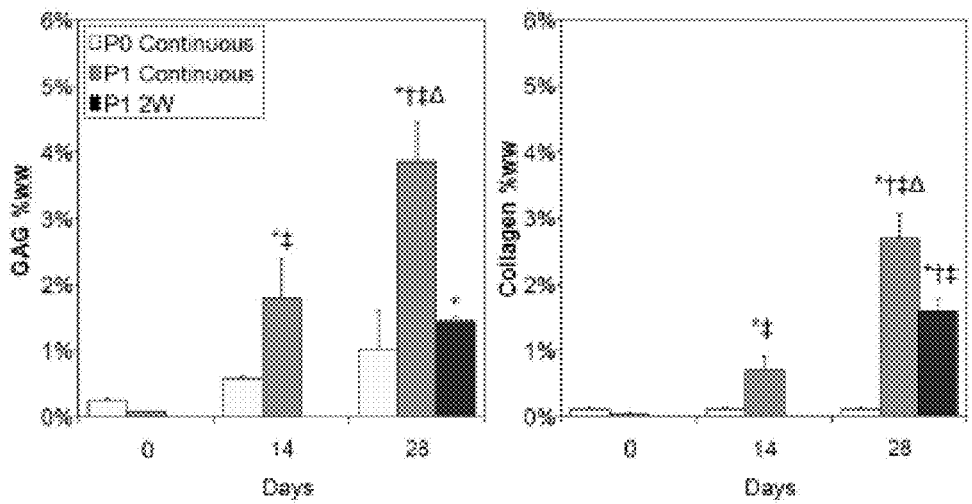
FIG. 27 includes graphical results of experiments.

Canine chondrocytes grown in monolayer culture with the growth factor cocktail reached confluence in 11 days, with an ~8× increase in cell number. P0 Continuous constructs showed no changes in measured tissue properties over time in culture, with only an increasing trend in GAG content (d28: 1.0±0.6% w/w vs. d0: 0.2±0.1% w/w, p=0.583) (FIG. 27). P1 chondrocyte-seeded hydrogels increased in stiffness and biochemical content after 14 days in culture (FIGS. 26, 27). When compared to day 14, P1 2W constructs on day 28 exhibited increased collagen content (FIG. 27), but significantly diminished mechanical properties (FIG. 26). P1 Continuous constructs on day 28, however, were the stiffest (FIG. 26; $E_Y$ 243.7±57.1 kPa, $G^*$ 2.85±0.88 MPa) and possessed the most matrix content (FIG. 27; GAG 3.9±0.7% w/w, collagen 2.7±0.4% w/w) of all groups.

FIG. 26 shows the Young's modulus (left) and dynamic modulus (right) of canine engineered cartilage. *$p<0.05$ vs. d0, †$p<0.05$ vs. d14, ‡$p<0.05$ vs. P0 Continuous, Δ$p<0.05$ vs. all groups at all time points.

FIG. 27 shows the GAG (left) and collagen (right) content of canine engineered cartilage. *$p<0.05$ vs. d0, †$p<0.05$ vs. d14, ‡$p<0.05$ vs. P0 Continuous, Δ$p<0.05$ vs. all groups at all time points.

III. Discussion

The protocol used resulted in the successful expansion of mature chondrocytes that could form an engineered cartilage tissue with a Young's modulus in the physiologic range for native canine cartilage (~200–500 kPa). The measured compressive stiffness and GAG content represent the highest reported values for engineered cartilage formed from mature chondrocytes. Canine chondrocytes have been shown to rapidly dedifferentiate during passaging without growth factor treatments and were therefore not included as a group in this study. The best results were achieved with continuous TGF-β3 treatment, consistent with mature bovine cells. This indicates that the use of TGF-β3 during 3D culture is translatable between adult cells of different species.

EXAMPLE 5

In Vivo Implantation of Chondral and Osteochondral Tissue-Engineered Constructs in a Canine Model With focus on development of constructs suitable for repair of focal defects in the joint, cylindrical engineered osteochondral constructs resembling native osteochondral grafts of cartilage and underlying bone were developed. The advances in culture media formulation and development of the applied deformational loading protocol that are encompassed within the present invention have led to a robust culture protocol for cultivation of engineered tissue constructs with native properties of articular cartilage in less than 8 weeks. Together with an appropriate underlying substrate material, osteochondral constructs (stiffer than most described in the literature) with native chondral properties can be cultivated.

This example describes in vivo studies designed to assess the efficacy of the engineered tissues in a clinically-relevant large animal model. Chondral, osteochondral, and anatomically-shaped osteochondral constructs were developed. The engineered constructs used in these studies were produced using passaged, adult canine cells as described in the previous example and had native canine $E_Y$ and GAG levels.

I. Response of Canine Chondrocytes to Dynamic Deformational Loading

Figure 28A:
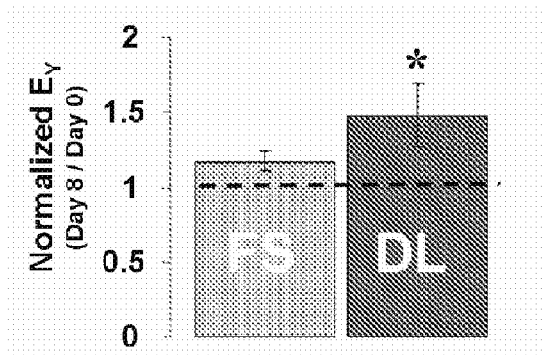
FIG. 28A includes graphical results of experiments.
Figure 28B:
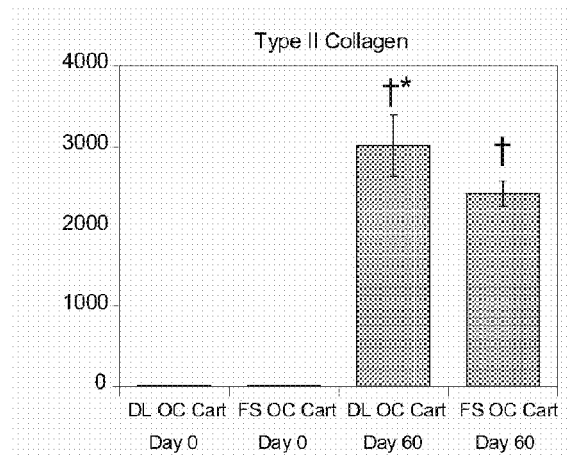
FIG. 28B includes graphical results of experiments.
Figure 28C:
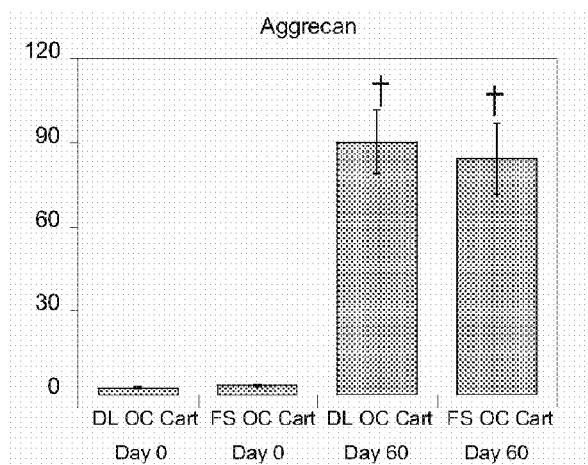
FIG. 28C includes graphical results of experiments.

FIGS. 28A-28C shows the response of engineered constructs containing canine chondrocytes to dynamic deformational loading. FIG. 28A shows that $E_Y$ was significantly increased when engineered canine agarose (chondral) constructs were subjected to dynamic deformational loading for three hours per day, five days per week, at 1 Hz (n=4/group). The dashed line represents native $E_Y$. FIG. 28B shows Type II collagen levels in osteochondral constructs containing canine chondrocytes. Type II collagen was significantly increased in the constructs subjected to dynamic deformational loading as compared to free-swelling controls. FIG. 28C shows that aggrecan gene expression was increased in osteochondral engineered constructs at 60 days, but that there was no difference in aggrecan expression in the constructs subjected to dynamic deformational loading as compared to free-swelling controls. †$p<0.05$ vs. day 0, *$p<0.05$ vs. FS.

II. In Vivo Implantation

Either chondral (Study A) or osteochondral (gel-tantalum, Study B) constructs were implanted in the femur of adult mongrel dogs. In all studies, arthroscopic assessment and synovial fluid arthrocentesis were performed at 6 weeks with digital radiography, MRI, synovial fluid arthrocentesis, and arthroscopy performed at the time of sacrifice. Tissue was harvested and samples separated for material testing and subsequent biochemical composition analyses or histology.

Figure 29:
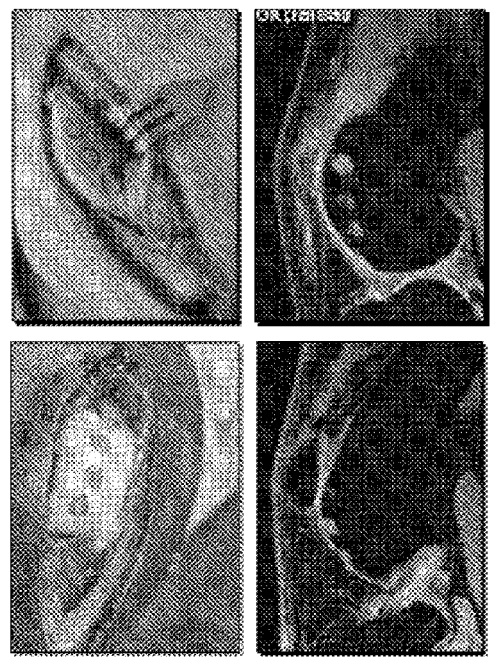
FIG. 29 contains peri-operative and MRI images of chondral constructs, drawings of bones depicting the approximate implantation locations of NLB and LB constructs, and graphical results of experiments.
Figure 29:
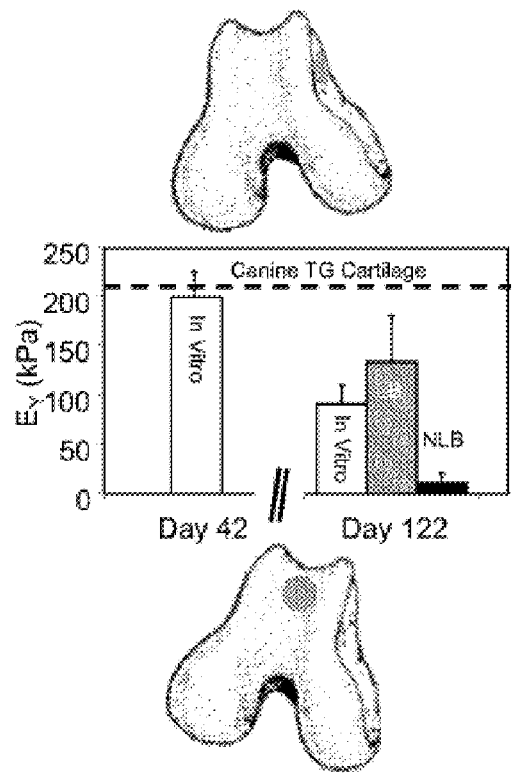

A. Study A: Chondral Implants. In these in vivo studies, three full-thickness 4 mm defects were aseptically drilled through the cartilage and subchondral bone plate in the trochlear groove or lateral aspect of the lateral trochlear ridge of the femur of adult mongrel dogs (~25 kg) to assess tissue repair with allogeneic chondrocyte-seeded engineered constructs possessing Young's moduli similar to native canine cartilage (FIG. 29). These constructs were cultured under free-swelling conditions with optimized chondrogenic media. Repair tissue in empty defects observed at 6 and 12-week arthroscopies was fibrous and/or fibrocartilaginous in appearance and did not restore surface congruity or cartilage volume in the defect site as was seen in implanted defects. Similarly, gross appearance of empty (control) defects showed incomplete filling with fibrous tissue (granulation tissue) whereas the sites receiving constructs showed good to excellent filling with hyaline-like tissue.

Chondral constructs in weight-bearing regions remained in place and appeared more hyaline-like. In contrast, constructs implanted in non-weight bearing regions exhibited some migration, exhibited significant subsidence and were weak in modulus (FIG. 29). For chondral constructs in weight-bearing regions, the GAG content dropped 5-fold and collagen content increased 4-fold from initial implantation values after 12 weeks in vivo. Specifically, GAG levels dropped from 4.0±0.7% (at implantation) to 0.8±0.6% (n=3, p<0.05) whereas collagen content increased from 3.3±0.4% w/w to 12.9±0.9% (n=3, p<0.05). For the non-weight-bearing constructs, GAG decreased to 0.8±0.3% w/w, whereas collagen increased to 7.1±2% w/w. The non-weight-bearing constructs also exhibited a significant 4-fold decrease in DNA. When maintained in culture for 122 days, constructs exhibited a decrease in modulus (FIG. 29) along with GAG that fell to 1.8±0.2% w/w (n=3, p<0.05), whereas collagen levels were maintained at 3.7±0.3% w/w.

FIG. 29 shows peri-operative and MRI images of chondral constructs and Young's modulus (n=2/group) of harvested constructs. Constructs were implanted on day 42 in vitro culture and harvested 80 days later, on culture day 122 (or 12 weeks in vivo). LB=load-bearing. NLB=non-load bearing. Drawings of bones depict the approximate implantation locations of NLB and LB constructs. The MRI images show that the implants are in place, with good maintenance of surface contour, and have the MRI appearance of surrounding normal cartilage.

These findings suggest that in vivo joint loading is important for engineered construct maintenance and remodeling in situ, and that collagen content of constructs can increase above those achievable in culture after implantation. From gross appearance and histology of unstained and H&E stained sections there is evidence of construct stability and early integration as suggested by the notable articular surface continuity associated with the entire perimeter of the construct.

B. Study B: Osteochondral Implants. For osteochondral constructs (FIG. 30A-30C), indentation testing of repaired tissues (performed on cylindrically cored, 6 mm diameter tissue-construct cores) revealed that implanted constructs were stiffer than empty defect fill tissue, but softer than surrounding trochlear groove cartilage. These results were stiffer compared to chondral only constructs. The GAG content for the respective constructs dropped from 3.7±1.2% w/w (at implantation) to 2.3±0.9% w/w for the filled defects. For comparison, unfilled defects had GAG levels of 0.77% w/w and adjacent cartilage had GAG levels of 8.13±1.2% w/w. There was no evidence of displacement in any of the grafts, but there was some variable subsidence and contractions. This was likely due to drilling down into and past the subchondral plate and an imperfect pressfit. The tissue appeared to range from fibrocartilage in some regions to hyaline-like cartilage in others. There was mild effusion in all joints, but this was consistent with surgery and there were no signs of infection, untoward immune response, or morbidity. The dogs scored well on lameness and comfortable range of motion tests and apposing cartilage surface looked normal on arthroscopic examination. These results suggest that in addition to anchoring engineered constructs, the use of osteochondral substrates reduce matrix loss found in chondral implants. Tissue-engineered osteochondral constructs yield stiffer tissue than both chondral and empty defects over a 12-week in vivo implantation period.

Figure 30A:
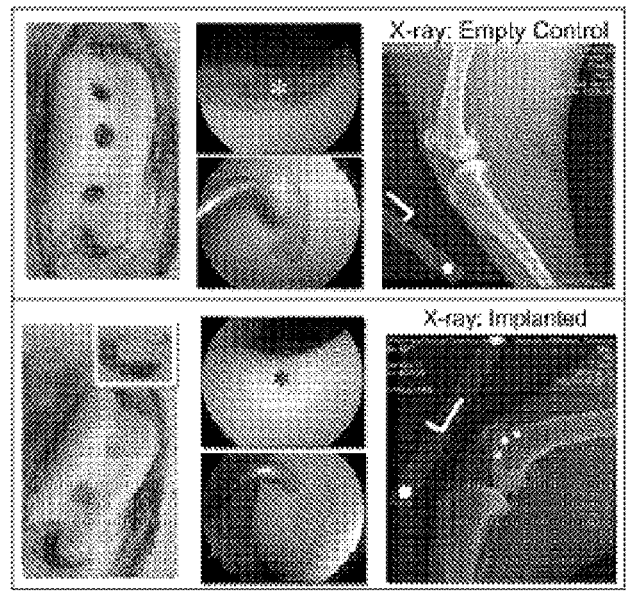
FIG. 30A shows intra-operative (left), arthroscopic (middle), and radiographic images (right) (12 weeks) of unfilled empty defect controls (top) and implanted osteochondral constructs (bottom)
Figure 30B:
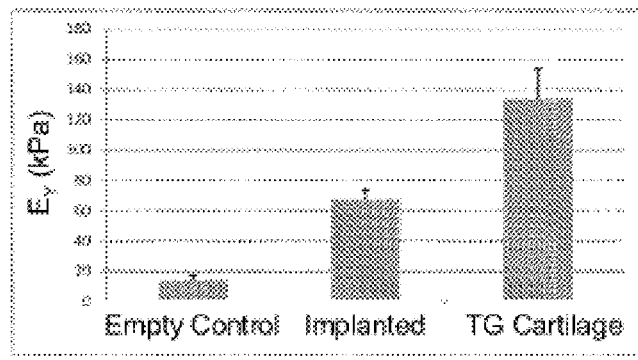
FIG. 30B includes graphical results of experiments.
Figure 30C:
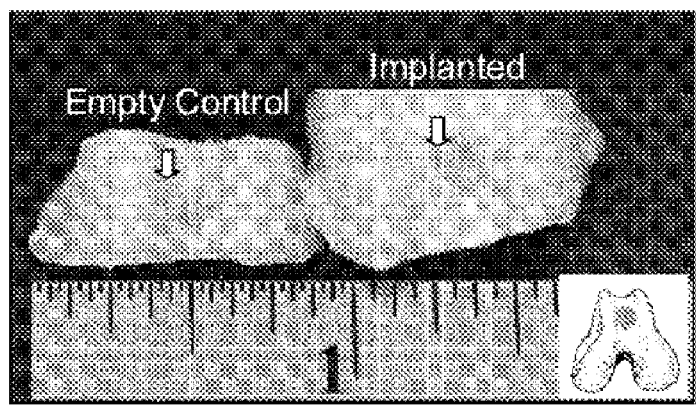
FIG. 30C is a gross image of an empty control and an implanted osteochondral construct.

FIG. 30A shows intra-operative (left), arthroscopic (middle), and radiographic images (right) (12 weeks) of unfilled empty defect controls (top) and implanted osteochondral constructs (bottom). FIG. 30B shows Young's moduli for empty controls, implanted osteochondral constructs, and canine trochlear groove (TG) cartilage. FIG. 30C is a gross image of an empty control and an implanted osteochondral construct. The arthroscopic images showing the implanted osteochondral constructs show hyaline-like cartilage in defects treated with the implants, with good maintenance of size, shape, location, and surface contour. The implants survived, stayed in place, and were functional.

C. Synovium and Synovial Fluid Analyses. In histological sections of harvested synovium (FIG. 31), lymphoid aggregates, giant cells, neutrophils and macrophages were not observed in any samples. Infiltrates of small numbers of lymphocytes and plasma cells along with marked hyperplasia were observed for the empty defect stifle and considered the only significant lesion of all samples. The lack of neutrophils in any of the sections suggests there was no inflammation, however it is possible that an inflammatory response occurred (and ended) prior to testing. As expected, the synovium in stifles undergoing arthrotomy for implant placement exhibited mild hyperplasia relative to the non-surgical control specimen. Only mild evidence of joint effusion was present in any dog, and cytologic examination revealed normal synovial fluid in all cases (e.g., few mononuclear cells [synovial lining cells] in proteinaceous background, no neutrophils, lymphocytes, or plasma cells). Together, these results suggest that intra-articular implantation of allogeneic chondrocyte-seeded agarose hydrogel constructs were well tolerated such that integration occurred with no clinical, radiographic, histologic, or cytologic evidence for untoward inflammatory or immune responses. In particular, there was no increased joint effusion (clear synovial fluid), arthrocentesis cytology was normal, and synovium histology for the implants was normal at 12 weeks.

FIG. 31 shows representative histology (H&E) of the synovium: (left 3 panels, hyperplasia: asterisks). As expected, the synovium in implanted knees exhibited mild hyperplasia due to surgery relative to non-surgical control. Empty defect knees exhibited prominent hyperplasia, with multiple layers of swollen synovial cells and fronds of papillary projections. For synovial cytology, plasma cell (white arrow) and some red blood cells were present (introduced during aspiration).

Thus, using agarose as the gelable scaffold material yielded high mechanical and biochemical values and there was no evidence of an inflammatory response to agarose in vivo.

D. Animal Lameness and Gross Appearance of Implant Sites of Chondral and Osteochondral Studies. Animal lameness was scored on a scale from 0 to 5, with 5 being severe. For chondral and osteochondral constructs (n=5 animals), all had normal gait at 12 weeks except one dog that had very mild grade 1 of 5 intermittent lameness. The single animal with empty control defects showed grade 2 of 5 lameness at 12 weeks. No animals had palpable joint effusion and synovial fluid was clear and viscous upon examination after arthrocentesis. Additionally, some construct migration was noted for non-load-bearing sites whereas load-bearing samples showed excellent integration with surrounding cartilage and underlying bone. More subsidence was observed for chondral constructs, further motivating the use of chondral constructs supported by a bone or bone-substitute base for optimal cartilage resurfacing. Based on subjective arthroscopic assessment and India ink staining, the opposing surface of the patella was normal in all cases with no evidence for cartilage "kiss" lesions (e.g., fibrillation or erosion). No constructs were observed to fail under in vivo loading.

EXAMPLE 6

Measuring the Diffusion Coefficient of a Gelable Scaffold Material

I. Materials and Methods
A. Hydrogel Fabrication. Sigma 2% type VII (VII) and 2% type IX (IX) agarose discs containing immature bovine chondrocytes at a final concentration of 30 million cells/ml were fabricated as described above and gelled at 25° C. and 4° C., respectively. Discs were cultured in serum-free, chemically-defined media, and TGF-β3 (10 ng/mL for the first 14 days of culture).
B. Diffusivity Measurement. Diffusion coefficients were measured by fluorescent recovery after photobleaching (FRAP). Constructs were incubated overnight in phenol red-free medium containing 0.5 mg/ml fluorescein isothiocynate (FITC)-conjugated 70 kDa dextran. This molecular weight is representative of large growth factors or matrix products commonly used or produced during culture. Each sample was then exposed to a high intensity monochromatic laser to induce localized photobleaching, and the recovery of fluorophores was modeled using Fick's law for one-dimensional diffusion with an initial Gaussian solute distribution to extract diffusion coefficients.
C. Mechanical Testing. Constructs were tested in unconfined compression with samples being loaded to 10% strain at a strain rate of 0.05% strain/sec, after an initial 0.02N tare load ($E_Y$). Dynamic modulus ($G^*$) was measured by superimposing 2% peak-to-peak sinusoidal strain at 0.1 Hz.
D. Biochemistry. Constructs were proteinase K-digested, and glycosaminoglycan (GAG), collagen, and DNA content were determined using the DMMB dye-binding assay, orthohydroxyproline (OHP) assay, and Picogreen dsDNA assay, respectively.
E. Histology. Samples were fixed in acid formalin ethanol and paraffin embedded. 8 μm thick sections were stained with Alcian Blue and Picrosirius Red for proteoglycan and collagen distribution.
F. Statistics. A one-way ANOVA ($\alpha=0.05$) with Tukey's HSD post-hoc tests was used to compare groups.

II. Results

Hydrogel compositions were selected to provide similar initial diffusion coefficients for the two different agarose types (~22 μm²/sec). Type VII agarose was significantly greater in initial modulus (Table 1).

TABLE 1

| Initial material properties of different types of agarose gel. | | |
|---|---|---|
| Agarose gel | Modulus (kPa) | Diffusion Coefficient (μm²/sec) |
| 2% VII (room) | 9.0 ± 3.2 | 22.4 ± 2.6 |
| 2% VII (cold) | 13.8 ± 2.5 | 21.0 ± 0.6 |
| 2% IX (cold) | 2.2 ± 0.6 | 21.2 ± 1.8 |

Figure 32:
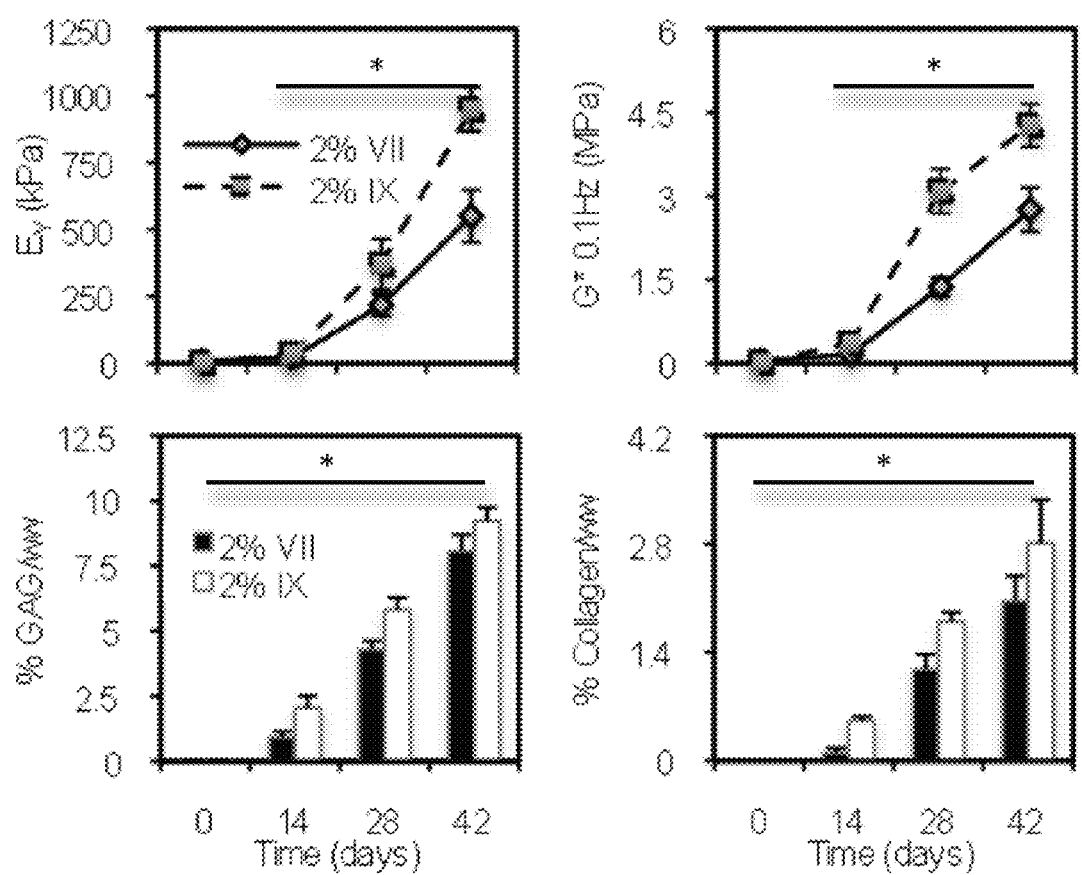
FIG. 32 includes graphical results of experiments.
Figure 33:
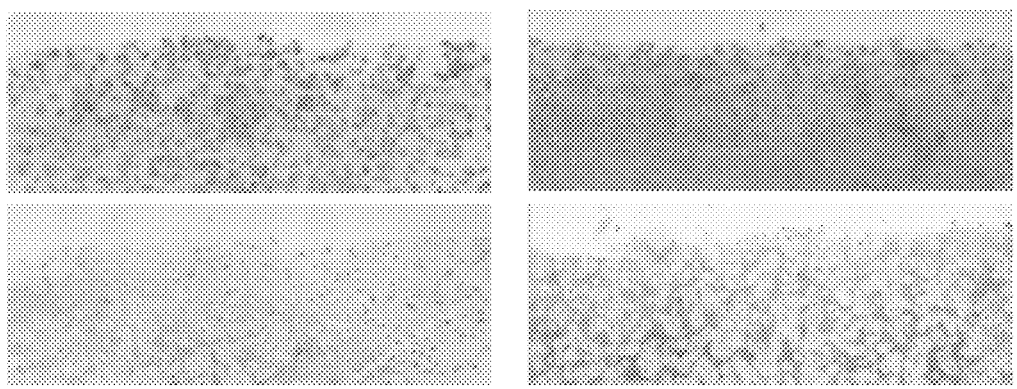
FIG. 33 shows histology of transverse sections of cell-seeded constructs made using different types of agarose.

With identical conditions and culture duration, however, type IX gels exhibited significantly higher mechanical properties and biochemical content (FIG. 32, p<0.05) than type VII gels. To control for the differences in cooling rate during gelation for the two different agarose types, a separate batch of type VII gels was also crosslinked at 4° C. and cultured in parallel. With time in culture, these gels exhibited similar properties to the type VII discs gelled at 25° C. (data not shown, p>0.05). Histology of transverse sections (on day 14) provided visual confirmation of the more rapid matrix accumulation for 1× gels (FIG. 33).

III. Discussion

Scaffolds have been fabricated with similar initial diffusion coefficients to control one parameter governing tissue development. In this study, both types of agarose constructs preserved the chondrocyte phenotype and promoted extracellular matrix development. However, over time, type IX gels exhibited increased properties over type VII constructs even though initial transport properties for dextran were similar. The $E_Y$ and GAG content achieved for both gels in 6 weeks are comparable to that for wrist (carpo-metacarpal) bovine cartilage ($E_Y$: 994±280 kPa, GAG: 6.3±0.9% w/w).

EXAMPLE 7

This Example evaluates whether stiffer engineered cartilage constructs can be achieved by fostering development of tissues that possess central regions with properties more similar to the outer regions. In particular this Example examined the effects of (1) decreasing the initial thickness of the engineered constructs or (2) creating nutrient channels in the constructs, thereby shortening the effective diffusion distance for tissue development.

Example 7 includes three related studies examining matrix content and mechanical properties of chondral constructs produced according to varying methods. In Study 1 of Example 7, constructs of two different thicknesses (thick vs. thin) were compared. In Study 2 of Example 7, the efficacy of nutrient channels in thick constructs was investigated. In Study 3 of Example 7, the number of the channels was increased to study the effects of channels in larger diameter, thick constructs.

Material and Methods for Example 7
A. Sample Preparation and Tissue Culture. Chondrocyte-seeded agarose hydrogel disks were prepared using primary immature bovine chondrocytes (carpal/metacarpal joint) isolated via enzymatic digestion. Cells were encapsulated in 2% (w/v) low melting temperature agarose (Type VII, Sigma) in phosphate buffered saline at 30×10⁶ cells/ml for Study 1 of Example 7 and 60×10⁶ cells/ml for Studies 2 and 3 of Example 7.

In Study 1 of Example 7, the gel-cell mixture was cast into slabs of two different thicknesses: 0.78 (thin) and 2.34 mm (thick). Disks (diameter 4.00 mm) were cored from the slabs and cultured in defined serum-free chondrogenic medium (Dulbecco's Modified Eagle's Medium, 1% insulin transferrin selenium+Premix, 50 μg/ml L-proline, 0.1 μM dexamethasone, 0.9 mM sodium pyruvate, antibiotics), supplemented with ascorbate (50 μg/ml). Recombinant human Transforming Growth Factor-b3 (10 ng/ml) (R&D Systems) was administered the first 2 weeks of culture. Culture media were changed three times a week.

Figure 34:
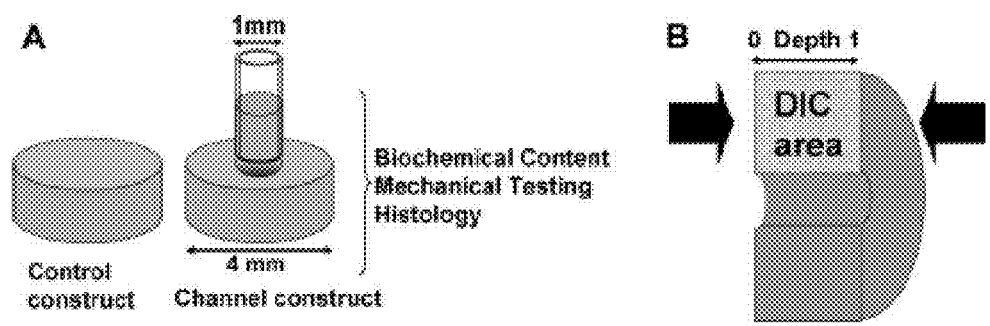
FIG. 34 is a schematic diagram depicting the creation of a channel in the middle of a cell-seeded agarose disk.

In Study 2 of Example 7, a 1 mm diameter channel was created in the middle of the cell-seeded agarose disk (2.34 mm thick, and diameter 4.00 mm) using a biopsy punch (FIG. 34) immediately after construct fabrication (day 0). Disks without a channel served as controls.

For Study 3 of Example 7, 10 mm disks were punched and three 1 mm diameter channels were sub-cored in a centered equilateral triangular pattern, with a mutual separation of 4.3 mm.

B. Mechanical testing. The spatially averaged mechanical properties of construct disks were evaluated at selected time points using a custom table top testing device. The EY was determined under unconfined compression at 10% strain, followed by tests for dynamic moduli ($G^*$) at 0.1, 0.5, and 1 Hz and 1% strain amplitude. The actual area of the channels was deducted from the total cross-sectional area of the constructs for the stress calculations. The relative error introduced by any overestimation of the actual channel size, proportional to the ratio of the area of a 1 mm hole over a 4 mm disk, was expected to be no greater than about 6%. Following average property measurements, constructs were halved and tested for local axial mechanical properties under unconfined compression on a custom microscope testing device and using optimized digital image correlation (FIG. 34(B)).

C. Matrix Molecule Content Analysis. One-half of each construct was weighed wet, lyophilized, reweighed dry, and digested in 0.5 mg/ml Proteinase-K (Fisher Scientific) at 56 C for 16 h. The PicoGreen assay (Invitrogen) was used to quantify the DNA content of the constructs with Lambda phage DNA (0-1 mg/ml) as a standard. The GAG content was measured using dimethylmethylene blue (DMMB, Sigma) dye-binding assay with shark chondroitin sulfate (0-50 mg/ml) as a standard. The overall collagen content was assessed by measuring the orthohydroxyproline (OHP) content via dimethylaminobenzaldehyde and chloramine T assay. Collagen content was calculated by assuming a 1:7.5 OHP-to-collagen mass ratio. The collagen and GAG contents were normalized to the disk wet weight.

D. Histological Analysis. The other halves of the constructs were fixed in a fixative solution (5% acetic acid, 3.7% formaldehyde, 70% ethanol) for 24 h and stored in 70% ethanol solution. After serial dehydration in ethanol, the constructs were embedded in paraffin, sectioned to 8 mm, and mounted onto microscope slides. The samples were then de-waxed, rehydrated, and stained with Safranin-O (Sigma) and Picrosirius red (Sigma) dyes to determine the distribution of GAG and collagen, respectively.

E. Finite Element Modeling (FEM). Osmotic swelling of the tissue-engineered constructs was modeled using a custom finite element program. The objective was to identify conditions that could replicate experimental findings of central cracking in one of the tested groups. The cylindrical engineered construct was divided into two concentric regions; an inner core and outer peripheral region, with respective sizes determined from polarized light images of construct histological slices. This assumption was based on the fact that increasing birefringence was observed in the constructs with increasing culture time and the pattern of histological staining roughly correlates with the pattern of the polarized light microscopy. A hexahedral mesh was created for one-eighth of the tissue-engineered construct with boundary conditions prescribed based on symmetry. Several combinations of material properties were explored, consistent with experimental measurements, which might explain the crack formation observed in the control group for Study 2 of Example 7. In the final analysis the tensile moduli of the respective regions were assigned values consistent with the intensity and distribution of Picrosirius red staining of collagen across the constructs, suitably scaled using an upper limit from experimental values previously reported. A tensile stiffness of 2.5 MPa and 120 kPa were thus assigned to the periphery and core of the mesh, respectively. GAG content was estimated to be 8% of the wet weight in the core and 10% in the periphery of the constructs based on the results of the GAG quantification assay. Assuming two negative charges per chondroitin sulfate isomer and a molecular weight of 513 g/mol, a fixed charge density (cF) was calculated from the GAG content to be 458 mEq/L (10% GAG) and 367 mEq/L (8% GAG). The water content was estimated to be 85% of wet weight based on the difference between the dry weight and wet weight of the constructs. The material properties used in FEM are summarized in Table 2.

TABLE 2

| Material Properties used in FEM | | |
|---|---|---|
| Model parameters | Core | Periphery |
| GAG (w/w (%)) | 8 | 10 |
| Charge density (mEq/L) | 367 | 458 |
| Tensile modulus (MPa) | 0.12 | 2.5 |
| Water content (%) | 85 | 85 |

F. Statistical Analysis. Statistica (Statsoft) was used to perform statistical analyses using two way analysis of variance (ANOVA) and the Tukey honestly significant differences Post Hoc test of the means (n=4-6 samples per group) with culture duration and experimental groups as independent factors.

Figure 35:
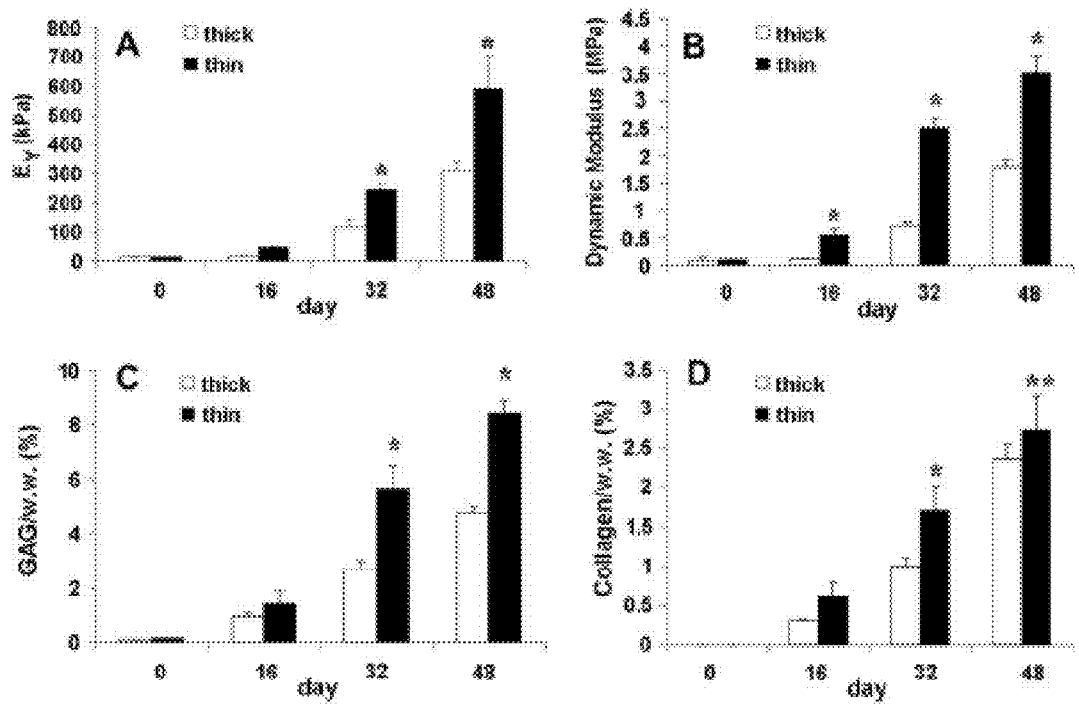
FIG. 35 includes graphical results of experiments.

Results of Study 1. Study 1 of Example 7 showed the $E_Y$ of the thin constructs were two-fold greater than that of the thick constructs, reaching values of 246±21 kPa and 592±111 kPa on days 32 and 48, respectively [P<0.005, FIG. 35(A, B)]. G* (frequency=0.5 Hz) of the thin constructs were 3.5±0.3 MPa on day 48, twice as much as that of the thick constructs (1.8±0.1 MPa) at the same time points. The thin constructs also developed significantly higher GAG and collagen content than the thick constructs after day 14 [P<0.005 FIG. 35(C, D)].

On day 48, the GAG content of the thin constructs reached 8.4±0.49% wet weight (% w/w) compared to thick constructs which had GAG content of only 4.8±0.23% w/w. The collagen content of the thin constructs was significantly higher than that of the thick constructs on both day 32 (1.71±0.31% w/w vs. 1.00±0.10% w/w, P<0.005) and day 48 (2.73±0.43% w/w vs. 2.36±0.19% w/w, P<0.05). The difference in collagen content between the two groups on day 48 was less than that on day 32. The thin constructs had a greater DNA content and GAG/DNA ratio as compared to the thick constructs after day 16. Increased GAG content in the thin constructs is attributable to both increased cell proliferation and elevated GAG production of individual cells.

Figure 37:
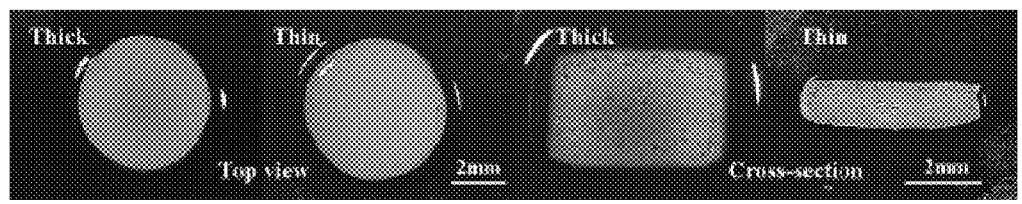
FIG. 37 contains photographs of top and cross-sectional views of the cell-seeded constructs.

Spatial $E_Y$ profiles across the longitudinal depth of the cylindrical disks varied among the groups. The thin constructs had a significantly softer layer on the surface taking up a large part of the applied compressive strain and a uniformly stiff center with minimal strain [FIG. 36(B, E)]. In contrast, thick constructs developed significantly stiffer edges and a softer central core as indicated by the U-shaped strain profile across the construct depth [FIG. 36(A, D)]. Top and cross-sectional views of the constructs showed that the thick constructs were more opaque at the peripheral regions than in the center whereas the thin constructs appeared homogeneous in translucency (FIG. 37). Immunohistochemistry indicated that the cells produced predominantly Type II collagen with minimal Type I collagen.

Figure 38:
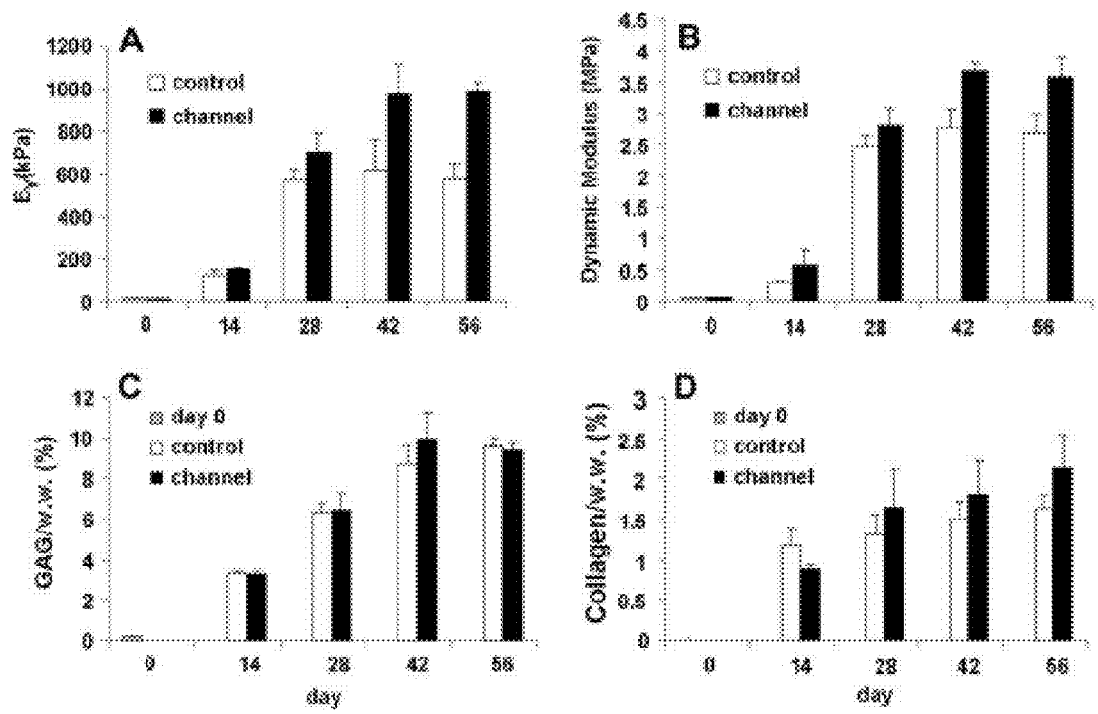
FIG. 38 includes graphical results of experiments.

Results of Study 2. Study 2 showed the process of punching channels did not affect cell viability at the cutting surface or other areas of the constructs. The moduli of the constructs with a channel were significantly higher than controls from day 28 onward. Furthermore, the moduli of the control disks (without a channel) started to plateau after day 28 and stagnated afterward until day 56, reaching values of $E_Y$=600 kPa and G*=2.7 MPa, respectively, whereas those of the disks with a channel continued to increase until day 42 and plateaued at a higher level of $E_Y$=1000 kPa and G*=3.6 MPa. The channel constructs also possessed more uniform local stiffness along the axial direction, whereas constructs without channels developed significantly stiffer edges and a softer central core as indicated by the U-shaped strain profile across the depth of the constructs [FIG. 36(C, F)]. However, overall GAG and collagen content of the two groups were not statistically different [FIG. 38(C, D)].

Figure 39:
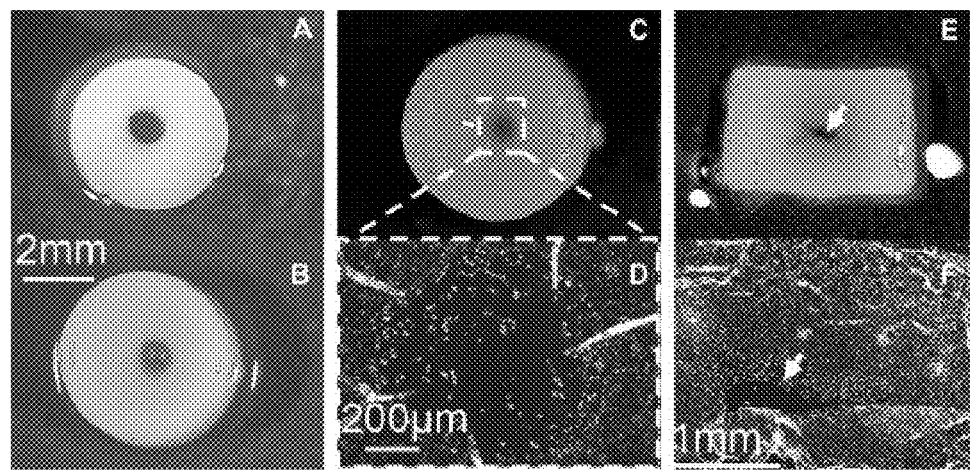
FIG. 39 contains photographs of cell-seeded constructs which have channels.

The channels were gradually filled in with translucent material and infiltrated by cells [FIG. 39(A, C, F)]. Picrosirius red staining revealed that the control constructs exhibited a mesh-like extracellular matrix structure in the peripheral regions, not apparent in the center. In contrast, the channeled disks exhibited more uniform staining throughout their cross-section [FIG. 40(A, C)]. This disparity in structural organization between the construct types is even more pronounced in polarized microscopy images of these same tissue sections [FIG. 40(D, E)]. Histology also showed more intense Safranin-O staining in the periphery of the control constructs than in the center [FIG. 40 (G, I)].

Figure 41:
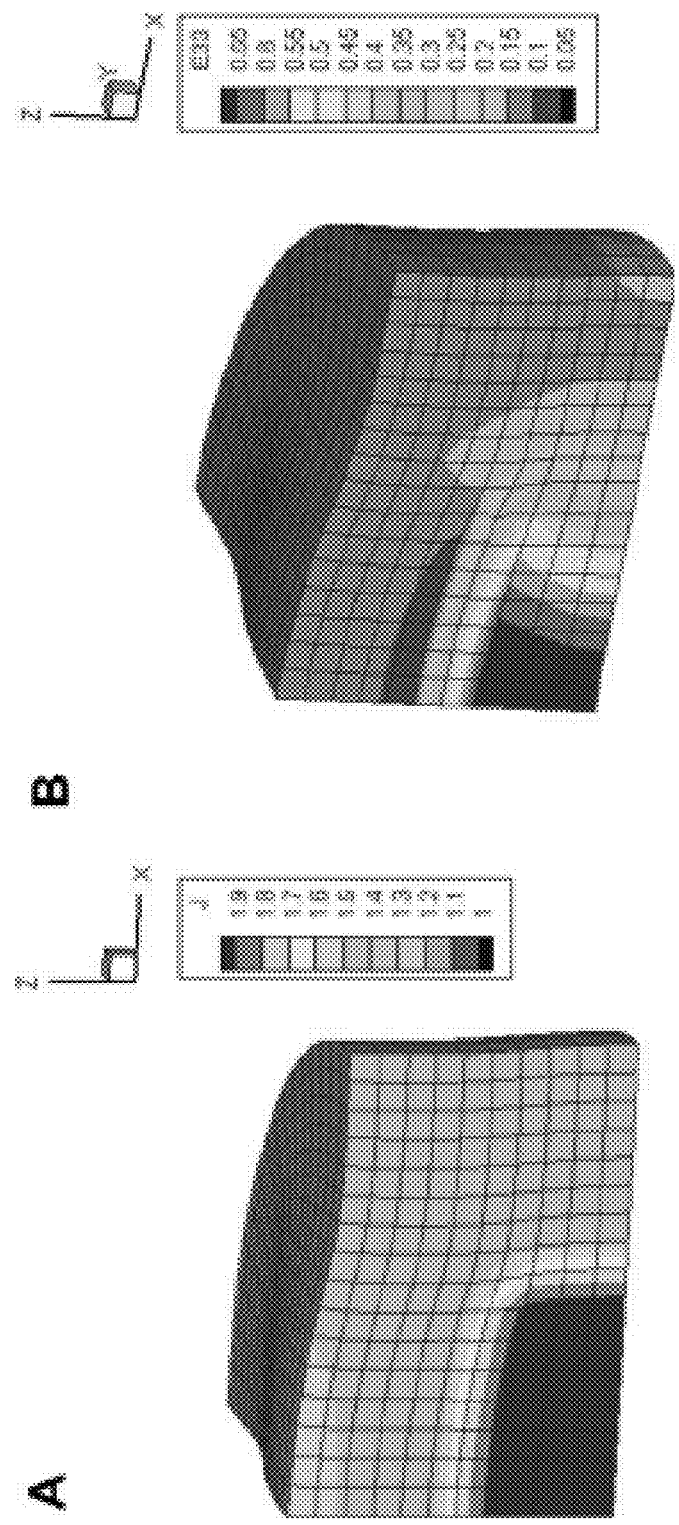
FIG. 41 shows (A) Volume expansion and (B) the Lagrangian strain in the axial direction (z axis), for model representative of tissue constructs in Study 2. From symmetry considerations, only one-eighth of the construct was modeled.

A large crack parallel to the axial disk faces was observed in the center of the control constructs on day 56 [FIG. 39(D, E)], likely resulting from the osmotic swelling due to GAG as well as low tensile stiffness in the center of the control constructs due to the absence of an organized collagen network (as seen in the periphery), as deduced from the finite element analysis. On day 56 the constructs exhibited swelling to about 70% of initial volume. The FEM results predicted a similar amount of volume expansion for the model variables chosen. The volume of the elements expanded by about 90% in the center of the constructs and by about 50% in the periphery region due to osmotic swelling [FIG. 41(A)]. The Lagrangian strain in the axial direction of the constructs was also significantly higher in the core region of the constructs, reaching a value of 0.55 whereas it remained below 0.15 in the periphery [FIG. 41(B)]. Though the finite element analysis did not explicitly model crack formation, the larger strains observed at the center are consistent with the experimental observation of cracking.

Figure 42:
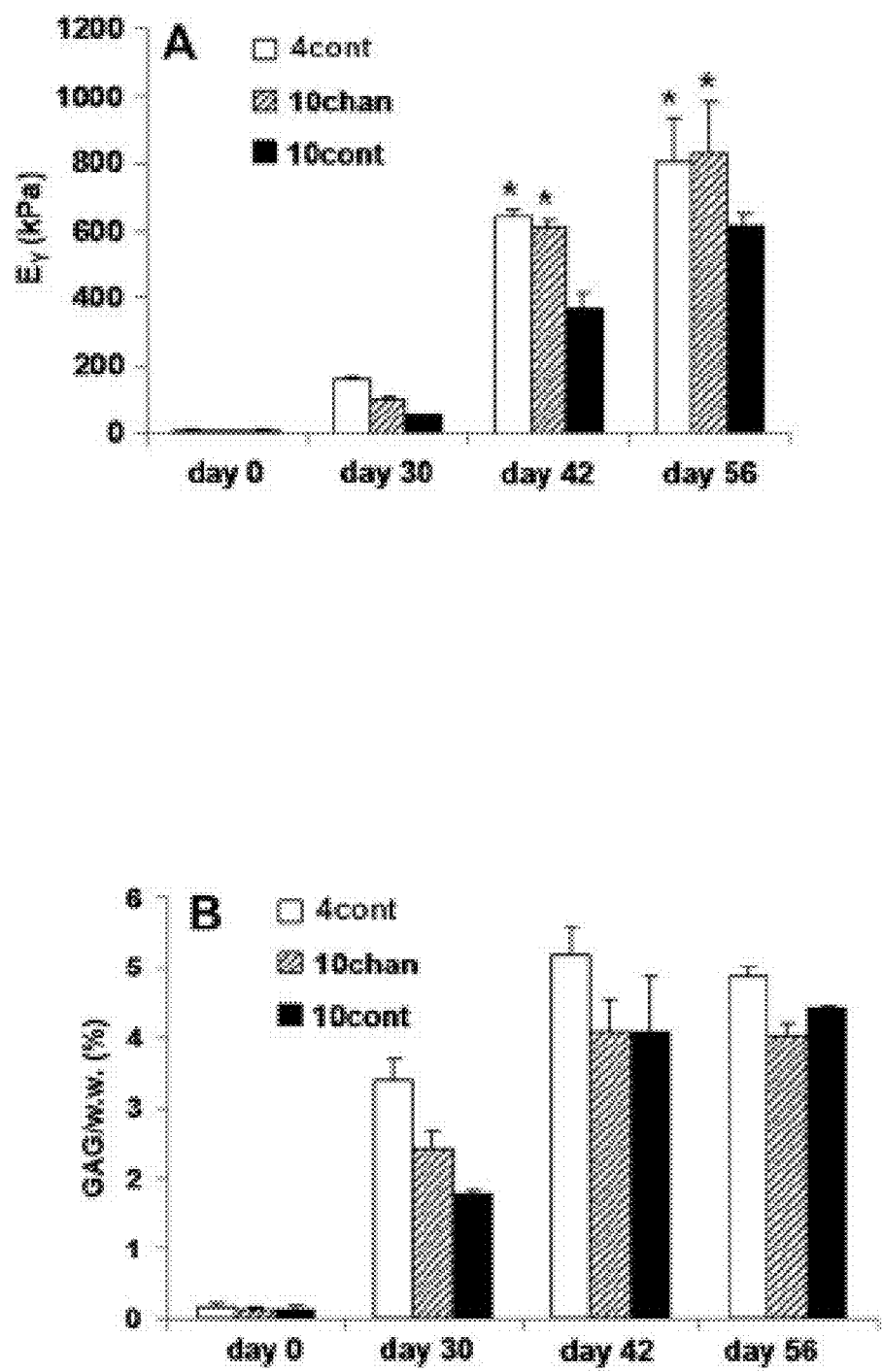
FIG. 42 includes graphical results of experiments.

Results of Study 3. For Study 3, large constructs of 10 mm diameter with channels developed significantly higher mechanical stiffness as compared to the control constructs without channels [FIG. 42(A)]. However, in analogy to observations in 4 mm diameter constructs, the GAG content is similar between the two groups [FIG. 42(B)]. The 10 mm diameter control constructs exhibited lower mechanical stiffness and GAG content as compared to the 4 mm diameter control constructs [FIG. 42(A, B)].

The results of Study 1 of Example 7 show that reducing the thickness of cell-seeded agarose constructs by one-third promotes more uniform material properties through the construct depth, as a result of the reduced transport path length. The mechanism underlying the softer outer layers observed in the thin constructs is unclear, and may be related to diffusive loss of GAG from the periphery. It appears that there may be a critical length >0.78 mm where diffusion limitations will lead to inhomogeneous cartilaginous tissue development under free-swelling culture conditions. While Study 1 showed that thin constructs developed superior material properties, there remains a clinical need for thicker tissue constructs (e.g., about 5 mm thick for the human patella or tibial plateau).

Study 2 showed that channels created on day 0 clearly provide many advantages, such as improved material properties and more homogeneous composition, and no apparent adverse effects. An array of channels can permit cultivation of single constructs having appropriate thickness, with the channels eventually filling naturally. The application of physiologic deformational loading with concomitant convective transport would be expected to further enhance the passive strategies to increase nutrient diffusion described in this investigation.

Diffusion channels with a diameter of less than about 1 mm became occluded within 1 week of culture, channels having a 1.5 mm diameter channels remained completely open after 28 days; and 1 mm diameter channels gradually shrank in size and were partially sealed up by day 28. Channels introduced at a late stage of culture, when the cells had already produced significant extracellular matrix, rather than immediately after construct fabrication on day 0, did not influence construct properties 14 days later. For the application of channels to be most efficacious, the channels should remain open long enough to play a role in providing greater nutrient access to chondrocytes when significant tissue matrix elaboration has occurred (and where a plateauing of tissue properties is often noted).

In Study 2, constructs (2.34 mm thick) were seeded with 60 million cells/ml, which is twice that of Study 1. This culture condition is expected to increase the effect of nutrient limitations on tissue development, with increases in construct dimension and nutrient consumption.

Figure 40:
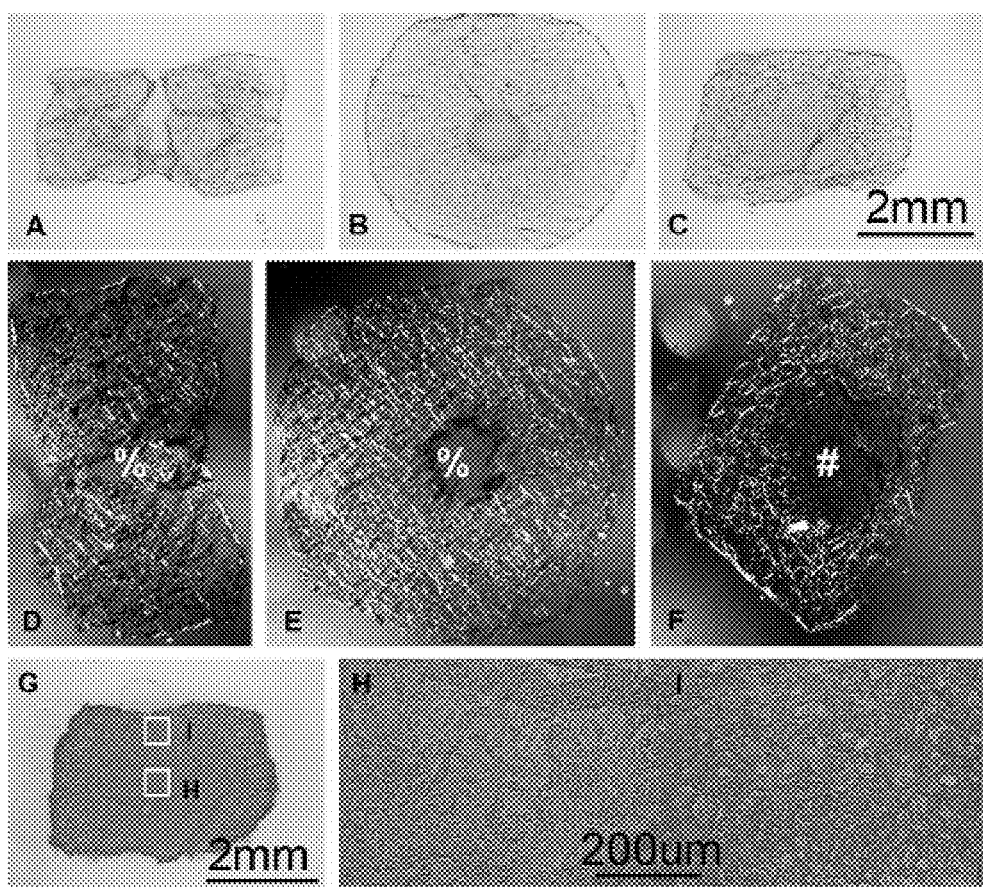
FIG. 40 contains photographs of cell-seeded constructs which have channels.

The introduction of nutrient channels in the current study not only elevated construct stiffness but also delayed the plateauing of the mechanical properties of the constructs (FIG. 38), probably due to the improved nutrient delivery to the center of the constructs. The average content of GAG and collagen, the two major matrix constituents of articular cartilage, was similar for constructs with and without a central channel. However, there was a striking difference in the structural organization of the fibrillar network between the construct types (FIG. 40). As a result of the channels, the provision of nutrients through the construct periphery and center increased the surface area for diffusion by only 10.5% but decreased the path for radial diffusion by 50%; this led to a more uniform fibrillar network of extracellular matrix, which was in contrast to the presence of an organized network of fibers only in the outer peripheral regions as well as occasional cracking of the control constructs.

The central crack observed in the control constructs likely resulted from osmotic swelling due to GAG as well as low tensile stiffness in the center of the control constructs due to absence of organized collagen network as compared to the periphery. Cracks are not typically found in low seeding density (30 million cells/ml) constructs. Its occurrence in the high-seeding density constructs is reflective of the higher GAG content achieved with the higher seeding density. The finite element model provides insights to the structure-function relationships developed in the engineered cartilage tissue.

In the engineered cartilage, GAG levels were similar to, or even higher than native levels (about 6% w/w), producing significant osmotic pressures (estimated at about 0.12 MPa when using ideal Donnan law) and swelling. Whereas swelling is resisted by the collagen matrix in native tissue, the constructs' collagen levels were only a fraction of the native values (about 20% w/w), and mostly deficient at the center of the construct. The FE model of a construct deficient in collagen at its center predicted a swelling strain there that was four times greater than in the peripheral region. As the yield strain for 2% w/v Type VII agarose is about 0.2, these results suggest that exceedingly high swelling-strains in the central region of the constructs may give rise to construct cracking. Therefore, the elevated GAG content and non-uniform distribution of collagen created conditions that supported internal cracking.

Applied mechanical loading has been shown to promote solute transport into cartilage and engineered constructs. However, the enhancement of nutrient transport into engineered constructs with dynamic loading will be less significant in constructs of larger dimension (such as targeted for repair of an entire articular surface) or with more elaborated matrix, which can hinder the transport of the nutrients. While mechanical loading continues to be attractive in promoting the growth of engineered cartilage (via a biophysical stimulus and enhanced transport), mechanical loading regimes can be supplemented by providing nutrient channels in the cell-seeded scaffolds, particularly when producing larger sized engineered tissue. While the introduction of channels or "holes" in the engineered cartilage may raise some concerns, the results of Example 7 indicate these channels are likely to completely seal themselves with additional culturing as the channels are beginning to be filled in with tissue by culture day 56. If constructs with unsealed channels were to be implanted, they would be expected to seal in vivo, as observations in the literature indicate that cartilage defects of less than 3 mm diameter heal spontaneously. In addition, clinically accepted cartilage repair strategies that use single or multiple osteochondral grafts also introduce irregular holes to the articular surface.

EXAMPLE 8

The Response of Adult Engineered Canine Cartilage to the Sequential or Combined Application of TGF-β3 and IGF-1

As described above, growth factor "priming" during monolayer expansion results in mature canine chondrocytes that can form an engineered cartilage tissue with physiologic tissue properties. These properties can be further improved with the addition of insulin-like growth factor-I (IGF-I) during culture. In the present example, this growth factor was added using two different temporal profiles since the timing and combination of various stimuli can elicit vastly different responses in engineered cartilage tissue.

I. Materials and Methods

Figure 43:
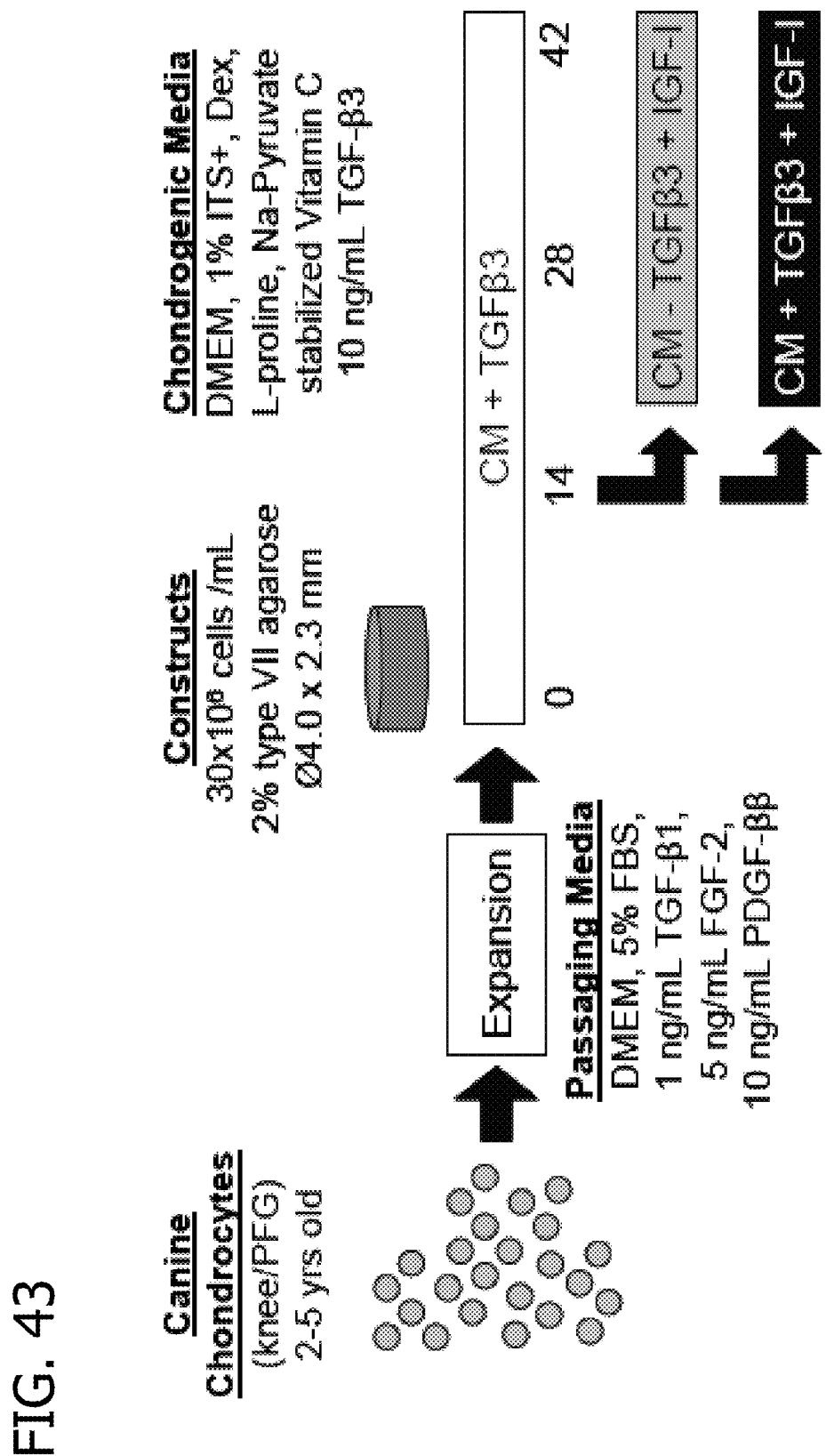
FIG. 43 is a schematic diagram depicting the experimental design of Example 8, which examines the response of adult engineered canine cartilage to the sequential or combined application of TGF-beta3 and IGF-1.

A. Experimental Design. The experimental design is shown in FIG. 43. Primary or passaged adult canine chondrocytes were encapsulated in agarose and cultured with TGF-β3. After 2 weeks, a subset of chondrocyte-seeded constructs were cultured with or with TGF-β3 and/or IGF-I.

B. Cell culture. Canine chondrocytes were isolated from the cartilage of adult mongrel dogs (2-5 years old, 90+ lbs.). Cells were passaged in DMEM with 10% FBS, 1 ng/mL TGF-β1, 5 ng/mL FGF-2, and 10 ng/mL PDGF-BB. Passaged chondrocytes were suspended in 2% agarose at $30 \times 10^6$ cells/mL. Disks (4.0 mm diameter×1.5 mm) were cultured in 35 mL of chondrogenic media and ascorbate at 37° C. and 5% $CO_2$. TGF-β3 at 10 ng/mL was added for the first 14 days in culture and then the constructs were split in to three groups: TGF-β3 only ("+TGF-IGF"), IGF-I only (100 ng/mL, "−TGF+IGF"), or TGF-β3 with IGF-I ("+TGF+IGF"). Media was changed every 48 h.

C. Mechanical Testing. Young's modulus ($E_Y$) and dynamic modulus ($G^*$) of samples (n=4-5 per group) was calculated from static and 1 Hz unconfined compression testing on day 0, 14, 28, and 42. Following testing, constructs were weighed wet and frozen for biochemical analysis.

D. Biochemical Analysis. GAG and collagen contents were measured for each sample and normalized to construct wet weight (% w/w).

E. Statistics. Data were analyzed using 2-way ANOVA (α=0.05), with time and growth factor treatment as factors. Fisher LSD post-hoc test was used to determine significant differences between means (p≤0.05).

II. Results

Figure 44:
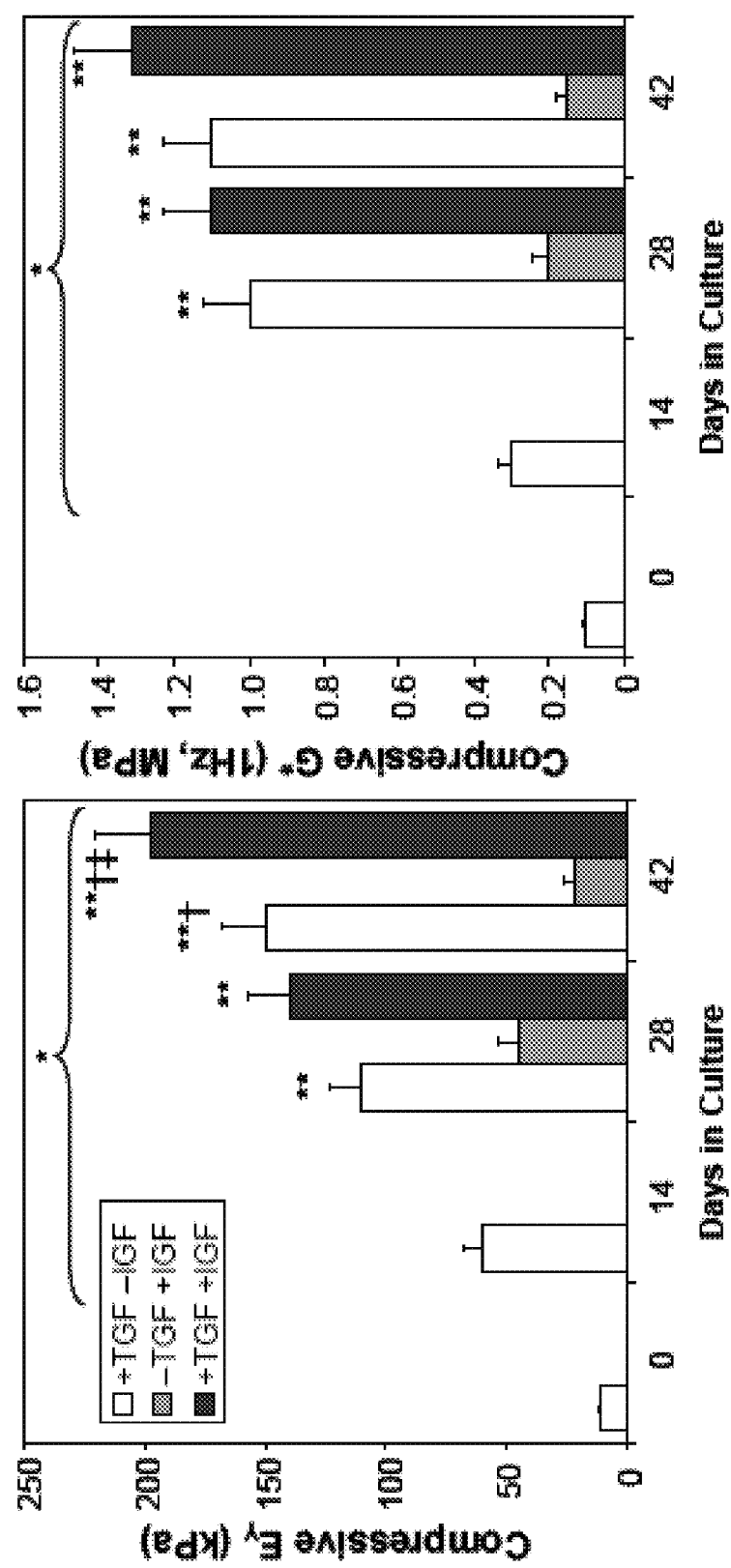
FIG. 44 includes graphical results of experiments.
Figure 45:
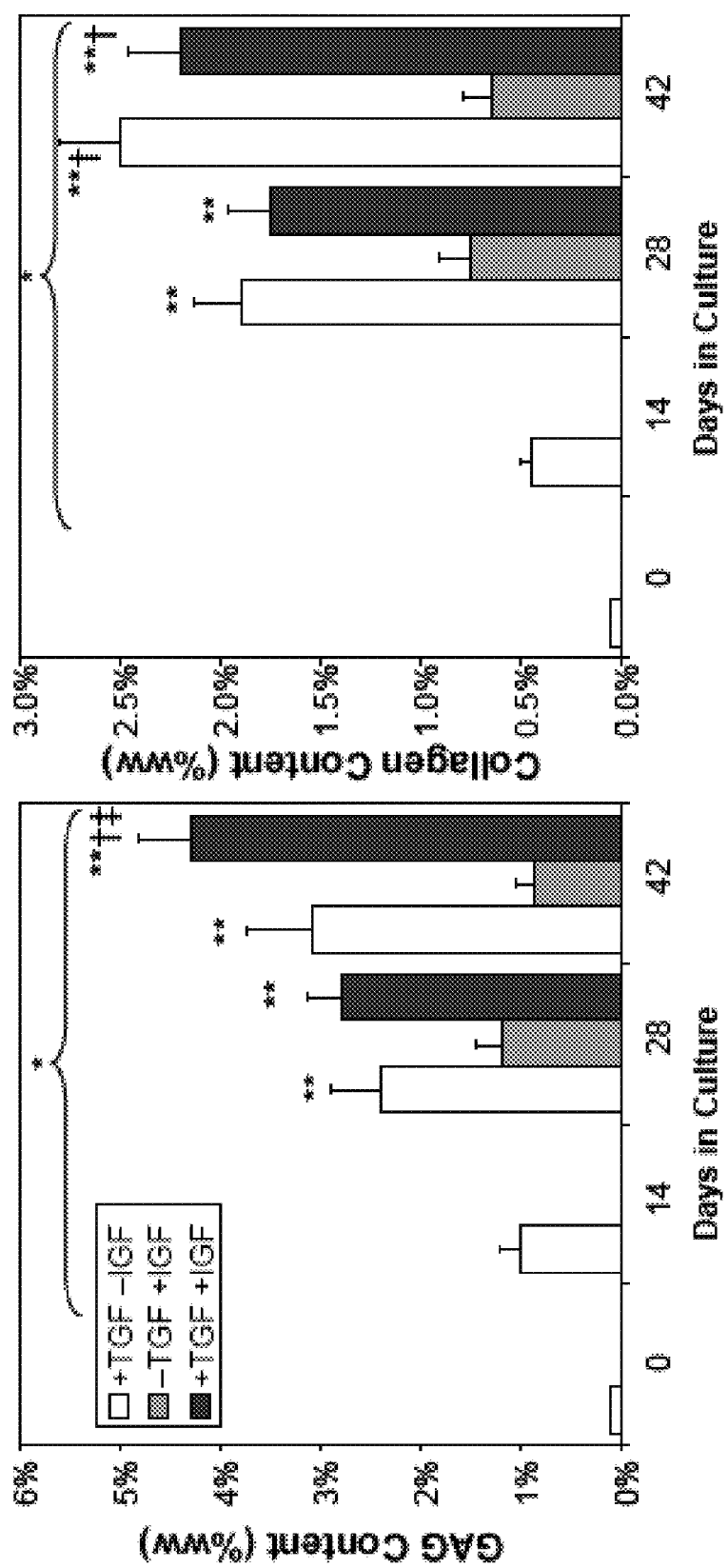
FIG. 45 includes graphical results of experiments.

Engineered canine cartilage cultured with TGF-β3 only (+TGF-IGF) improved in tissue properties by day 14 and continued to do so over the 42 day time period reaching values of $E_Y$ ~150 kPa, $G^*$ ~1.2 MPa, GAG ~3.25% w/w, and collagen ~2.5% w/w (FIGS. 44, 45). The sequential substitution of TGF-β3 with IGF-I (−TGF+IGF) on day 14 halted tissue elaboration over the remaining experimental culture period (FIGS. 44, 45). The combination of TGF-β3 and IGF-I, however, elicited the highest day 42 values for $E_Y$ (~210 kPa) and GAG content (~4.25% w/w) of all experimental groups.

FIG. 44 shows the Young's modulus (left) and dynamic modulus (right) of canine engineered cartilage. The removal of TGF-β3 from the culture media and substitution with IGF-I on day 14 lead to least mechanical competent tissues by day 42. Combined TGF/IGF treatment lead to the stiffest engineered cartilage tissue. * p<0.05 vs. day 0; ** p<0.05 vs. day 14; † p<0.05 vs. day 28; ‡ p<0.05 vs. other 2 groups.

FIG. 45 shows the GAG (left) and collagen (right) content of canine engineered cartilage. The removal of TGF-β3 from the culture media and substitution with IGF-I on day 14 lead to inhibition of further matrix synthesis over time in culture. Combined TGF/IGF treatment lead to the highest GAG content in engineered constructs. * p<0.05 vs. day 0; **p<0.05 vs. day 14; † p<0.05 vs. day 28; ‡ p<0.05 vs. other 2 groups.

III. Discussion

The addition of IGF-I in combination with TGF-β3 led to the highest compressive Young's modulus and GAG content in the engineered cartilage tissues cultivated in this study, comparable to previously measured values for canine patella-femoral groove cartilage. The results between the sequential substitution and combination of TGF-β3 with IGF-I imply that there exists "cross talk" between growth factor signaling in adult canine chondrocytes. From a clinical perspective, the results reinforce the potential to expand mature allogeneic or autologous chondrocytes for regenerative medicine strategies (tissue engineering, ACI).

What is claimed is:

1. An implant for resurfacing or repairing one or more articular cartilage bearing surfaces of a biological organism, the implant comprising:
    an engineered cartilaginous tissue comprising: (a) a scaffold comprising a biocompatible hydrogel; and (b) a plurality of living chondrocytes supported by the scaffold; and
    a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
    wherein the porous substrate comprises a metal.

2. An implant as set forth in claim 1 wherein the porous substrate comprises tantalum.

3. An implant as set forth in claim 1 wherein the scaffold comprises alginate.

4. An implant as set forth in claim 1 wherein the engineered tissue has a bearing surface that has substantially the same shape as at least a portion of one of said one or more articular cartilage bearing surfaces that is to be resurfaced or repaired.

5. An implant as set forth in claim 1 wherein the engineered tissue has a bearing surface that has substantially the same shape as one of said one or more articular cartilage bearing surfaces that is to be resurfaced.

6. An implant as set forth in claim 1 wherein the engineered tissue comprises Type II collagen in an amount in the range of about 2 percent (w/w) to about 8 percent (w/w).

7. An implant as set forth in claim 1 wherein the engineered tissue has a glycosaminoglycan (GAG) content in the range of about 4 percent (w/w) to about 10 percent (w/w).

8. An implant as set forth in claim 1 wherein the engineered tissue has an equilibrium Young's modulus ($E_Y$) of at least about 150 kPa.

9. An implant as set forth in claim 1 wherein the scaffold comprises agarose.

10. An implant as set forth in claim 1 wherein the engineered tissue comprises Type II collagen in an amount that is 4 percent (w/w) or more.

11. An implant as set forth in claim 1 wherein the engineered cartilaginous tissue has a bearing surface comprising a plurality of collagen fibers, said collagen fibers at the bearing surface being oriented so a majority of the fibers are generally parallel to the bearing surface.

12. An implant as set forth in claim 1 wherein said plurality of cells that are included the scaffold extending into at least some of the voids in the porous substrate comprises some of said chondrocytes of the engineered cartilaginous tissue.

13. An implant for resurfacing or repairing one or more articular cartilage bearing surfaces of a biological organism, the implant comprising:
    an engineered cartilaginous tissue comprising: (a) a scaffold comprising a biocompatible hydrogel; and (b) a plurality of living chondrocytes supported by the scaffold; and
    a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
    wherein the engineered tissue comprises Type II collagen in an amount that is 4 percent (w/w) or more.

14. An implant as set forth in claim 13, wherein the engineered cartilaginous tissue has an equilibrium Young's modulus ($E_Y$) of at least about 150 kPa.

15. An implant as set forth in claim 14 wherein the porous substrate comprises a porous substrate selected from the group consisting of synthetic polymers and biologic materials.

16. An implant as set forth in claim 15 wherein the porous substrate comprises a synthetic polymer selected from the group consisting of polycaprolactone, poly-l-lactic acid, and polyglycolic acid.

17. An implant as set forth in claim 14 wherein the engineered tissue has an equilibrium Young's modulus ($E_Y$) in the range of about 150 kPa to about 1500 kPa.

18. An implant as set forth in claim 14 wherein the engineered tissue has an equilibrium Young's modulus ($E_Y$) in the range of about 185 kPa to about 1300 kPa.

19. An implant as set forth in claim 14 wherein the engineered tissue has an equilibrium Young's modulus ($E_Y$) in the range of about 275 kPa to about 1300 kPa.

20. An implant as set forth in claim 14 wherein the engineered tissue comprises Type II collagen in an amount ranging from 4 percent (w/w) to about 8 percent (w/w).

21. An implant as set forth in claim 14 wherein the engineered tissue has a glycosaminoglycan (GAG) content in the range of about 4 percent (w/w) to about 10 percent (w/w).

22. An implant as set forth in claim 14 wherein the engineered tissue has a bearing surface that has substantially the same shape as at least a portion of one of said one or more articular cartilage bearing surfaces that is to be resurfaced or repaired.

23. An implant as set forth in claim 14 wherein the scaffold comprises agarose.

24. An implant as set forth in claim 14 wherein the engineered cartilaginous tissue has a bearing surface comprising a plurality of collagen fibers, said collagen fibers at the bearing surface being oriented so a majority of the fibers are generally parallel to the bearing surface.

25. An implant as set forth in claim 13 wherein the porous substrate comprises tantalum.

26. An implant as set forth in claim 13 wherein the porous substrate comprises a porous substrate selected from the group consisting of synthetic polymers and biologic materials.

27. An implant as set forth in claim 13 wherein the scaffold comprises alginate.

28. An implant as set forth in claim 13 wherein the engineered tissue has a bearing surface that has substantially the same shape as at least a portion of one of said one or more articular cartilage bearing surfaces that is to be resurfaced or repaired.

29. An implant as set forth in claim 13 wherein the engineered tissue has a bearing surface that has substantially the same shape as one of said one or more articular cartilage bearing surfaces that is to be resurfaced.

30. An implant as set forth in claim 13 wherein the engineered tissue has a glycosaminoglycan (GAG) content in the range of about 4 percent (w/w) to about 10 percent (w/w).

31. An implant for resurfacing or repairing one or more articular cartilage bearing surfaces of a biological organism, the implant comprising:
    an engineered cartilaginous tissue comprising: (a) a scaffold comprising a biocompatible hydrogel; and (b) a plurality of living chondrocytes supported by the scaffold; and
    a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
    wherein the engineered tissue has a glycosaminoglycan (GAG) content in the range of about 4 percent (w/w) to about 10 percent (w/w).

32. An implant as set forth in claim 31 wherein the porous substrate comprises tantalum.

33. An implant as set forth in claim 31 wherein the porous substrate comprises a porous substrate selected from the group consisting of synthetic polymers and biologic materials.

34. An implant as set forth in claim 31 wherein the scaffold comprises agarose.

35. An implant as set forth in claim 31 wherein the engineered tissue has a bearing surface that has substantially the same shape as at least a portion of one of said one or more articular cartilage bearing surfaces that is to be resurfaced or repaired.

36. An implant as set forth in claim 31 wherein the engineered tissue has a bearing surface that has substantially the same shape as one of said one or more articular cartilage bearing surfaces that is to be resurfaced.

37. An implant for resurfacing or repairing one or more articular cartilage bearing surfaces of a biological organism, the implant comprising:
- an engineered cartilaginous tissue comprising: (a) a scaffold comprising at least one of the group consisting of agarose, alginate, and polyethylene glycol; and (b) a plurality of living chondrocytes supported by the scaffold; and
- a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
- wherein the porous substrate comprises a metal.

38. An implant for resurfacing or repairing one or more articular cartilage bearing surfaces of a biological organism, the implant comprising:
- an engineered cartilaginous tissue comprising: (a) a scaffold comprising at least one of the group consisting of agarose, alginate, and polyethylene glycol; and (b) a plurality of living chondrocytes supported by the scaffold; and
- a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
- wherein the engineered tissue comprises Type II collagen in an amount that is 4 percent (w/w) or more.

39. An implant for resurfacing or repairing one or more articular cartilage bearing surfaces of a biological organism, the implant comprising:
- an engineered cartilaginous tissue comprising: (a) a scaffold comprising at least one of the group consisting of agarose, alginate, and polyethylene glycol; and (b) a plurality of living chondrocytes supported by the scaffold; and
- a biocompatible porous substrate secured to the engineered tissue for attaching the implant to a native bone of the biological organism, the porous substrate being substantially free of trabecular bone and having a plurality of interconnected voids, the scaffold including a plurality of cells extending from exterior of the porous substrate into at least some of the voids in the porous substrate,
- wherein the engineered tissue has a glycosaminoglycan (GAG) content in the range of about 4 percent (w/w) to about 10 percent (w/w).

* * * * *